(12) United States Patent
Gougoutas et al.

(10) Patent No.: US 8,236,847 B2
(45) Date of Patent: Aug. 7, 2012

(54) CRYSTAL FORMS OF SAXAGLIPTIN AND PROCESSES FOR PREPARING SAME

(75) Inventors: Jack Z. Gougoutas, Princeton, NJ (US); Mary F. Malley, Princeton, NJ (US); John D. DiMarco, Princeton, NJ (US); Xiaotian S. Yin, Princeton, NJ (US); Chenkou Wei, Princeton, NJ (US); Jurong Yu, Princeton, NJ (US); Truc Chi Vu, Princeton, NJ (US); Gregory Scott Jones, Princeton, NJ (US); Scott A. Savage, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/081,341

(22) Filed: Apr. 6, 2011

(65) Prior Publication Data

US 2011/0257085 A1    Oct. 20, 2011

Related U.S. Application Data

(62) Division of application No. 12/105,316, filed on Apr. 18, 2008, now Pat. No. 7,943,656.

(60) Provisional application No. 60/912,950, filed on Apr. 20, 2007.

(51) Int. Cl.
    *A61K 31/403* (2006.01)
    *C07D 209/02* (2006.01)
(52) U.S. Cl. ........................................ 514/412; 548/452
(58) Field of Classification Search ................... 514/412; 548/452
    See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau et al. |
| 5,612,359 A | 3/1997 | Murugesan |
| 5,614,492 A | 3/1997 | Habener |
| 5,686,104 A | 11/1997 | Mills et al. |
| 5,691,322 A | 11/1997 | Robl |
| 5,712,279 A | 1/1998 | Biller et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |

(Continued)

FOREIGN PATENT DOCUMENTS

EP          0 221 025          5/1987

(Continued)

OTHER PUBLICATIONS

Berge, Stephen, M. et al.: Pharmaceutical Salts, Journal of Pharmaceutical Sciences, Jan. 1977, pp. 1-19.
Morissette et al. Advanced Drug Delivery Reviews 2004, 56, 275-300.
Vippagunta et al., abstract, Vippagunta, Sudha R. "Crystalline Solids." Advanced Drug Delivery Reviews 48(2001): 3-26.

(Continued)

*Primary Examiner* — Rebecca Anderson
*Assistant Examiner* — Samantha Shterengarts
(74) *Attorney, Agent, or Firm* — McDonnell Boehnen Hulbert & Berghoff LLP

(57) ABSTRACT

Physical crystal structures of a compound of the formula I:

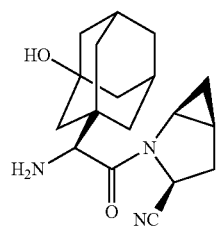

(saxagliptin)

are provided including the free base monohydrate thereof (form H-1) and the hydrochloric acid salt thereof, including hydrochloric acid salt containing 0.75 equivalent of $H_2O$ (form H0.75-3) and hydrochloric acid salt containing 2 equivalents of $H_2O$ (form H2-1), and hydrochloric acid salt Pattern P-5, preferably in substantially pure form, and other forms as described herein, pharmaceutical compositions containing structures of compound I or IA, processes for preparing same, intermediates used in preparing same, and methods of treating diseases such as diabetes using such structures.

31 Claims, 30 Drawing Sheets

U.S. PATENT DOCUMENTS

| | | | |
|---|---|---|---|
| 5,827,875 | A | 10/1998 | Dickson et al. |
| 5,885,983 | A | 3/1999 | Biller et al. |
| 5,962,440 | A | 10/1999 | Sulsky |
| 6,043,265 | A | 3/2000 | Murugesan et al. |
| 6,395,767 | B2 | 5/2002 | Robl et al. |
| 6,414,126 | B1 | 7/2002 | Ellsworth et al. |
| 6,515,117 | B2 | 2/2003 | Ellsworth et al. |
| 6,653,314 | B2 | 11/2003 | Cheng et al. |
| 2005/0090539 | A1 | 4/2005 | Vu et al. |
| 2005/0260712 | A1 | 11/2005 | Politino et al. |
| 2005/0266080 | A1 | 12/2005 | Desai et al. |

FOREIGN PATENT DOCUMENTS

| | | |
|---|---|---|
| EP | 0 142 146 | 8/1988 |
| FR | 2 596 393 | 4/1986 |
| GB | 2 205 837 | 12/1998 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/38722 | 7/2000 |
| WO | WO 00/39077 | 7/2000 |
| WO | WO 01/21602 | 3/2001 |
| WO | WO 01/68603 | 9/2001 |
| WO | WO 03/033671 | 4/2003 |
| WO | WO 2006/020664 | 2/2006 |

OTHER PUBLICATIONS

A. Maureen Rouhi, The Right Stuff: From research and development to the clinic, getting drug crystals right is full of pitfalls, Chem. & Eng. News, 81(8), Feb. 24, 2003, 32-35.

Brittain, H.G. (Polymorphism in Pharmaceutical Solids—Drugs and the Pharmaceutical Sciences, V. 95; New York Marcel, Dekker, Inc., 1999), p. 236.

Ashworth et al., "2-Cyanopyrrolidides as Potent, Stable Inhibitros of Deipeptidyl Peptidase IV", Biog. & Med. Chem. Lett., vol. 6, No. 10, pp. 1163-1166, (1996).

Ashworth et al., "4-Cyanothiazolidides as Very Potent, Stable Inhibitors of Dipeptidyl Peptidase IV", Biorg. & Med. Chem. Lett., vol. 6, No. 22, pp. 2745-2748, (1996).

Augeri, D.J. et al., "Discovery and Preclinical Profile of Saxagliptin (BMS 477118): A Highly Potent, Long-Acting, Orally Active Dipeptidyl Peptidase IV Inhibitor for the Treatment of Type 2 Diabetes", J. Med. Chem., 48, pp. 5025-5037, (2005).

Biller et al., "Isoprenoid (Phosphinylmethyl)phosphonates as Inhibitor of Squalene Synthetase", J. Med. Chem., vol. 31, No. 10, pp. 1869-1871 (1988).

Biller et al., "Squalene Synthetase Inhibitors", Curr. Pharm. Des, 2, pp. 1-40 (1996).

Bryn, S.R., Solid State Chem. Drugs 2nd ed. TOC (1999).

Capson, T.L., "Synthesis and Evaluation of Ammonium Analogs of Carbocationic Intermediates in Squalene Biosynthesis", Dept. Med. Chem. U of Utah, Table of Contents pp. 16, 17, 40-43, 48-51, Summary, (1987).

Corey, E. J. et al, "Application of Unreactive Analogs of Terpenoid Pyrophosphates of Studies of Multistep Biosynthesis. Demonstration That 'Presqualene Pyrophosphate' is Essential Intermediate on the Path to Squalene", J. Amer. Chem. Soc. 98, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Cosier, J. et al., "A Nitrogen-Gas Stream Cryostat for General X-ray Diffraction Studies", J. Appl. Cryst., vol. 19, pp. 105-107 (1986).

Ghiselli, G., "The pharmacological profile of FCE 27677: a novel ACAT inhibitor with potent hypolipdemic activity mediated by selective suppression of the hepatic secretion of ApoB100-containing lipoprotein", Cardiovasc. Drug Rev. 16(1):16-30(1998).

Hara, S., "Ileal Na+/bile acid Contransporter Inhibitors", Drugs of the Future, 24(4), pp. 425-530 (1999).

Hughes, T. E. et al., "(1-R[2-[(5-Cyanopyridin-2-yl)amino]ethyl]amino]acetyl]-2- cyano (S)-pyrrolidine), a Slow-Binding Inhibitor of Dipeptidyl Peptidase IV", Biochem. 38, pp. 11597-11603 (1999).

Johannsson, G. et al., "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Krause, B.R. et al. "ACAT Inhibitors: Physiologic Mechanisms for Hypolipidemic and Anti-Atherosclerotic Activities in Experimental Animals", Inflammation: Mediators and Pathways, CRC Press Inc, publ., Ruffolo, Jr., R.R. et al., eds., pp. 173-198 (1995).

McClard, R.W. et al., "Novel Phosphonylphosphinyl (P-C-P-C) Analogues of Biochemically Interesting Diphosphates. Syntheses and Properties of P-C-P-C Analogues of Isopentenyl Diphosphate and Dimethylallyl Diphosphate", J. Am. Chem. Soc. 109, pp. 5544-5545 (1987).

Mullin, J.W., "Programmed Cooling of Batch Crystallizers", Chem. Eng. Sci, vol. 26, pp. 369-377 (1971).

Morrison, J.F. et al., "The Behavior and Significance of Slow-Binding Enzyme Inhibitors", Advances in Enzymology and Related Areas of Molecular Biology, vol. 61, John Wiley & Sons, Inc., publ., Meister, A., ed., pp. 201-206 (1988).

Murakami, K. et al., "A Novel Insulin Sensitizer Acts as a Coligand for Peroxisome Proliferator-Activated Receptor-a (PPAR-a) and PPAR-y", Diabetes vol. 47, pp. 1841-1847 (1998).

Nicolosi, R.J. et al., "The Acat inhibitor, C1-1011 is effective in the prevention and regression of aortic fatty streak area in hamsters", Atherosclerosis 137(1):77-85 (1998).

Otwinowski, Z. et al., "Processing of X-Ray Diffraction Data Collected in Oscillation Mode", Macromolecular Crystallography, Part A, Methods in Enzymology, vol. 276, Academic Press, publ., Carter, Jr., C.W. et al., eds., pp. 307-326 (1997).

Ortiz de Montellano, P. et al., "Inhibition of Squalene Synthetase by Farnesyl Pyrophosphate Analogues", J. Med. Chem., 20:243-249 (1977).

Rosenblum, S. B. et al., "Discovery of 1-(4-Fluorophenyl)-(3R)43-(4-fluoropheny1)-(35)-hydroxypropyl]-(45)-(4-hydroxypheny1)-2-azetidinone (SCH 58235): A Designed, Potent, Orally Active Inhibitor of Cholesterol Absorption", J. Med. Chem. 41, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-diphenylimidazole ACAT Inhibitor", Bioorganic & Med. Chem. Lett., vol. 6, No. 1, pp. 47-50, (1996).

Stout, et al., "Inhibitors of acyl-CoA:cholesterol 0-acyl transferase (ACAT) as hypocholeserolemic agents. 6. . . . " Chemtracts: Org. Chem., 8(6):359-362 (1995).

Sorbera, L.A. et al., "Treatment of Lipoprotein Disorders ACAT Inhibitor", Drugs of the Future, 24(1), pp. 9-15 (1999).

Yamada, M. et al., "A Potent Dipeptide Inhibitor of Dipeptidyl Peptidase IV", Biorganic & Med. Chem. Lett. 8, pp. 1537-1540 (1998).

H-1 free base DSC

H-1 free base Raman

H2-1 HCl salt DSC

H2-1 HCl salt IR

H.75-3 HCl salt DSC

H.75-3 HCl salt TGA

H0.75-3 HCl salt IR 1.33 HCl Salt Form H1.67-1 PXRD 1.33 HCl Salt, Form H1.67-1, DSC 1.33 HCl Salt, Form H1.67-1, TGA 1.33 HCl Salt, Form H1.67-1, IR H-1 benzoate salt DSC H-1 benzoate salt TGA N-3 free base PXRD N-3 free base DSC N-3 free base TGA

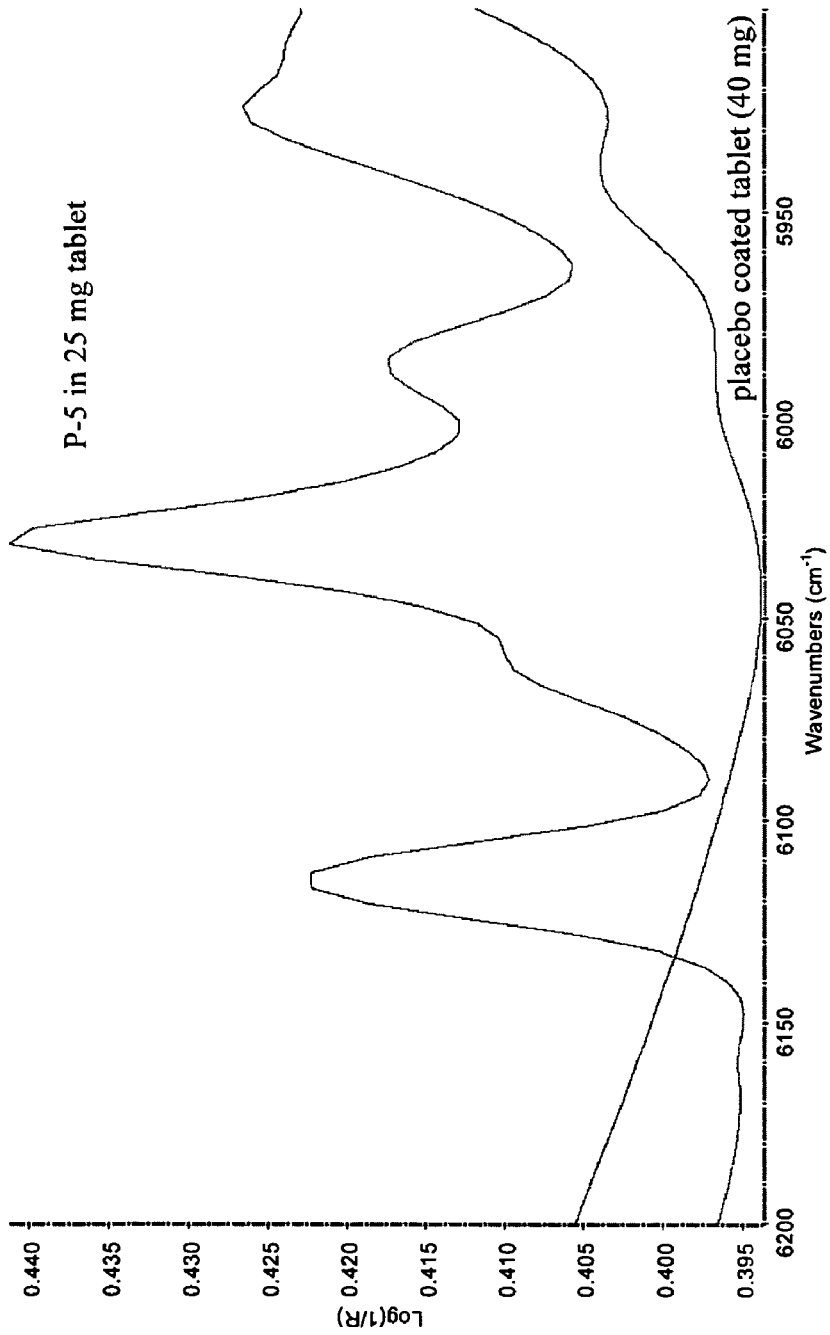

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Synthetic; Primer

<400> SEQUENCE: 1
acgccgacga tgaagaca                                                    18

<210> SEQ ID NO 2

```
<211> LENGTH: 20
<212> TYPE: DNA
<213> ORGANISM: Artificial Sequence
<220> FEATURE:
<223> OTHER INFORMATION: Synthetic; Primer

<400> SEQUENCE: 2
aggtaaagag aaacattgtt                                                   20

<210> SEQ ID NO 3
<211> LENGTH: 19
<212> TYPE: DNA
<213> ORGANISM: Artificial Sequence
<220> FEATURE:
<223> OTHER INFORMATION: Synthetic; Primer

<400> SEQUENCE: 3
ggtaccagcg cagaggctt                                                    19

<210> SEQ ID NO 4
<211> LENGTH: 27
<212> TYPE: DNA
<213> ORGANISM: Artificial Sequence
<220> FEATURE:
<223> OTHER INFORMATION: Synthetic; Primer

<400> SEQUENCE: 4
ctcgagctaa ggtaaagaga aacattg                                           27
```

CRYSTAL FORMS OF SAXAGLIPTIN AND PROCESSES FOR PREPARING SAME

This application is a divisional of U.S. patent application Ser. No. 12/105,316, filed on Apr. 18, 2008 now U.S. Pat. No. 7,943,656, which claims the benefit of U.S. Provisional Application Ser. No. 60/912,950, filed Apr. 20, 2007, the disclosures of which are incorporated herein by reference in its entirety.

FIELD OF THE INVENTION

The present invention relates to polymorphic crystal structures of saxagliptin, pharmaceutical compositions thereof, process for preparing such crystal structures, and methods of treating disorders, such as diabetes, therewith.

BACKGROUND OF THE INVENTION

The compound of the structure

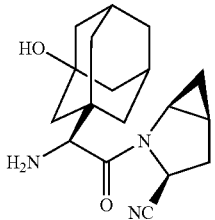

(or its hydrochloride salt, or trifluoroacetic acid salt) (hereinafter the above DPP4-inhibitor or saxagliptin) is an orally active reversible dipeptidyl peptidase-4 (DPP4) inhibitor, which is a therapeutic agent for treatment of Type-2 diabetes mellitus, obesity and related diseases which is disclosed in U.S. Pat. No. 6,395,767, Example 60.

U.S. application Ser. No. 10/716,012 (Publication No. US2005/0090539A1, published Apr. 28, 2005) discloses a process for preparing saxagliptin including the benzoate salt thereof (Scheme VII, Example 41), the free base (Example 42), free base monohydrate thereof (Example 42) and the hydrochloric acid salt thereof (Scheme VIIB, Example 42), the disclosure of which is incorporated herein by reference.

SUMMARY OF THE INVENTION

In accordance with the present invention, there are provided crystal structures of saxagliptin which has the formula I:

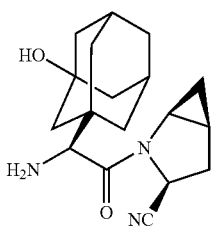

preferably in substantially pure form, including
A. the free base of saxagliptin and hydrates thereof including
(a) the crystalline free base of saxagliptin, which is form N-3, preferably in substantially pure form;
(b) the monohydrate of the free base of saxagliptin containing 1 equivalent $H_2O$, which is form H-1, preferably in substantially pure form; and/or
(c) the hemihydrate of the free base of saxagliptin containing 0.5 equivalent $H_2O$, which is form H.5-2, preferably in substantially pure form.
B. the hydrated hydrochloride salt of saxagliptin which is
(a) the monohydrochloride salt H2-1 form containing 2 equivalents $H_2O$, preferably in substantially pure form;
(b) the monohydrochloride H0.75-3 form containing 0.75 equivalents $H_2O$, preferably in substantially pure form;
(c) the monohydrochloride H1.25-2 form containing 1.25 equivalents $H_2O$, preferably in substantially pure form;
(d) the 1.33 hydrochloride H1.67-1 form containing 1.67 equivalents $H_2O$, preferably in substantially pure form; (composition is 3 drug:4HCl:5$H_2O$)
(e) the dihydrochloride salt form H2-1 containing 2 equivalents $H_2O$, preferably in substantially pure form;
(f) the hydrochloride salt of saxagliptin which is Pattern P-5; or
(g) a mixture of two or more of B.(a), B.(b), B.(c), and/or B(f), preferably a mixture of B.(a), B.(b), and/or B(f), or a mixture of B(a) and B(f), preferably in substantially pure form.
C. the hydrated HBr salt of saxagliptin which is
(a) the H2-1 form containing 2 equivalents $H_2O$, preferably in substantially pure form; and
(b) the H1-2 form (also referred to as form T1H2) containing 1 equivalent $H_2O$, preferably in substantially pure form.
D. the hydrated HI (hydrogen iodide) salt of saxagliptin, which is form H2-1 containing 2 equivalents $H_2O$, preferably in substantially pure form.
E. the hydrated ammonium sulfate ($NH_4SO_4$) salt of saxagliptin which is the H3-1 form containing 3 equivalents $H_2O$, preferably in substantially pure form.
F. the nitrate ($NO_3$) salt of saxagliptin (form N-1), preferably in substantially pure form.
G. the R—H (1:1)-tartrate salt which is form H.5-1 containing 0.5 equivalent $H_2O$, preferably in substantially pure form.
H. the (2:1) fumarate salt of saxagliptin which is form H4-1 containing 4 equivalents $H_2O$, preferably in substantially pure form.
I. the trifluoroacetic acid salt of saxagliptin which is
(a) the trifluoroacetic acid salt form N-1 in substantially pure form;
(b) the hydrated trifluoroacetic acid salt form H2-2 containing 2 equivalents $H_2O$ in substantially pure form; or
(c) the hemihydrated trifluoroacetic acid salt form H.5-1 containing 0.5 equivalent $H_2O$ in substantially pure form.
J. the hydrated benzoate salt of saxagliptin which is form H-1 containing 1 equivalent $H_2O$ of the structure

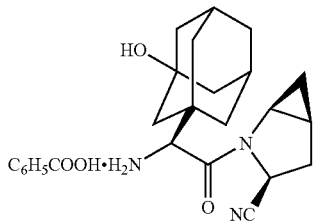

in substantially pure form.

The following Table I sets out the structures for each of the forms A through J (not including A(f)) disclosed above in accordance with the present invention.

TABLE I

| Form Name | | Drug(s) in asymmetric unit | Other compounds in asymmetric unit |
|---|---|---|---|
| H2-1 | | BH$^+$ Cl$^-$ | 2 H$_2$O |
| H0.75-3 | | 2 (BH$^+$ Cl$^-$) | 0.75 H$_2$O |
| H1.25-2 | | 2 (BH$^+$ Cl$^-$) | 1.25 H$_2$O |
| H1.67-1 | * | 3 (BH$^+$ Cl$^-$) | H$_5$O$_2$$^+$ + Cl− + 3 H$_2$O |
| H2-1 | * | (BH$^+$ Cl$^-$) | H$_5$O$_2$$^+$ Cl$^-$ |
| H2-1 | | BH$^+$ Br$^-$ | 2 H$_2$O |
| H1-2 | | BH$^+$Br$^-$ | 1 H$_2$O |
| H2-1 | | BH$^+$ I$^-$ | 2 H$_2$O |
| H3-1 | | (BH$^+$)(NH$_4$$^+$)SO$_4$$^=$ | 3 H$_2$O |
| H4-1 | | 2(BH$^+$) fumarate$^=$ | 4 H$_2$O |
| H.5-1 | | 2(BH$^+$ R-H-tartrate$^-$) | 1 H$_2$O |
| H-1 | | BH$^+$ benzoate$^-$ | 1 H$_2$O |
| N-1 | | BH$^+$ NO$_3$$^-$ | None |
| N-1 | | BH$^+$ TFA$^-$ | None |
| H2-2 | | BH$^+$ TFA$^-$ | 2 H$_2$O |
| H.5-1 | ** | (BH$^+$TFA$^-$) + B | 1 H$_2$O |
| H-1 | | B | 1 H$_2$O |
| H.5-2 | | B | 0.5 H$_2$O |
| N-3 | | 3 B | None |

B = the base = Saxagliptin
* a "hyperacid salt"-more than one HCl per drug
** a "hyperbase salt"- less than one TFA per drug The various crystal structures (or polymorphs) of saxagliptin of the invention described above when in solution will convert to the free base saxagliptin which is disclosed in U.S. Pat. No. 6,395,767.

Any of the crystal structures of saxagliptin of the invention as described above may be employed in various pharmaceutical formulations (as described hereinafter) for use in treating diabetes and related diseases, in accordance with the present invention. Preferred crystal structures of saxagliptin of the invention will be those which can be readily prepared, easy to scale-up, have acceptable shelf-life and are in salt forms generally accepted for use in pharmaceutical formulations. Accordingly, crystalline hydrochloride salts of saxagliptin are generally preferred over other salts such as the HBr salt, HI salt, nitrate salt, trifluoroacetic acid (TFA) salt, benzoate salt, fumarate salt, tartrate salt, ammonium sulfate salt, and nitrate salt.

More preferred is the saxagliptin HCl salt dihydrate form H2-1 alone or in combination with the HCl salt Pattern P-5.

In another embodiment of the present invention, a pharmaceutical composition is provided which includes any of the crystalline forms of saxagliptin of the invention as set out above and a pharmaceutically acceptable carrier therefor.

In another embodiment of the present invention, a process is provided for forming crystalline forms of saxagliptin, including the following crystalline salts of saxagliptin: HCl, HBr, HI, NH$_4$SO$_4$, TFA (trifluoroacetic acid), hemihydrate (form H.5-2) (0.5 equiv. H$_2$O) TFA, NO$_3$, benzoate, (1:1) H-tartrate and (2:1) fumarate, wherein the TFA salt is converted to such crystalline salts through ionic metathesis in water according to the following reaction:

aqueous saxagliptin H$^\oplus$TFA$^-$+R$^\oplus$X$^-$→saxagliptin H$^\oplus$X$^-$+R$^\oplus$TFA$^-$ wherein X$^-$ represents the salt anion.

The above ionic metathesis processes of the invention are summarized below:

| Aqueous Saxagliptin TFA Salt + | | |
|---|---|---|
| R$^\oplus$X$^-$ | Salt Form | Form |
| Na$_2$ tartrate | (1:1)TFA | N-1 |
| KH$_2$PO$_4$ | (1:1)TFA | H2-2 |
| NaCl | HCl | H2-1 |
| KBr | HBr | H2-1 |
| KI | HI | H2-1 |
| (NH$_4$)$_2$SO$_4$ | NH$_4$SO$_4$ | H3-1 |
| Na$_3$ (citrate) or + Na$_2$ (succinate) or + K$_2$HPO$_4$ or + NaF | HemiTFA | H.5-1 |
| KNO$_3$ | NO$_3$ | N-1 |
| Na benzoate | Benzoate | H-1 |
| NaH tartrate | (1:1) H-tartrate | H.5-1 |
| Na$_2$ (fumarate) | (2:1) fumarate | H4-1 |

In carrying out the above-described process of the invention, the saxagliptin TFA salt is dissolved in warm water and the requisite salt as listed above (for example, from about 1 to about 3 fold excess) is added. Crystals of the new salt form upon standing.

In yet another embodiment of the present invention, a process for preparing crystalline saxagliptin in the form of the monohydrate of its free base (form H-1) is provided as described below.

A first process for preparing crystalline saxagliptin in the form of the monohydrate of its free base (form H-1) includes the steps of:

(a) providing the Boc-protected form of saxagliptin having the structure

IA

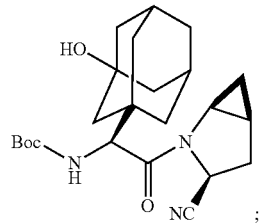

(b) dissolving the protected saxagliptin from step (a) in an organic solvent such as ethyl acetate, isopropyl acetate or methyl tetrahydrofuran preferably ethyl acetate;

(c) reacting the solution from step (b) with a strong mineral acid such as hydrochloric acid, phosphoric acid or sulfuric acid, preferably hydrochloric acid;

(d) if necessary, adding organic solvent such as described in step (b) to the reaction mixture from step (c);

(e) cooling the reaction mixture to a temperature within the range from about 5 to about 35° C., preferably from about 15 to about 25° C.;

(f) treating the cooled mixture from step (e) with base, such as potassium carbonate, potassium bicarbonate, or sodium hydroxide, preferably anhydrous potassium carbonate;

(g) filtering the mixture from step (f) to separate the solids from filtrate;

(h) optionally, washing the solids with organic solvent (as set out in step (b));

(i) collecting and concentrating filtrate;

(j) if necessary, adding water to the filtrate;

(k) agitating the filtrate until crystals form;

(l) optionally, repeating step (j);

(m) optionally, agitating the filtrate; and (n) recovering crystals of saxagliptin free base monohydrate (form H-1) in substantially pure form.

A second process for preparing crystalline saxagliptin in the form of the monohydrate of its free base (form H-1) includes the steps of:

(a) providing the Boc-protected saxagliptin IA;

(b) reacting a mixture of the Boc-protected saxagliptin IA with an organic solvent such as methylene chloride, 1,2-dichloroethane, or chlorobenzene preferably methylene chloride, an alcohol such as methanol, ethanol or isopropanol, preferably methanol, with a strong mineral acid, such as hydrochloric acid, phosphoric acid or sulfuric acid, preferably hydrochloric acid, during which an aqueous phase and an organic phase form;

(c) collecting the aqueous phase;

(d) mixing the aqueous phase with organic solvent such as used in step (b), preferably methylene chloride, water, and then strong base such as an alkali metal base, such as sodium hydroxide or potassium hydroxide, preferably sodium hydroxide, to adjust pH to within the range from about 8.8 to about 10.8, preferably from about 9.0 to about 10.5;

(e) adding sodium chloride to the reaction mixture;

(f) mixing the reaction mixture, whereby an aqueous phase and an organic phase form;

(g) optionally, washing the organic layer with a salt or brine solution such as ammonium chloride brine solution to form an aqueous layer and an organic layer;

(h) treating the organic layer with an organic solvent such as ethyl acetate, isopropyl acetate or methyl tetrahydrofuran, preferably ethyl acetate, while distilling off a portion of organic solvent such as methylene chloride;

(i) filtering the remaining distillation product to remove sodium chloride;

(j) concentrating the filtrate to obtain approximately 1 g saxagliptin per 10 mL of ethyl acetate;

(k) adding water to the mixture from step (j) until crystallization begins;

(l) optionally, adding additional water to form a slurry;

(m) optionally, mixing the slurry;

(n) filtering the slurry;

(o) optionally, washing the resulting wet cake with an organic solvent as defined in step (h), preferably ethyl acetate;

(p) drying the wet cake under vacuum to obtain crystalline saxagliptin in the form of the monohydrate of its free base (form H-1); and (q) recovering the crystalline saxagliptin monohydrate form H-1 in substantially pure form.

In yet another embodiment of the present invention, a third process for preparing crystalline saxagliptin in the form of the monohydrate of its free base (form H-1) is provided which includes the steps of:

(a) providing the Boc-protected form of saxagliptin (IA);

(b) heating the Boc-protected form of saxagliptin (IA) in a water miscible organic solvent such as isopropanol, methanol, or acetonitrile, preferably isopropanol, water and concentrated mineral acid such as hydrochloric acid, phosphoric acid, or methanesulfonic acid, preferably hydrochloric acid, at a temperature within the range from about 55 to about 75° C., preferably from about 60 to about 70° C.;

(c) adding water to the heated mixture;

(d) cooling the mixture from step (c) to a temperature within the range from about 15 to about 35° C., preferably from about 20 to about 30° C.;

(e) adding to the cooled mixture an organic solvent such as methylene chloride, 1,2-dichloroethane or chlorobenzene, preferably methylene chloride, and adjusting the pH of the mixture to within the range from about 8 to about 10, preferably from about 8.5 to about 9.5 (using a base such as an alkali metal hydroxide, for example, sodium hydroxide, or potassium hydroxide preferably sodium hydroxide and potassium carbonate);

(f) dissolving sodium chloride in the pH adjusted solution which forms two phases;

(g) separating the two phases and collecting the rich organic phase;

(h) concentrating the rich organic phase to remove residual water;

(i) cooling the organic phase to a temperature within the range from about 15 to about 35° C., preferably from about 20 to about 30° C.;

(j) adding ethyl acetate or other organic solvent such as isopropyl acetate, or methyl tetrahydrofuran, preferably ethyl acetate, to the cooled mixture;

(k) filtering the resulting solution to remove residual sodium chloride;

(l) adding water to the solution, and upon standing, to form crystals of saxagliptin free base monohydrate; and (m) recovering crystals of saxagliptin free base monohydrate in substantially pure form.

Crystals of saxagliptin free base monohydrate (form H-1) may be recovered in step (l) above according to the following steps:

(a) adding water to the product in step (l);

(b) performing constant volume distillation at less than about 30° C. by adding ethyl acetate at approximately the rate of distillation;

(c) adding water to the mixture from step (b) and cooling to a temperature within the range from about 0 to about 15° C., preferably from about 0 to about 10° C.;

(d) filtering solids from the mixture;

(e) washing the resulting cake with a mixture of organic solvent such as ethyl acetate, isopropyl acetate, or methyl tetrahydrofuran, preferably ethyl acetate, and water;

(f) drying at about 30 to about 50° C., preferably from about 35 to about 45° C. while maintaining the dewpoint about −8° C.; and (g) recovering crystals of the saxagliptin free base (form H-1) monohydrate in substantially pure form.

In still another aspect of the present invention, a process for preparing crystalline saxagliptin in the form of the free base (form N-3) is provided which includes the steps of:

(a) providing saxagliptin in the form of its monohydrate of the free base (that is form H-1);

(b) dissolving the H-1 form of saxagliptin in a suitable organic solvent such as methylene chloride, isopropyl alcohol, or methanol, preferably methylene chloride, or a mixture of one or more thereof such as a mixture of methylene chloride and isopropyl alcohol;

(c) evaporating the resulting solution in step (b) to dryness to form an oil;

(d) dissolving the resulting oil from step (c) in a suitable organic solvent such as ethyl acetate, isopropyl acetate, or methyl tetrahydrofuran, preferably ethyl acetate; and (e) evaporating the resulting solution from step (d) to form a slurry of crystals of the free base of saxagliptin (form N-3).

The slurry of form N-3 free base can be dried, recovered in substantially pure form, and stored under nitrogen to prevent rehydration to the monohydrate H-1 form.

In yet another embodiment of the present invention, a process for preparing crystalline saxagliptin free base in the form of its hemihydrate (form H.5-2) is provided which includes the step of dissolving saxagliptin free base in warm xylene whereby crystals of saxagliptin free base 0.5 hydrate appear upon standing.

In another embodiment of the invention, a process is provided for preparing the crystalline dihydrochloride salt of saxagliptin in the form of its dihydrate which is form H2-1 which includes the steps of:

(a) dissolving the free base monohydrate of saxagliptin (form H-1) in concentrated HCl and dioxane and alcohol such as ethanol; and (b) recovering crystals of the dihydrochloride salt form H2-1 upon standing at room temperature.

In still another embodiment of the invention, a process is provided for preparing the crystalline monohydrochloride salt of saxagliptin in the form of its dihydrate which is form H2-1, which includes the steps of:

(a) providing saxagliptin in the form of its trifluoroacetic acid salt;

(b) dissolving the salt from step (a) in water;

(c) adjusting the pH of the resulting aqueous solution to a pH within the range from about 9 to about 9.8, preferably from about 9.2 to about 9.6 with a strong base such as an alkali metal hydroxide, such as sodium hydroxide or potassium hydroxide, preferably sodium hydroxide, to form an aqueous phase and an organic phase;

(d) treating the resulting solution from step (c) with an organic solvent such as methylene chloride, 1,2-dichloroethane or chlorobenzene, preferably methylene chloride, to extract the aqueous layer from the rich methylene chloride (organic solvent) layer;

(e) adding a solution of hydrochloric acid to the rich organic (methylene chloride) solution;

(f) evaporating the organic (methylene chloride) solution to dryness;

(g) dissolving the resulting solids from step (f) in an alcohol solvent such as ethanol, methanol or isopropanol, preferably ethanol;

(h) heating the alcohol (ethanol) solution from step (g) to a temperature within the range from about 35 to about 60° C., preferably from about 40 to about 50° C.;

(i) adding t-butylmethyl ether (MTBE) or other slurrying agent, such as ethyl acetate or isopropyl acetate, to the heated solution from step (h) to form a slurry;

(j) cooling the resulting slurry;

(k) filtering the slurry;

(l) drying the resulting wet cake to obtain crystals of saxagliptin dihydrate in the form of its hydrochloride salt (form H2-1); and (m) recovering the crystals of saxagliptin dihydrate of its mono HCl salt in substantially pure form.

In yet another embodiment of the invention, a process is provided for preparing the crystalline 1.33 hydrochloride salt of saxagliptin in the form of its hydrate (form H1.67-1) which includes the steps of:

(a) providing the BOC protected compound

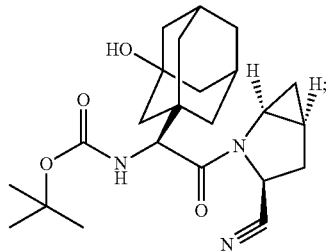

(b) dissolving the BOC protected compound in an organic solvent, preferably ethyl acetate;

(c) reacting the BOC protected compound with hydrochloric acid to form crystals of saxagliptin; and (d) recovering the so-formed crystals of hydrated 1.33 hydrogen chloride salt of saxagliptin, Form H1.67-1.

In another embodiment of the invention, a process is provided for preparing the crystalline hydrochloride salt of saxagliptin in the form of its hydrate (0.75 equivalent $H_2O$) (form H0.75-3) which includes the steps of:

(a) heating the monohydrochloride salt dihydrate (form H2-1) at a temperature from about 25 to about 55° C. for about 1 to about 2 hours; and (b) recovering crystals of the hydrochloride salt form H0.75-3.

In still another embodiment of the present invention, a process for preparing crystalline hydrochloride salt of saxagliptin in the form of its 1.25 hydrate (form H1.25-2) is provided which includes the step of dissolving saxagliptin free base in hydrochloric acid containing about 5 to about 20% methanol, preferably from about 8 to about 12% methanol, whereby crystals of saxagliptin hydrochloride (1.25 equiv. $H_2O$) (form H1.25-2) appear upon standing.

In yet another embodiment of the present invention, a process for preparing crystalline saxagliptin in the form of its tartrate salt containing 1 equivalent of $H_2O$ (form H.5-1) is provided which includes the steps of:

(a) providing saxagliptin in the form of its trifluoroacetic acid salt;

(b) dissolving the salt from step (a) in water;

(c) adjusting the pH of the resulting aqueous solution from step (b) to a pH within the range from about 9 to about 9.8, preferably from about 9.2 to about 9.6, with a strong base, such as an alkali metal hydroxide, for example, sodium hydroxide or potassium hydroxide, preferably sodium hydroxide;

(d) treating the resulting solution from step (c) with an organic solvent such as methylene chloride-1,2-dichloromethane or chlorobenzene, preferably methylene chloride, to extract the rich aqueous layer from the rich organic (methylene chloride) layer;

(e) adding an alcohol such as ethanol, methanol or isopropanol, preferably ethanol, to the rich organic (methylene chloride) solution;

(f) heating the resulting solution from step (e) to a temperature within the range from about 25 to about 45° C., preferably from about 32 to about 40° C.;

(g) treating the resulting heated solution from step (f) with seeds of the tartrate salt of saxagliptin;

(h) separately dissolving L-tartrate in an alcohol solvent such as ethanol, methanol or isopropanol, preferably ethanol;

(i) mixing the resulting tartrate solution with the (seeded) saxagliptin tartrate rich solution from step (g) to form a slurry;

(j) cooling the slurry from step (i); and (k) recovering the crystalline saxagliptin in the form of the tartrate salt, preferably in substantially pure form.

In yet another embodiment of the present invention, a process is provided for preparing the hydrated HBr (hydrogen bromide) salt of saxagliptin which is form H1-2 containing 1 equiv. H$_2$O which includes the steps of heating the H2-1 form of the HBr salt of saxagliptin at a temperature from about 25 to about 55° C. for about 1 to about 2 hours, and recovering crystals of the form H1-2 HBr salt containing 1 equiv. H$_2$O.

In another embodiment of the present invention, a process is provided for preparing the benzoate monohydrate of saxagliptin which is form H-1, which includes the steps of:

(a) providing saxagliptin-trifluoroacetic acid (TFA) salt in D.I. water;

(b) adjusting the pH of the resulting aqueous solution to from about 8.5 to about 9.5, preferably about 9.1 with a strong base such as an alkali metal hydroxide, such as sodium hydroxide or potassium hydroxide, preferably sodium hydroxide, to form an aqueous layer and an organic layer;

(c) extracting the aqueous layer with an organic solvent such as methylene chloride, 1,2-dichloromethane, or chlorobenzene, preferably methylene chloride;

(d) drying the organic (methylene chloride) solution to dryness;

(e) recovering the resulting solid;

(f) dissolving the solid in an alcohol solvent such as ethanol, methanol or isopropanol, preferably ethanol;

(g) adding a solution of benzoic acid preferably in an alcohol solvent such as ethanol, methanol or isopropyl alcohol, preferably ethanol, to the organic (ethanol) solution from step (f) in portions to form a slurry of crystalline material;

(h) optionally, stirring the resulting slurry;

(i) filtering the slurry from step (g) or (h) to recover the wet cake;

(j) optionally, washing the wet cake with alcohol solvent as in step (f), preferably ethanol;

(k) drying the wet cake to obtain crystals of saxagliptin benzoate monohydrate; and (l) recovering crystals of saxagliptin benzoate monohydrate in substantially pure form.

In still another embodiment of the present invention, a process is provided for preparing the hydrochloride salt of saxagliptin which is the Pattern P-5, which includes the steps of:

(a) forming a mixture of the hydrochloride salt of saxagliptin H2-1 form (mono-HCl salt dihydrate) in dry ethanol;

(b) heating the part (a) mixture to a temperature from 40 to 50° C., preferably 45° C., until all H2-1 form dissolves in solution; and (c) cooling the part (b) solution to from 28° C. to room temperature to form crystals of the Pattern P-5.

In addition, in accordance with the present invention, a method is provided for treating diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases (such as scleroderma and multiple sclerosis), various immunomodulatory diseases (such as lupus erythematosis or psoriasis), AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, Syndrome X, dysmetabolic syndrome, diabetic complications, dyslipidemia, hyperinsulinemia, obesity, atherosclerosis and related diseases, as well as inflammatory bowel disease (such as Crohn's disease and ulcerative colitis), wherein a therapeutically effective amount of a crystalline saxagliptin form of the invention (which inhibits DPP4) is administered to a human patient in need of treatment.

The conditions, diseases, and maladies collectively referenced to as "Syndrome X" or Metabolic Syndrome are detailed in Johannsson, *J. Clin. Endocrinol. Metab.*, 82:727-734 (1997).

In addition, in accordance with the present invention, a method is provided for treating diabetes and related diseases as defined above and hereinafter as well as any of the other disease states mentioned above, wherein a therapeutically effective amount of a combination of a crystalline saxagliptin form of the invention and one, two, three or more of other types of antidiabetic agent(s) (which may be employed to treat diabetes and related diseases) and/or one, two or three or more other types of therapeutic agent(s) is administered to a human patient in need of treatment.

Another embodiment of the invention relates to the use of a compound of formula I in the manufacture of a medicament for the treatment of diabetes.

Another embodiment of the invention relates to the compound of formula I of the invention for use in therapy in treating diabetes.

Another embodiment of the invention relates to the compound of formula I of the invention for use in treating diabetes in a mammal Another embodiment of the invention relates to the use of a compound of formula I of the invention in the manufacture of a medicament for treatment of diabetes, in which such treatment comprises a combination with another therapeutic agent, for concurrent or sequential use, in any order.

Another embodiment of the invention relates to the combination of a compound of formula I of the invention and another therapeutic agent as a medicament for the treatment of diabetes.

The term "diabetes and related diseases" refers to Type II diabetes, Type I diabetes, impaired glucose tolerance, obesity, hyperglycemia, Syndrome X, dyslipidemia, dysmetabolic syndrome, diabetic complications, dysmetabolic syndrome, and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than DPP4 inhibitors of a crystalline saxagliptin form of the invention), including the DPP4 inhibitors vildagliptin and sitagliptin, metformin and/or the SGLT-2 inhibitor dapagliflozin disclosed in U.S. Pat. No. 6,515,117, one or more anti-obesity agents, and/or one or more lipid-modulating agents (including anti-atherosclerosis agents), and/or one or more infertility agents, one or more agents for treating polycystic ovary syndrome, one or more agents for treating growth disorders, one or more agents for treating frailty, one or more agents for treating arthritis, one or more agents for preventing allograft rejection in transplantation, one or more agents for treating autoimmune diseases, one or more anti-AIDS agents, one or more anti-osteoporosis agents, one or more agents for treating immunomodulatory diseases, one or more agents for treating chronic inflammatory bowel disease or syndrome and/or one or more agents for treating anorexia nervosa, which are described in detail in U.S. Pat. No. 6,395,767.

The term "lipid-modulating" agent as employed herein refers to agents which lower LDL and/or raise HDL and/or lower triglycerides and/or lower total cholesterol and/or other known mechanisms for therapeutically treating lipid disorders.

The term "equiv." or "equivalent(s)" refers to "moles".

In the above methods of the invention, a crystalline saxagliptin form of the invention will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

BRIEF DESCRIPTION OF THE FIGURES

The invention is illustrated by reference to the accompanying drawings described below.

FIG. 30 shows a Fourier-Transform Near Infrared (FT-NIR) spectra of the crystalline saxagliptin HCl salt Pattern P-5 in the coating layer of a saxagliptin tablet (25 mg) and a 40 mg coated placebo tablet.

DETAILED DESCRIPTION OF THE INVENTION

Figure 1:
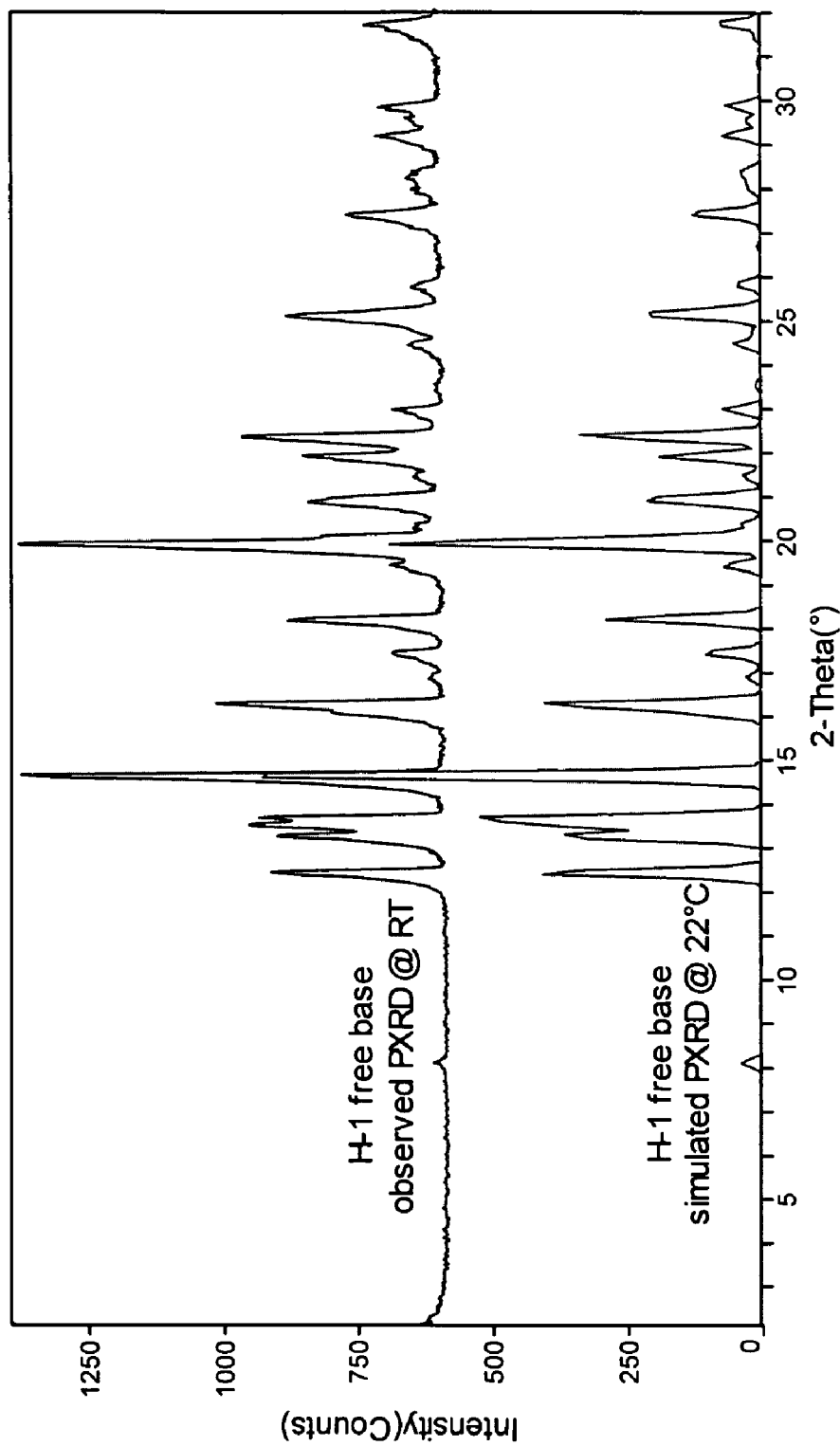
FIG. 1 shows calculated (simulated at 22° C.) and observed (experimental at room temperature) powder X-ray diffraction patterns of the crystalline saxagliptin free base monohydrate (form H-1).

The present invention provides, at least in part, crystalline structures of compound I as a novel material.

The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, the crystalline structures of compound I (saxagliptin) of the invention is in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%.

The ability of a compound to exist in different crystal structures is known as polymorphism. As used herein "polymorph" refers to crystalline forms having the same chemical composition but different spatial arrangements of the molecules, atoms, and/or ions forming the crystal. While polymorphs have the same chemical composition, they differ in packing and geometrical arrangement, and may exhibit different physical properties such as melting point, shape, color, density, hardness, deformability, stability, dissolution, and the like. Depending on their temperature-stability relationship, two polymorphs may be either monotropic or enantiotropic. For a monotropic system, the relative stability between the two solid phases remains unchanged as the temperature is changed. In contrast, in an enantiotropic system there exists a transition temperature at which the stability of the two phases reverse. (Theory and Origin of Polymorphism in "Polymorphism in Pharmaceutical Solids" (1999) ISBN:)-8247-0237).

Samples of the crystalline structures of the invention may be provided with substantially pure phase homogeneity, indicating the presence of a dominant amount of a single crystalline structure and optionally minor amounts of one or more other crystalline structures. The presence of more than one crystalline structure of the invention in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern (observed) with a simulated PXRD pattern (calculated) may indicate more than one crystalline structure in the sample. The simulated PXRD may be calculated from single crystal X-ray data. (see Smith, D. K., "*A FORTRAN Program for Calculating X-Ray Powder Diffraction Patterns*," Lawrence Radiation Laboratory, Livermore, Calif., UCRL-7196, April 1963; see also Yin. S. et al., *American Pharmaceutical Review,* 6(2):80 (2003)). Preferably, the crystalline structure has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline structure of the invention having substantially pure phase homogeneity with less than 1% of the total peak area in the experimentally measured PXRD pattern arising from the extra peaks that are absent from the simulated PXRD pattern.

The various crystalline structures of the invention described herein may be distinguishable from one another through the use of various analytical techniques known to one of ordinary skill in the art. Such techniques include, but are not limited to, solid state nuclear magnetic resonance (SS-NMR) spectroscopy, X-ray powder diffraction (PXRD), differential scanning calorimetry (DSC), thermogravimetric analysis (TGA), infrared spectra (IR), and/or Raman spectra.

Preparation of Crystal Structures

The crystalline structures of the invention may be prepared by a variety of methods as described herein, including for example, crystallization or recrystallization from a suitable solvent, sublimation, growth from a melt, solid state transformation from another phase, crystallization from a supercritical fluid, and jet spraying. Techniques for crystallization or recrystallization of crystalline structures from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (counter solvents) to the solvent mixture. High throughput crystallization techniques may be employed to prepare crystalline structures, including polymorphs.

Crystals of drugs, including polymorphs, methods of preparation, and characterization of drug crystals are discussed in Bryn, S. R. et al., *Solid-State Chemistry of Drugs,* $2^{nd}$ Edition, SSCI, West Lafayette, Ind., publ. (1999).

Seed crystals may be added to any crystallization mixture to promote crystallization. As will be clear to the skilled artisan, seeding is used as a means of controlling growth of a particular crystalline structure or as a means of controlling the particle size distribution of the crystalline product. Accordingly, calculation of the amount of seeds needed depends on the size of the seed available and the desired size of an average product particle as described, for example, in Mullin, J. W. et al., "Programmed cooling of batch crystallizers," *Chemical Engineering Science,* 26:369-377 (1971). In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal structure (i.e., change to amorphous or to another polymorph).

As used herein, the term "room temperature" or "RT" denotes an ambient temperature from 20 to 25° C. (68-77° F.).

Pharmaceutical Compositions and Dosages

The crystalline saxagliptin forms of the invention can be administered for any of the uses herein in the various pharmaceutical compositions and dosage forms and dosages as described in U.S. Pat. No. 6,395,767 which is incorporated herein by reference. Thus, the crystalline saxagliptin forms of the invention can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

A preferred dosage form is the saxagliptin coated tablet disclosed in U.S. application Ser. No. 11/137,068 filed May 25, 2005 which is incorporated herein by reference.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 0.1 mg to about 500 mg of the crystalline form of the invention.

The dose for adults is between 1 and 2,000 mg per day, which can be administered in a single dose or in the form of individual doses from 1-4 times per day. It is preferred that the crystalline dosage form of the invention be administered in a dosage within the range from 2.5 mg to 10 mg per day, which can be administered in a single dose or in the form of individual doses from 1 to 4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

DPP-4 inhibitory activity of the compounds of the present invention may be determined by use of an in vitro assay system which measures the degree in inhibition of DPP-4-mediated cleavage of an appropriate substrate or pseudo-substrate. Inhibition constants (Ki values) for the DPP-4 inhibitors of the invention may be determined by the method described in the experimental section below.

Assays

Cloning, Expression and Purification of Human DPP-4

To generate human DPP-4, PCR (Red-tag polymerase, Sigma) was performed on Human cDNA from placenta (Clontech) using two primers, ACGCCGACGATGAA-GACA (SEQ ID NO: 1) and AGGTAAAGAGAAACAT-TGTT (SEQ ID NO: 2), based on the nucleotide sequence of the human clone (accession number M74777). PCR products were cloned into the pcDN4/HisMax TOPO vector (Invitrogene). For stable transfection of CHO-DG44 cells, DPP4 was rePCRed using primers GGTACCAGCGCAGAGGCTT (SEQ ID NO: 3) and CTCGAGCTAAGGTAAAGAGAAA-CATTG (SEQ ID NO: 4) to generate KpnI and XhoI sites. The KpnI and XhoI sites were used to extract the N-terminal His tagged gene. The His tag, which could be cleaved and removed by Enterokinase, was included to allow purification using the TALON affinity column. The gene was then ligated into the KpnI and XhoI sites of the pD16 vector for stable transfection. Stable cell lines were generated by transfecting the expression vector into Chinese hamster ovary (CHO-DG44) cells using electroporation. The CHO-DG44 cell line was grown in PFCHO media supplemented with HT (glycine, hypoxanthine and thymidine, Invitrogene), glutamine and Recombulin (ICN). Then $1 \times 10^7$ cells/ml were collected, transfected with 60 µg of DNA using electroporation at 300V, and then transferred to a T75 flask. On the third day following transfection, the HT supplement was removed and selection was initiated with methotrexate (MTX, 10 nM, ICN). After a further 10 days the cells were plated into individual wells of 96 well plates. Every 10 days the concentration of MTX was increased two to three fold, up to a maximum of 400 nM. Final stable cell line selection was based on yield and activity of the expressed protein.

An attempt to purify recombinant DPP-4 using Talon resin was not efficient, resulting in small yields, with most of the DPP activity passing through the column. Therefore, protein was further purified using conventional anion exchange (Sepharose Q), gel filtration (S-200) and high resolution MonoQ columns. The final protein yielded a single band on SDS-PAGE gels Amino acid sequence analysis indicated two populations of DPP-4 in the sample. One portion of the protein had 27 amino acids truncated from the N-terminus, while the other was lacking the N-terminal 37 amino acids. This suggests that during isolation the entire transmembrane domain (including His tag) is removed by proteases present in the CHO cells. Total protein concentration was measured using the Bradford dye method and the amount of the active DPP-4 was determined by titrating the enzyme with a previously characterized inhibitor (Ki=0.4 nM). No biphasic behavior was observed during inhibition or catalysis, suggesting that both protein populations are functionally identical.

DPP-4 Inhibition Assays for Saxagliptin and Salts Thereof

Inhibition of human DPP-4 activity was measured under steady-state conditions by following the absorbance increase at 405 nm upon the cleavage of the pseudosubstrate, Gly-Pro-pNA. Assays were performed in 96-well plates using a Thermomax plate reader. Typically reactions contained 100 µl of ATE buffer (100 mM Aces, 52 mM Tris, 52 mM ethanolamine, pH 7.4), 0.45 nM enzyme, either 120 or 1000 µM of substrate (S<Km and S>Km, Km=180 µM) and variable concentration of the inhibitor. To ensure steady-state conditions for slow-binding inhibitors, enzyme was preincubated with the compound for 40 minutes prior to substrate addition, to initiate the reaction. All serial inhibitor dilutions were in DMSO and final solvent concentration did not exceed 1%.

Inhibitor potency was evaluated by fitting inhibition data to the binding isotherm:

$$\frac{vi}{v} = \frac{\text{Range}}{1 + \left(\frac{I}{IC_{50}}\right)^n} + \text{Background} \tag{1}$$

where vi is the initial reaction velocity at different concentrations of inhibitor I; v is the control velocity in the absence of inhibitor, range is the difference between the uninhibited velocity and background; background is the rate of spontaneous substrate hydrolysis in the absent of enzyme, n is the Hill coefficient.

Calculated $IC_{50}$s at each substrate concentration were converted to Ki assuming competitive inhibition according to:

$$Ki = \frac{IC_{50}}{\left(1 + \frac{S}{Km}\right)}  \quad (2)$$

All inhibitors were competitive as judged by a very good agreement of Ki values obtained from the assays at high and low substrate concentrations. In cases where $IC_{50}$ at the low substrate concentration was close to the enzyme concentration used in the assay, the data were fit to the Morrison equation[1], to account for the depletion of the free inhibitor:

$$\frac{vi}{v0} = 1 - \frac{(E+I+IC_{50}) - \sqrt{(E+I+IC_{50})^2 - 4EI}}{2E} \quad (3)$$

where vi and v0 are the steady state velocities measured in the presence and absence of inhibitor, E enzyme concentration.

[1] Morrison, J. F. et al., *Advances in Enzymology*, 61:201-206 (1988).

Each $IC_{50}$ was further refined to Ki, to account for the substrate concentration in the assay using equation (2).

EXAMPLES

The following examples are provided to describe the invention in further detail. These examples, which set forth the best mode presently contemplated for carrying out the invention, are intended to illustrate and not to limit the invention.

The preparation of compounds of formula I is generally described in U.S. Pat. No. 6,395,767, Example 60 and in U.S. Publication US2005/0090539 A1 published Apr. 28, 2005, Schemes VII and VIIB and Examples 41 and 42. U.S. Pat. No. 6,395,767 and U.S. Publication US2005/0090539 A1 are incorporated by reference herein in their entirety.

Example 1

Preparation of Free Base Monohydrate Form of Saxagliptin (Form H-1)

18 g of Boc-protected saxagliptin IA was charged into a three-neck flask equipped with mechanical stirrer, thermocouple, and $N_2$ gas inlet. Ethyl acetate (180 ml) was added to dissolve the Boc-protected saxagliptin. 14.8 ml of 37% hydrochloric acid was added and the mixture agitated at 23° C. for 4 hours at which time the reaction was completed. 180 ml ethyl acetate was added and the reaction flask was cooled to 16° C.

Anhydrous potassium carbonate (60 g) was added to the cooled reaction flask and the resulting mixture was agitated at room temperature for 2 hours. The resulting solid was filtered, the cake washed with 100 ml ethyl acetate, and the filtrate was collected and concentrated to ~61 g. 1 ml water was added dropwise to the filtrate and the mixture was agitated until crystals started to form. Another 1 ml water was added dropwise to the filtrate and the mixture agitated at room temperature for 16 hours. The mixture was filtered and dried to yield 10.5 g of free base monohydrate of saxagliptin (form H-1), yield 77% (purity 99.2 AP).

Example 2

Preparation of Free Base Monohydrate Form of Saxagliptin (Form H-1)

300 g (0.723 mol) of Boc-protected saxagliptin IA (potency 90.6%) was charged into a three-neck 12 L flask equipped with mechanical stirrer, probe, and $N_2$ gas inlet. Methylene chloride (3 L) and methanol (288 ml, 7.23 mol), and 36% HCl (288 ml, 3.5 mol, 4.8 eq) were added. The mixture was stirred for 18 hours and the reaction was completed (the Boc-protected saxagliptin in $CH_2Cl_2$ was <1 mg/ml). The mixture formed two phases; the top aqueous layer was collected (the bottom methylene chloride layer was discarded). Methylene chloride (6 L) and water (720 ml) were added to the recovered aqueous phase. NaOH (5N) (~600 ml) was added dropwise to the recovered aqueous phase to adjust pH to 9.0~10.5. Solid NaCl (120 g) was added and the mixture was agitated for 20 minutes. A phase split occurred and the bottom methylene chloride layer was collected (the top aqueous layer was discarded). The methylene chloride layer was washed with 1% ammonium chloride brine solution (450 ml). A phase split occurred and the bottom methylene chloride layer was collected (the top aqueous layer (pH=7.8) was discarded). Ethyl acetate ~4 L was added while methylene chloride was distilled off at 25° C./50 mm Hg. The distillation was stopped when the final volume reached 2.5 L. The remaining liquid was polish filtered to remove solid NaCl. Concentration was continued to ~1 Kg (~170 g) of free base of saxagliptin monohydrate in 1 L ethyl acetate). Water was added dropwise (17 ml) and the mixture held for ~10 minutes when crystallization started. Another 17 ml of water was added and the resulting slurry was agitated for 30 minutes. The slurry was filtered and the recovered cake washed with ethyl acetate (150 ml). The washed cake was dried at room temperature under vacuum to give 186 g of saxagliptin free base monohydrate (form H-1) yield 81%.

Example 3

Preparation of Free Base Monohydrate Form of Saxagliptin (Form H-1)

A mixture of 1 g Boc-protected saxagliptin (IA), 1 ml isopropanol, 1 ml water and 0.28 ml of concentrated HCl was heated to 65° C. and held at 65° C. for 90 minutes. To the heated mixture was added 2 ml water and the mixture was cooled to 25° C. 12 ml methylene chloride was added and the pH of the mixture was adjusted to ~9 using 0.2 ml 10N sodium hydroxide and 0.4 ml 25% potassium carbonate. 1.25 g sodium chloride was dissolved in the pH adjusted solution. The solution separated into two layers and the rich organic phase was collected.

The rich organic phase was atmospherically concentrated to 3 ml to remove residual water. The concentrated organic was cooled to 25° C., 2 ml ethyl acetate was added and the solution was polish filtered to remove residual sodium chloride. 0.05 ml water was added to the solution which was held for 30 minutes to form a slurry of crystals of product. 0.21 ml water was added to the crystal containing slurry which was subjected to constant volume distillation at less than 30° C. by adding 2 ml ethyl acetate at approximately the rate of distillation. 0.08 ml water was added and the mixture cooled to ~5° C. and held for 30 minutes. The resulting slurry was filtered and the cake washed with a mixture of 2 ml ethyl acetate and 0.04 ml water. The mixture was dried at 40° C. (maintaining the dew point about −8° C.) and the crystals of saxagliptin free base monohydrate recovered.

Example 4

Preparation of Crystalline Saxagliptin in the Form of its Free Base (Form N-3)

The monohydrate of the saxagliptin free base (form H-1) was dissolved in 9 ml methylene chloride and 1 ml isopropyl alcohol (IPA) per gram of saxagliptin monohydrate (form H-1). The resulting solution was evaporated to dryness to form an oil. The oil was dissolved in 10 ml ethyl acetate per gram of saxagliptin monohydrate (form H-1). The resulting solution was evaporated to 3 ml solution per gram of saxagliptin monohydrate (form H-1). The resulting solution was diluted with 10 ml ethyl acetate per gram of saxagliptin monohydrate (form H-1) and then evaporated to 3 ml solution per gram of saxagliptin monohydrate (form H-1) to form a slurry of the free base of saxagliptin (form N-3). If an N-3 slurry did not form, the steps of diluting with ethyl acetate and evaporating were repeated until a slurry formed. The resulting slurry is filtered and dried at 40° C. under a nitrogen sweep to form crystals of the free base of saxagliptin (form N-3). The so-formed crystals were stored under dry nitrogen.

Example 5

Preparation of Crystalline Mono Hydrochloride Salt of Saxagliptin Dihydrate (Form H2-1)

A.

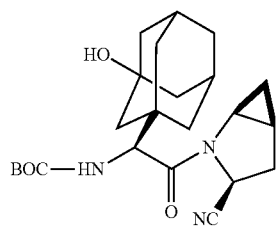

The Part A compound was prepared as described in Publication No. US2005/0090539 A1 published Apr. 28, 2005 as follows: (4.19 g, 10.1 mmol) was dissolved in anhydrous $CH_2Cl_2$ (25 mL) and cooled to 0° C. and treated with trifluoroacetic acid (15 mL) and stirred for 2.5 h at ambient temperature. The solvents were removed by rotary evaporation and the residue was chased with toluene (5 mL) and dried under reduced pressure. Titration with $Et_2O$ afforded the title compound as a white solid (3.92 g, 90%).

B. Preparation of Crystalline MonoHydrochloride Salt of Saxagliptin Dihydrate (Form H2-1)

50 Mg of the trifluoroacetic acid (TFA) salt (potency: 92%) of saxagliptin was dissolved in 0.2 mL water. The pH of the resulting aqueous solution was adjusted to approximately 9.4 with 1N NaOH. Aqueous and organic layers were formed. The aqueous layer was extracted with 2×0.5 mL methylene chloride. The combined rich methylene chloride solution was washed with 1 mL water.

0.116 mL (1 equiv.) of a solution of 1N HCl was added to the rich methylene chloride solution. A clear solution formed which was evaporated to dryness leaving a solid.

0.2 mL of ethanol was mixed with the solid to dissolve the solid. The resulting ethanol solution was heated to 45° C. and 0.3 mL of t-butylmethyl ether was added. The solution turned into a slurry.

The slurry was cooled from 45° C. to 20° C. over one hour. The cooled slurry was filtered and the resulting filter cake was dried at room temperature under vacuum to obtain monohydrochloride salt of saxagliptin dihydrate (form H2-1).

Example 6

Preparation of Crystalline Tartrate Salt of Saxagliptin Containing 1 Equivalent of $H_2O$ (Form H.5-1)

200 Mg of the trifluoroacetic acid (TFA) salt of saxagliptin was dissolved in 4 ml D.I. water. The pH of the resulting aqueous solution was adjusted to approximately 9.4 with 1N NaOH. Aqueous and organic layers formed. The rich aqueous layer was extracted with 3×2 mL methylene chloride. The combined rich methylene chloride solution was washed with 4 ml D.I. water.

2.6 mL ethanol was added to the rich methylene chloride solution and the solution was heated to 35° C. Seeds of the tartrate salt of saxagliptin (0.5 equiv. $H_2O$) (form H.5-1) were added to the heated solution.

1 g L-tartrate was dissolved in ethanol. 326.4 µl of the tartrate solution was added to the product rich solution in 8 portions. A slurry formed. The slurry was cooled from 35° C. to 20° C. over 30 minutes and stirred overnight. The slurry was then filtered and the resulting wet cake dried at 30° C. under vacuum. Crystals of tartrate salt of saxagliptin containing 1 equivalent $H_2O$ (96 mg, yield 39.3 M %) were recovered.

Example 7

Preparation of Crystalline Benzoate Salt of Saxagliptin (Form H-1)

600 Mg of the trifluoroacetic acid (TFA) salt of saxagliptin (potency: 92%) was dissolved in 3 mL D.I. water. The pH of the resulting aqueous solution was adjusted to approximately 9.1 with 1N NaOH. Aqueous and organic layers were formed. The aqueous layer was extracted with 6×6 mL methylene chloride. The combined rich methylene chloride solution was washed with 3 mL D.I. water and the rich methylene chloride solution was dried (Rotavap). The resulting solid was dissolved in 6 mL 190 proof ethanol.

At room temperature, 0.648 mL (1 equiv.) of a solution of benzoic acid in ethanol (conc.=1 g/3 mL) was added to the rich ethanol solution in portions to crystallize and form a slurry of resulting crystalline material.

The resulting slurry was stirred for at least 1 hour, and the slurry was then filtered and the resulting wet cake washed with 3 mL of 190 proof ethanol. The washed wet cake was dried at 30° C. under vacuum overnight to obtain 449.7 mg (yield: 76.8 M %) of saxagliptin benzoate-monohydrate (form H-1).

Example 8

Preparation of Crystalline Salts of HCl, HBr, H$_1$, NH$_4$SO$_4$, TFA, hemiTFA, NO$_3$, Benzoate, 1:1 H-tartrate and (2:1) Fumarate The crystalline TFA salt of saxagliptin was converted to crystalline salts of the title salts through simple ionic metathesis in water as shown by the following equation:

In general, the title salts were prepared by dissolving 10 mg of saxagliptin TFA salt in a minimum amount of warm water. About two-fold excess amount requisite salt for metathesis as listed below was added. Crystals of the new salt of saxagliptin form upon standing. Metathesis failed in some cases (for example, with Na (citrate) or +Na$_2$ (succinate) or +K$_2$HPO$_4$ or +NaF) where novel forms of the TFA salt crystallized instead.

The counterions are:

| Saxagliptin Salt Form | Form | Source/solvents |
|---|---|---|
| (1:1) TFA | N-1 | Na$_2$ tartrate |
| (1:1) TFA | H2-2 | KH$_2$PO$_4$ |
| HCl | H2-1 | NaCl |
| HBr | H2-1 | KBr |
| HI | H2-1 | KI |
| NH$_4$SO$_4$ | H3-1 | (NH$_4$)$_2$SO$_4$ |
| HemiTFA | H.5-1 | Na$_3$ (citrate) or + Na$_2$ (succinate) or + K$_2$HPO$_4$ or + NaF |
| NO$_3$ | N-1 | KNO$_3$ |
| Benzoate | H-1 | Na benzoate |
| (1:1) H-tartrate | H.5-1 | NaH tartrate |
| (2:1) fumarate | H4-1 | Na$_2$ (fumarate) |

Example 9

Preparation of Crystalline 1.33 Hydrochloride Salt of Saxagliptin 1.67 Hydrate (Form H1.67-1)

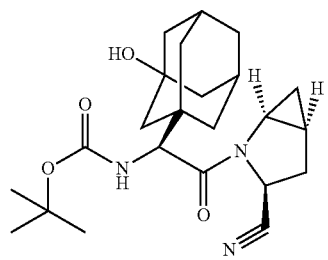

1 equivalent of BOC protected compound and 2 to 16 ml ethyl acetate per gm of the BOC protected compound were mixed with 4 equivalents of concentrated hydrochloric acid (~37%).

The above mixture was stirred at 20 to 25° C. for about 3 hours during which time the BOC protected compound was converted to crystals of hydrated saxagliptin (form H1.67-1).

The so-formed crystals of hydrated saxagliptin were filtered off and washed with ethyl acetate and recovered.

Example 10

Preparation of Crystalline Dihydrochloride Salt of Saxagliptin Dihydrate (Form H2-1)

Saxagliptin monohydrate (form H-1) 80 mg was dissolved in 4M HCl in dioxane (0.2 mL) and a few drops of ethanol.

Crystals of the dihydrochloride salt together with some crystals of the monohydrochloride dihydrate formed upon standing at room temperature.

Example 11

Preparation of Crystalline Hydrochloride Salt of Saxagliptin (Form 0.75-3) Containing 0.75 Equiv. H$_2$O A single crystal of saxagliptin HCl dihydrate (form H2-1) is heated at 50° C. for 2 hours. A single crystal of saxagliptin hydrochloride salt (form 0.75-3) containing 0.75 equiv. H$_2$O form are recovered.

Example 12

Preparation of Crystalline Hydrobromide Salt of Saxagliptin (Form H2-1) Containing 1 Equiv. H$_2$O Saxagliptin dihydrate hydrobromide salt (Form H2-1) is heated at 50° C. for 2 hours. Crystals of saxagliptin hydrobromide salt (form H-1) containing 1 equiv. H$_2$O form are recovered.

Example 13

Preparation of Crystalline Hydrochloride Salt of Saxagliptin (Pattern P-5)

100 mg Saxagliptin mono HCl salt form H2-1 (dihydrate) (prepared employing a procedure similar to that described in Example 5) were added to 2 ml of dry ethanol (dried over molecular sieves). The resulting mixture was heated at 45° C. until all form H2-1 compound was dissolved, at which time heating was discontinued. Crystallization was initiated when the temperature was cooled to 25° C.±2° C. (close to room temperature). Crystals of saxagliptin HCl salt Pattern P-5 were recovered, which crystals were maintained as a slurry in a sealed container at 25° C.±2° C. Crystals stored at ambient conditions underwent significant conversion and were likely the form (close to room temperature) of H2-1.

Crystal Structure Characterization

Crystal structures equivalent to the crystal structures described below and claimed herein may demonstrate similar, yet non-identical, analytical characteristics within a reasonable range of error, depending on test conditions, purity, equipment and other common variables known to those skilled in the art.

Accordingly, it will be apparent to those skilled in the art that various modifications and variations can be made in the present invention without departing from the scope and sprit of the invention. Other embodiments of the invention will be apparent to those skilled in the art from consideration of the specification and practice of the invention disclosed herein. Applicants intend that the specification and examples be considered as exemplary, but not limiting in scope.

X-Ray Powder Diffraction

One of ordinary skill in the art will appreciate that a powder X-ray diffraction pattern may be obtained with a measurement error that is dependent upon the measurement conditions employed. In particular, it is generally known that intensities in an X-ray powder diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional powder X-ray powder diffraction pattern is typically about 5% or less, and such degree of measurement error should be taken into account as pertaining to the aforementioned diffraction angles. Consequently, it is to be understood that the crystal structures of the instant invention are not limited to the crystal structures that provide X-ray diffraction patterns completely identical to the X-ray powder diffraction patterns depicted in the accompanying Figures disclosed herein. Any crystal structures that provide powder X-ray diffraction patterns substantially identical to those disclosed in the accompanying Figures fall within the scope of the present invention. The ability to ascertain substantial identities of X-ray powder diffraction patterns is within the purview of one of ordinary skill in the art.

Saxagliptin Free Base Monohydrate (1 equiv. $H_2O$) (Form H-1), Saxagliptin Mono HCl Salt $2H_2O$ (Form H2-1), Saxagliptin HCl Salt (0.75 equiv. $H_2O$) (Form H0.75-3), Saxagliptin 1.33HCl Salt (1.67 equiv. $H_2O$) (Form H1.67-1), Saxagliptin DiHCl Salt (2 equiv. $H_2O$) (Form H2-1), Saxagliptin Nitrate Salt (Form N-1), Saxagliptin Benzoate Salt (1 equiv. $H_2O$) (Form H-1), Saxagliptin Free Base (Form N-3), and Saxagliptin Mono Hydrochloride Salt (Pattern P-5).

About 200 mg of test sample were packed into a Philips powder X-ray diffraction (PXRD) sample holder. The sample was transferred to a Philips MPD unit (45 KV, 40 mA, Cu $K\alpha_1$). Data were collected at room temperature in the 2 to 32 2-theta rage (continuous scanning mode, scanning rate 0.03 degrees/sec., auto divergence and anti scatter slits, receiving slit: 0.2 mm, sample spinner: ON).

Powder X-ray diffraction patterns for the saxagliptin free base monohydrate (form H-1), saxagliptin mono HCl salt (form H2-1), saxagliptin HCl salt (form H0.75-3), saxagliptin HCl salt (form H1.67-1), salt saxagliptin nitrate salt (form N-1), saxagliptin benzoate salt (form H-1), saxagliptin free base (form N-3) and saxagliptin HCl salt (Pattern P-5) structures are illustrated in FIGS. 1, 6, 11, 16, 21, 22 and 25, and 28 and 29, respectively. Selected diffraction peak positions (degrees 2θ±0.2) for the saxagliptin structures (other than forms N-3 and P-5) set out in the above subtitle are shown in Table A below. Characteristic diffraction peak positions (degrees 2θ±0.1) at RT, are based on a high quality pattern collected with a diffractometer (CuKα) with a spinning capillary with 2θ calibrated with a National Institute of Standards and Technology (NIST) methodology, and other suitable standard known to those skilled in the art. The relative intensities, however, may change depending on the crystal size and morphology.

TABLE A

Selected characteristic diffraction peak positions (degrees 2θ ± 0.1) at RT, based on a high quality pattern collected with a diffractometer (CuKα) with a spinning capillary with 2θ calibrated with a NIST other suitable standard.

| H-1 free base monohydrate | N-3 free base | H-1 benzoate salt | H.75-3 HCl salt | H2-1 mono HCl salt | 1.33 HCl salt (Form H1.67-1) | DiHCl salt (Form H2-1) | N-1 nitrate salt |
|---|---|---|---|---|---|---|---|
| 12.4 | 5.2 | 6.6 | 5.0 | 6.8 | 5.4 | 7.2 | 5.5 |
| 13.3 | 7.9 | 8.3 | 7.0 | 11.1 | 7.0 | 8.6 | 7.0 |
| 13.6 | 10.8 | 15.3 | 8.1 | 13.7 | 13.8 | 11.6 | 11.1 |
| 14.7 | 11.5 | 16.1 | 11.4 | 14.6 | 14.2 | 14.3 | 14.4 |
| 16.2 | 13.0 | 16.9 | 13.4 | 15.2 | 14.6 | 15.7 | 15.1 |
| 18.2 | 14.6 | 17.5 | 14.0 | 16.4 | 16.1 | 19.5 | 15.7 |
| 19.9 | 15.6 | 17.8 | 14.5 | 17.0 | 16.6 | 22.5 | 16.4 |
| 20.9 | 15.9 | 18.6 | 18.6 | 20.2 | 18.6 |  | 16.8 |
| 21.9 | 16.5 | 21.3 | 19.4 | 21.1 | 19.0 |  | 19.6 |
| 22.4 |  |  | 20.0 |  | 20.3 |  |  |

Characteristic diffraction peak positions (degrees 2θ±0.1)@ RT (FIG. 28) based on a high quality pattern collected with a diffractometer (CuKα) with a spinning capillary with 2θ calibrated with a NIST other suitable standard, of saxagliptin HCl salt Pattern P-5 are set out below in Table A'.

TABLE A'

| HCl Salt P-5 Material |
|---|
| 6.2 |
| 10.7 |
| 14.5 |
| 15.0 |
| 15.6 |
| 16.2 |
| 18.1 |
| 18.7 |
| 21.1 |

Hybrid PXRD Patterns

"Hybrid" simulated powder X-ray patterns shown in FIGS. 1, 6, 11, 16, 21, 22 and 25 were generated as described in the literature (Yin. S. et al., *American Pharmaceutical Review*, 6(2):80 (2003)). The room temperature cell parameters were obtained by performing a cell refinement using the CellRefine.xls program. Input to the program includes the 2-theta position of ca. 10 reflections, obtained from the experimental room temperature powder pattern; the corresponding Miller indices, hkl, were assigned based on the single-crystal data collected at low temperature. A new (hybrid) PXRD was calculated (by either of the software programs, Alex or LatticeView) by inserting the molecular structure determined at low temperature into the room temperature cell obtained in the first step of the procedure. The molecules are inserted in a manner that retains the size and shape of the molecule and the position of the molecules with respect to the cell origin, but, allows intermolecular distances to expand with the cell.

PXRD (GADDS-NB)

X-ray powder diffraction (PXRD) data for the saxagliptin free base (neat) form N-3 were obtained using a Bruker C2 GADDS. The radiation was Cu Kα (40 KV, 50 mA). The sample-detector distance was 15 cm. Powder samples were placed in sealed glass capillaries of 1 mm or less in diameter; the capillary was rotated during data collection. Data were collected for 3≦2θ≦35° with a sample exposure time of at least 2000 seconds. The resulting two-dimensional diffraction arcs were integrated to create a traditional 1-dimensional PXRD pattern with a step size of 0.02 degrees 2θ in the range of 3 to 35 degrees 2θ.

Figure 25:
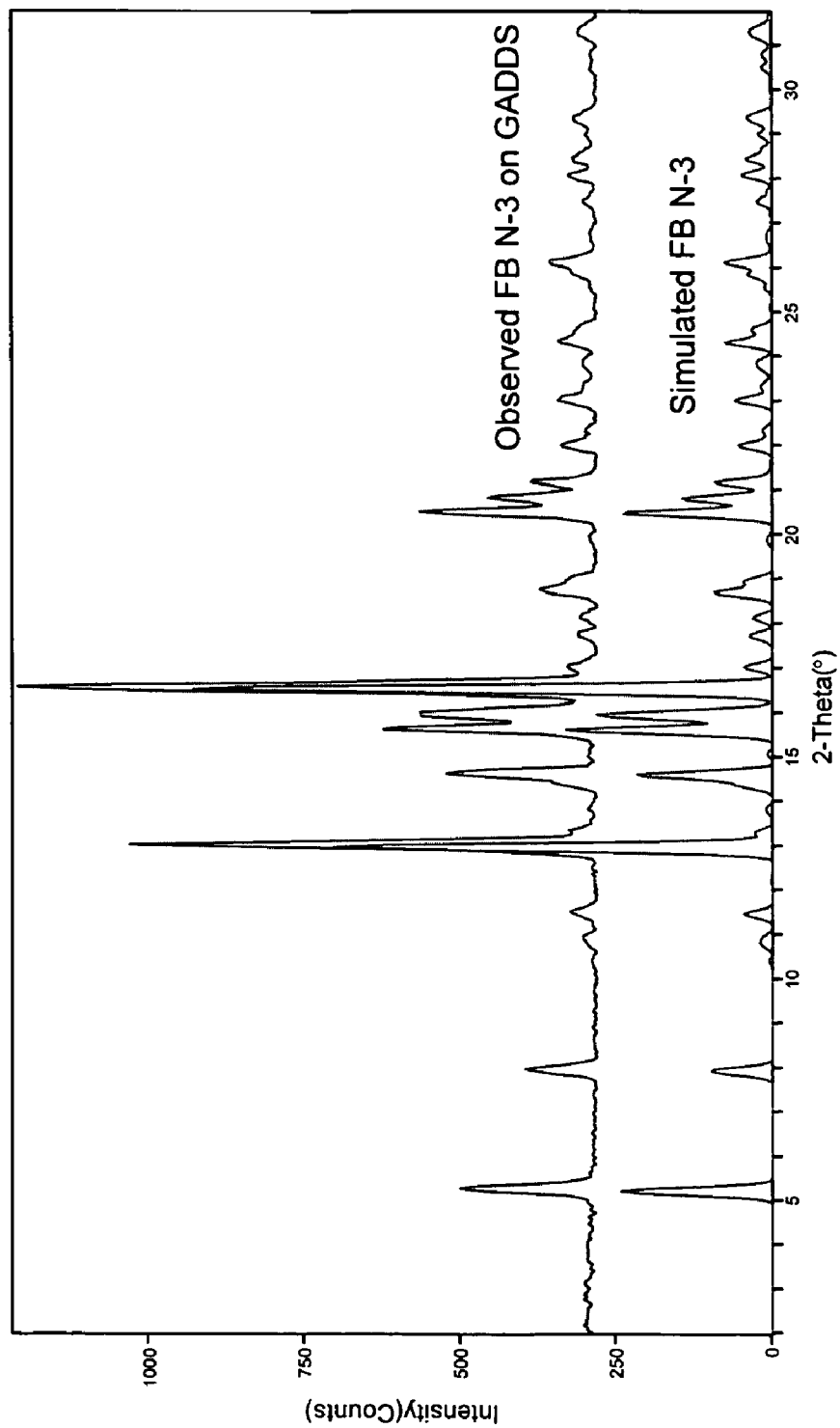
FIG. 25 shows calculated (simulated at room temperature) and observed (experimental at room temperature) powder X-ray diffraction patterns of the crystalline saxagliptin free base (neat) (form N-3).

Powder X-ray diffraction patterns (observed and simulated) for free base form N-3 are shown in FIG. 25.

Thermal Gravimetric Analysis

Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 200° C. for the HCl salt H2-1 between room temperature and 300° C. for the free base monohydrate H-1 and the benzoate salt H-1, and between room temperature and 350° C. for the HCl salt H0.75-3, at 10° C./min heating rate.

TGA curves for the free base monohydrate (form H-1), HCl salt (form H2-1), HCl salt (form H0.75-3), 1.33HCl salt (form H1.67-1), benzoate salt (form H-1), and free base (form N-3) structures are shown in FIGS. 3, 8, 13, 18, 24 and 27, respectively. Weight loss corresponds to one mole of water and one mole of propylene glycol per mole of structure analyzed.

Figure 3:
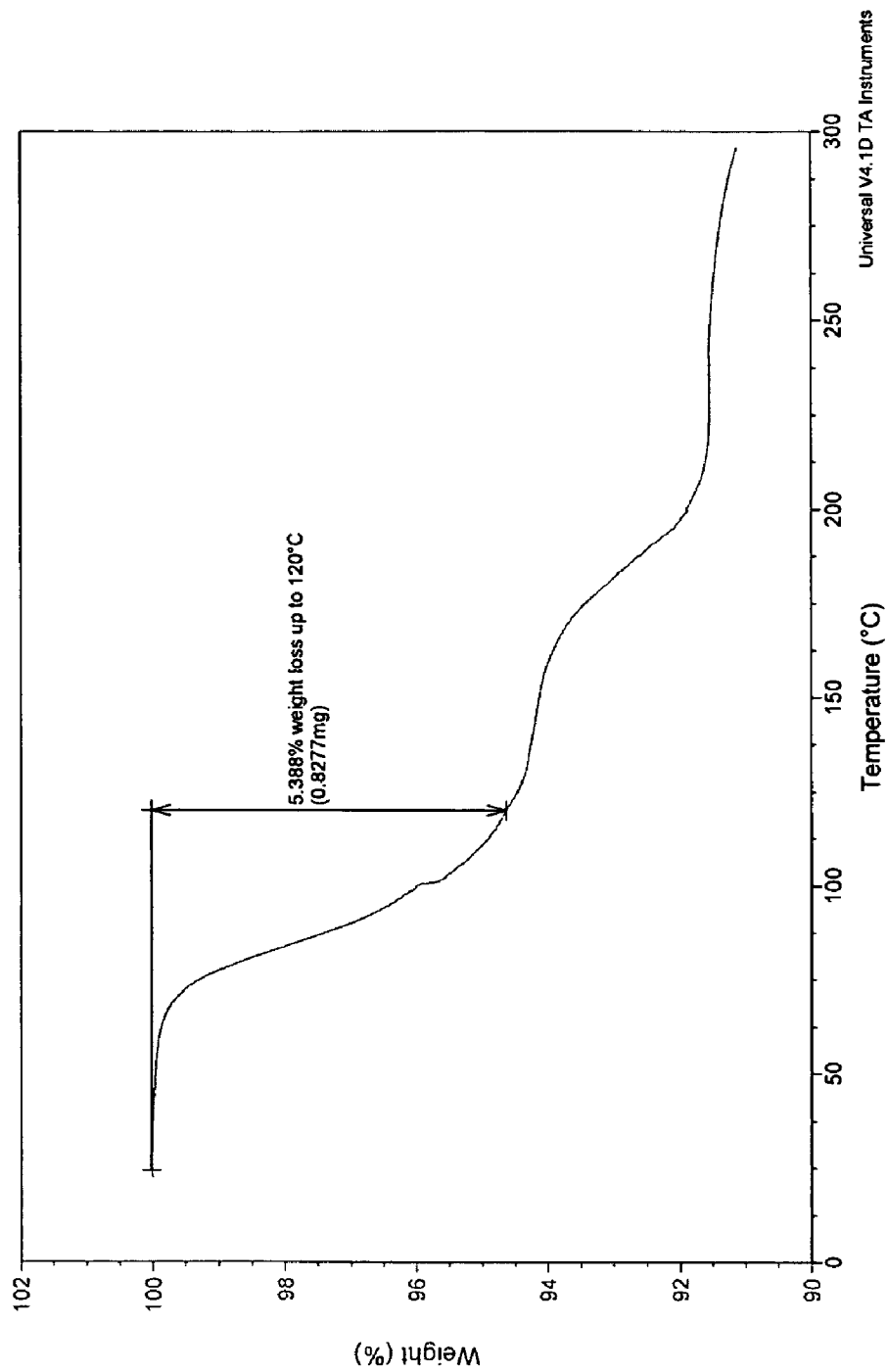
FIG. 3 shows a thermogravimetric analysis (TGA) curve of the crystalline saxagliptin free base monohydrate (form H-1).
Figure 4:
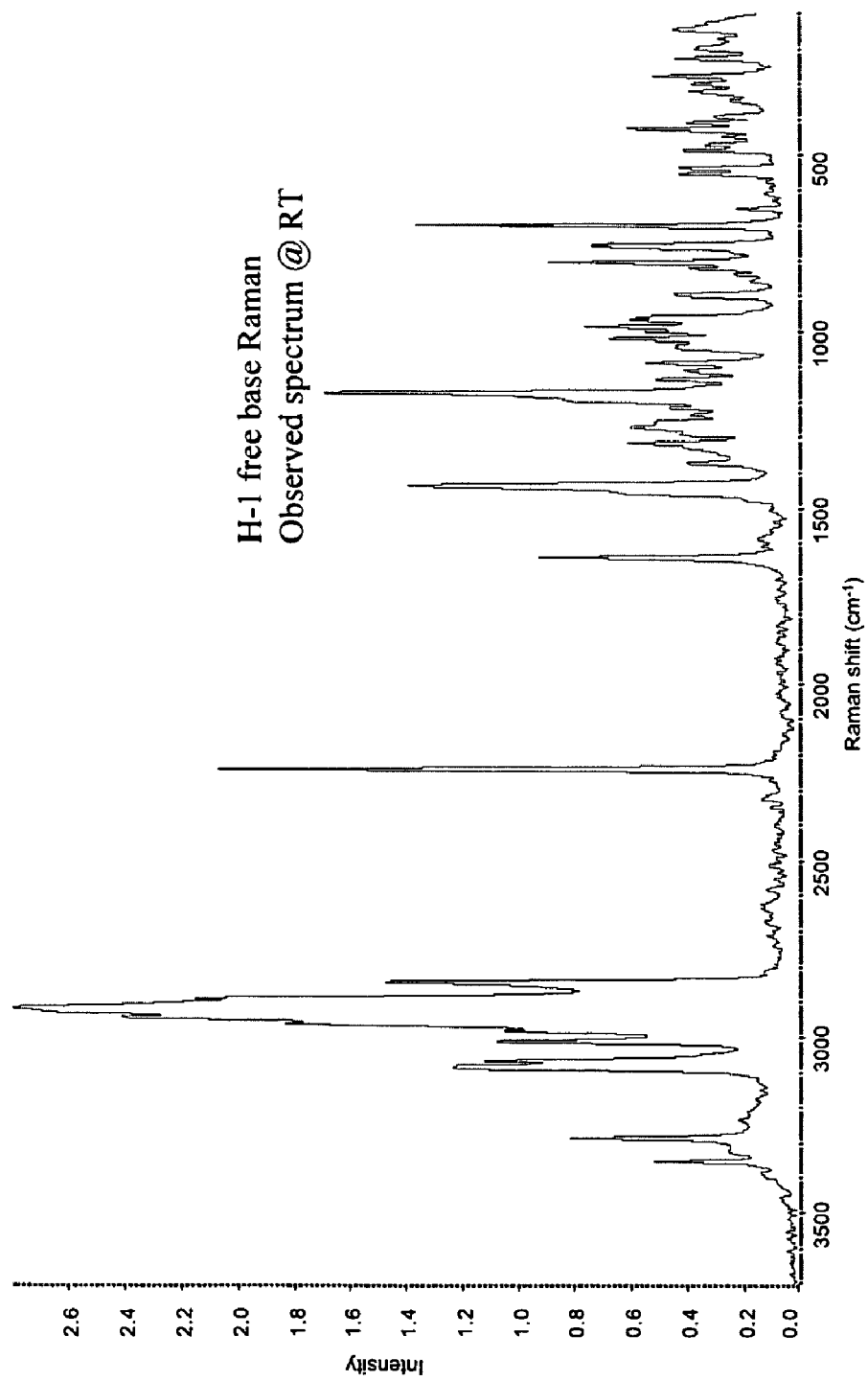
FIG. 4 shows an observed Raman spectrum at room temperature of the crystalline saxagliptin free base monohydrate (form H-1).
Figure 5:
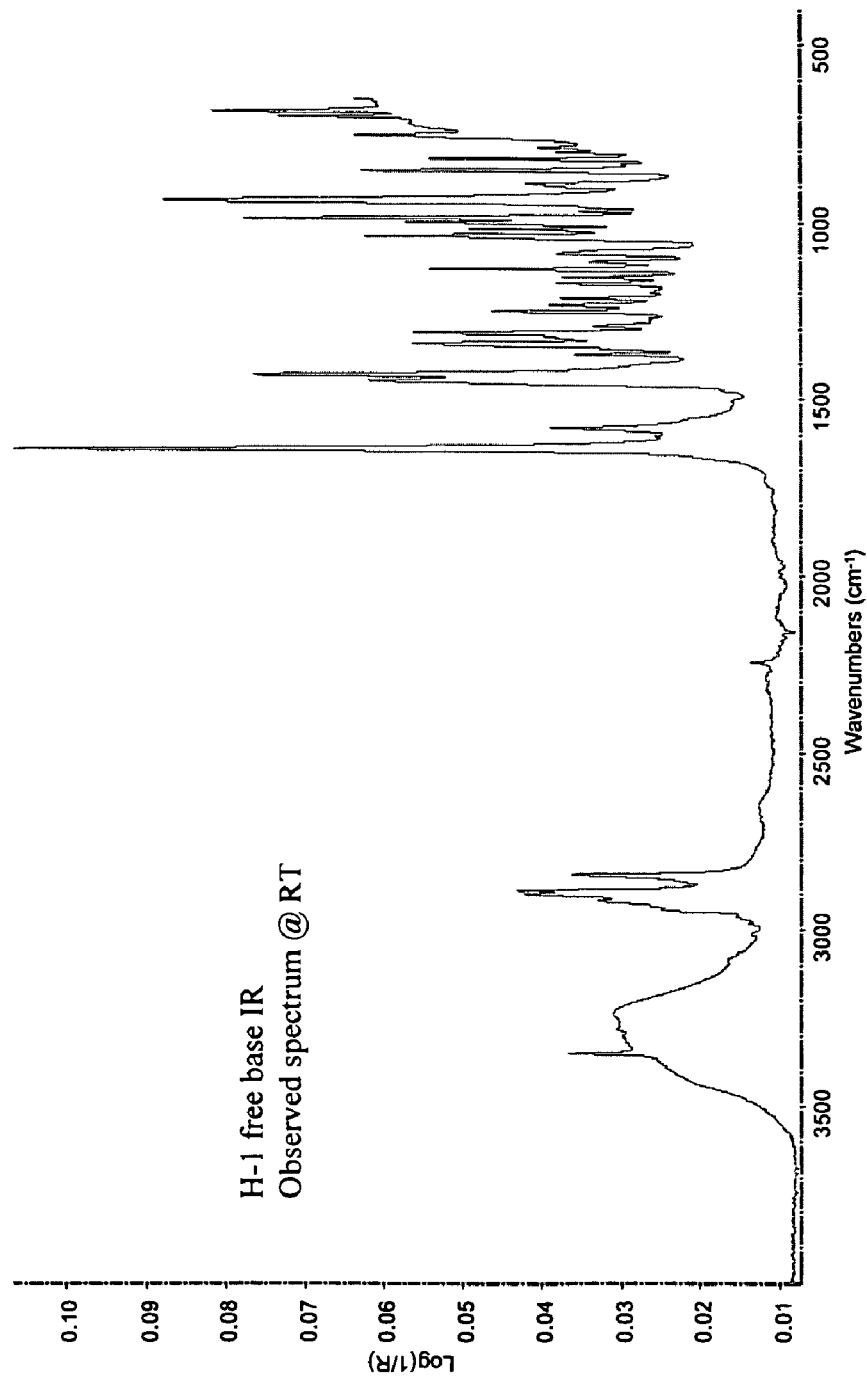
FIG. 5 shows an observed IR spectrum at room temperature of the crystalline saxagliptin free base monohydrate (form H-1).

As seen in FIG. 3, the free base monohydrate (form H-1) had a TGA weight loss of about 5.4% up to about 120° C.

It was also observed that the free base monohydrate (form H-1) had a 0.1% weight gain in the range 25-75% RH at 25° C. and thus is non-hygroscopic.

Figure 8:
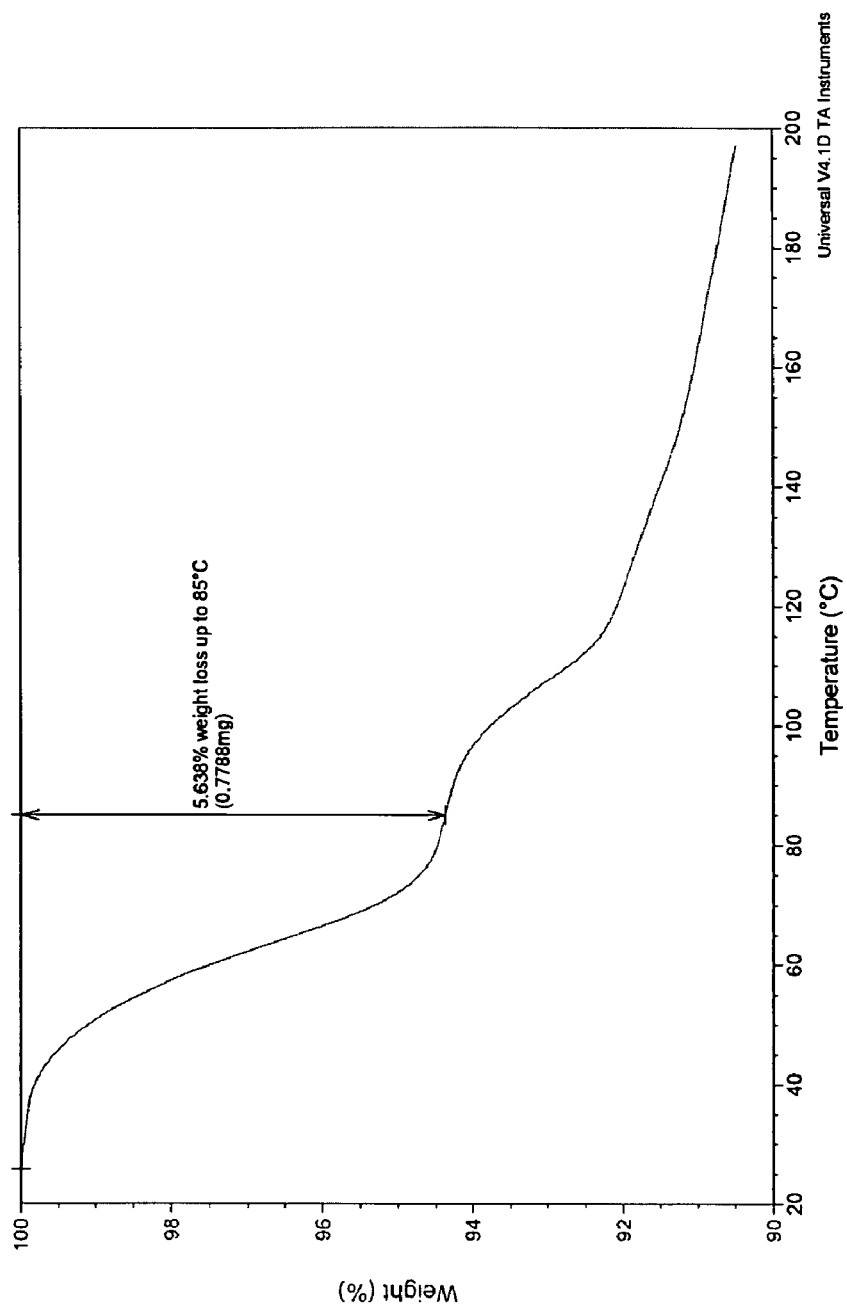
FIG. 8 shows a thermogravimetric analysis (TGA) curve of the crystalline saxagliptin mono HCl salt (2 equiv. $H_2O$) (form H2-1).
Figure 9:
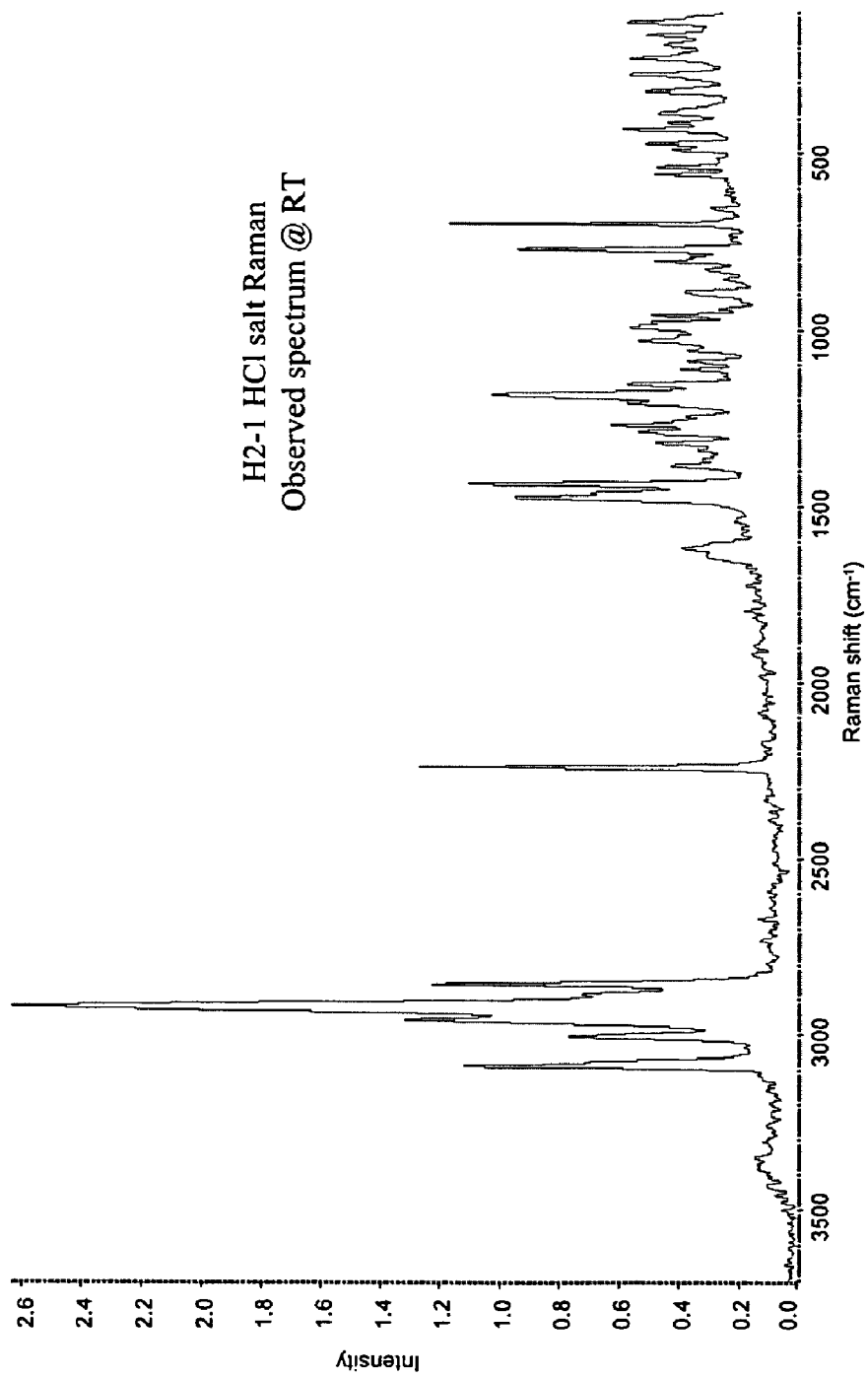
FIG. 9 shows an observed Raman spectrum at room temperature of the crystalline saxagliptin HCl salt (2 equiv. $H_2O$) (form H2-1).
Figure 10:
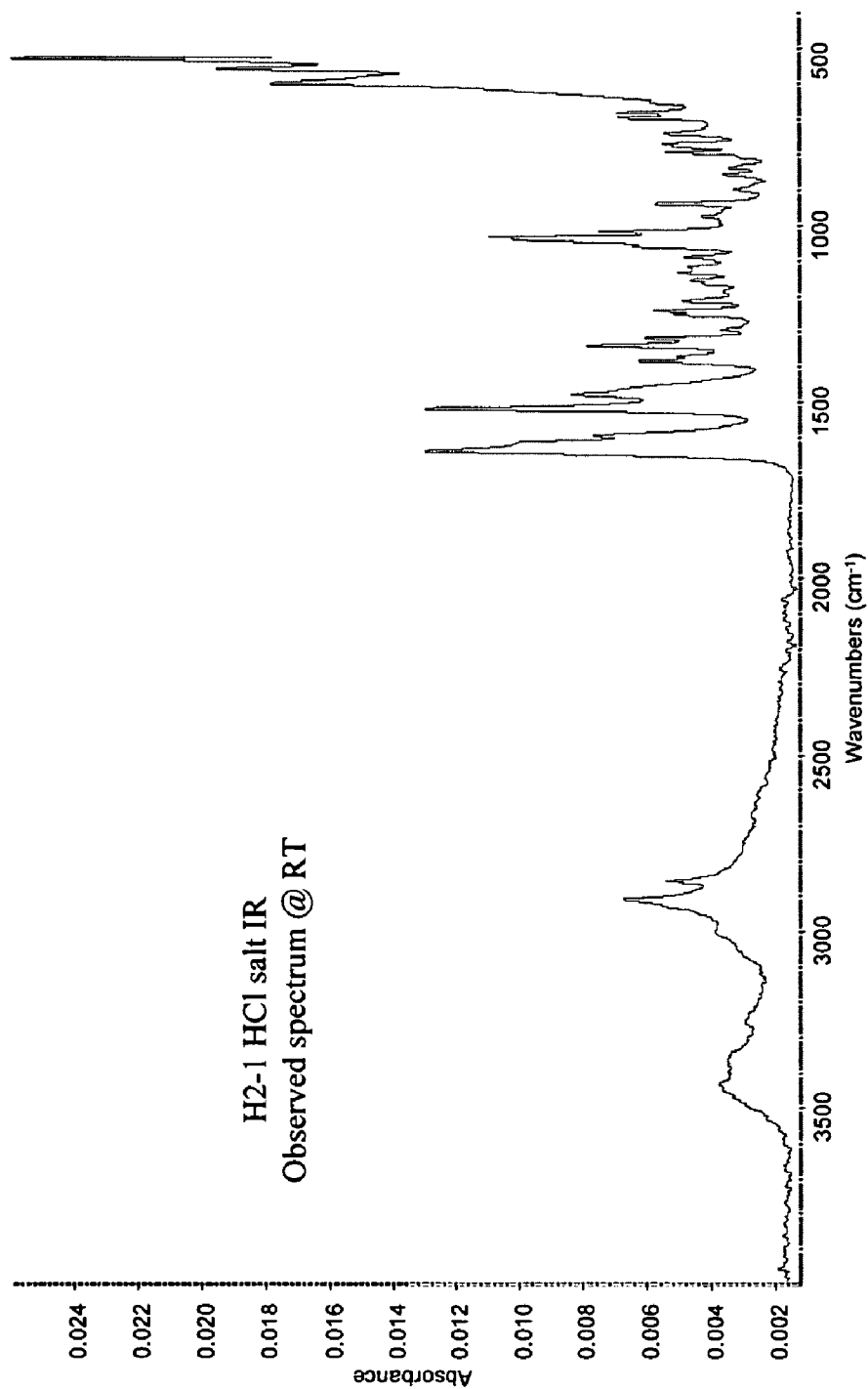
FIG. 10 shows an observed IR spectrum at room temperature of the crystalline saxagliptin HCl salt (2 equiv. $H_2O$) (form H2-1).

As seen in FIG. 8, the HCl salt (form H2-1) had a TGA weight loss of about 5.6% up to about 85° C.

Figure 13:
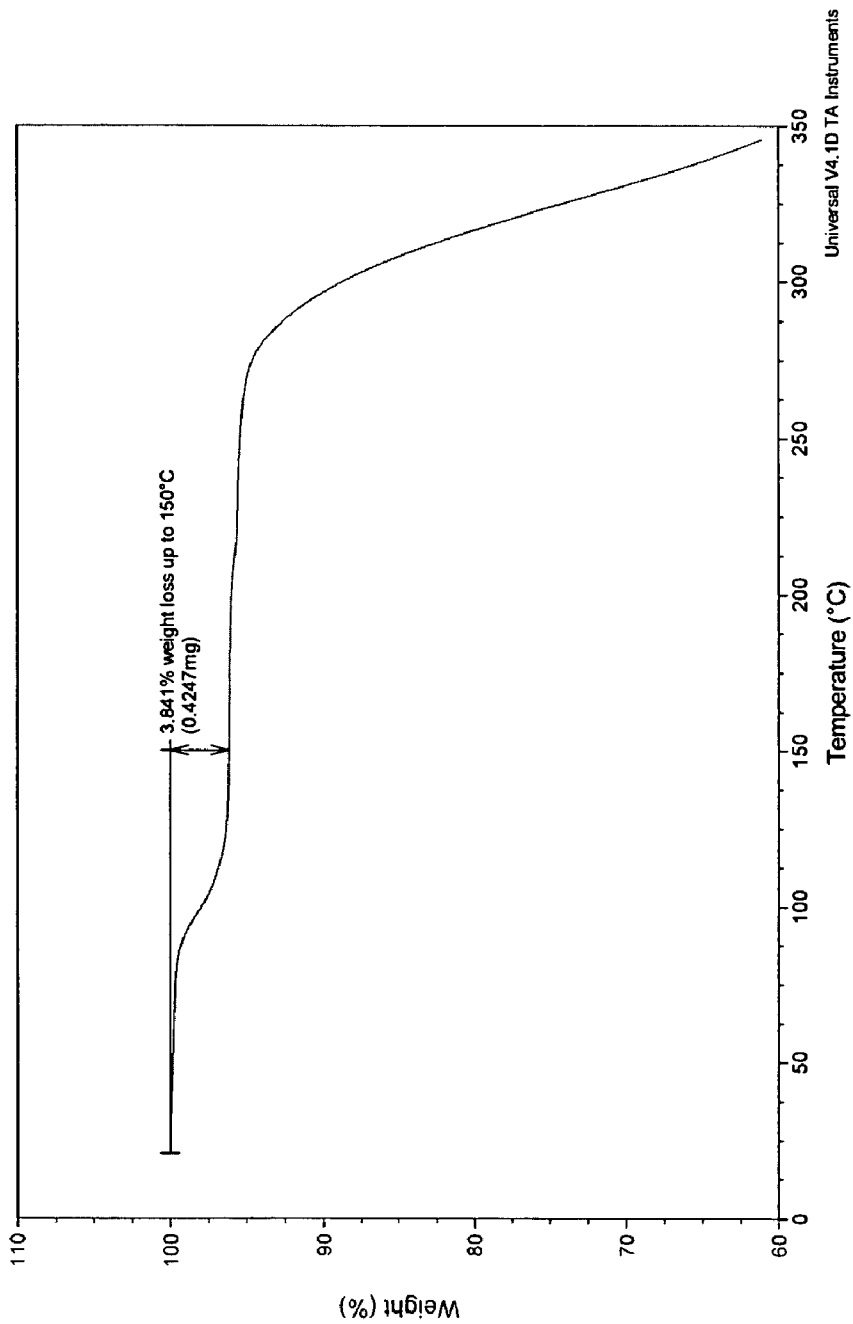
FIG. 13 shows a thermogravimetric analysis (TGA) curve of the crystalline saxagliptin HCl salt (0.75 equiv. $H_2O$) (form H0.75-3).
Figure 14:
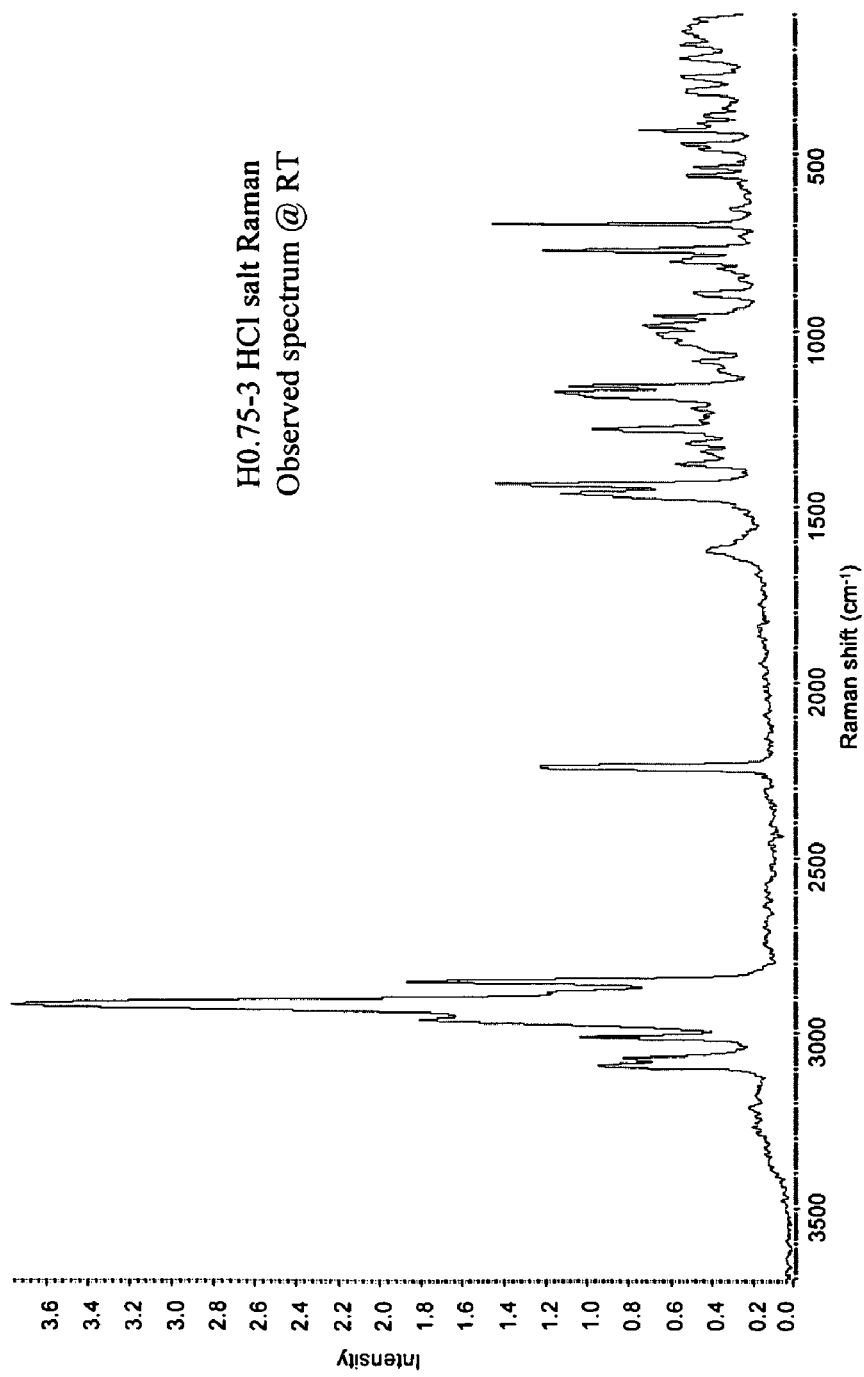
FIG. 14 shows an observed Raman spectrum at room temperature of the crystalline saxagliptin HCl salt (0.75 equiv. $H_2O$) (form H0.75-3).
Figure 15:
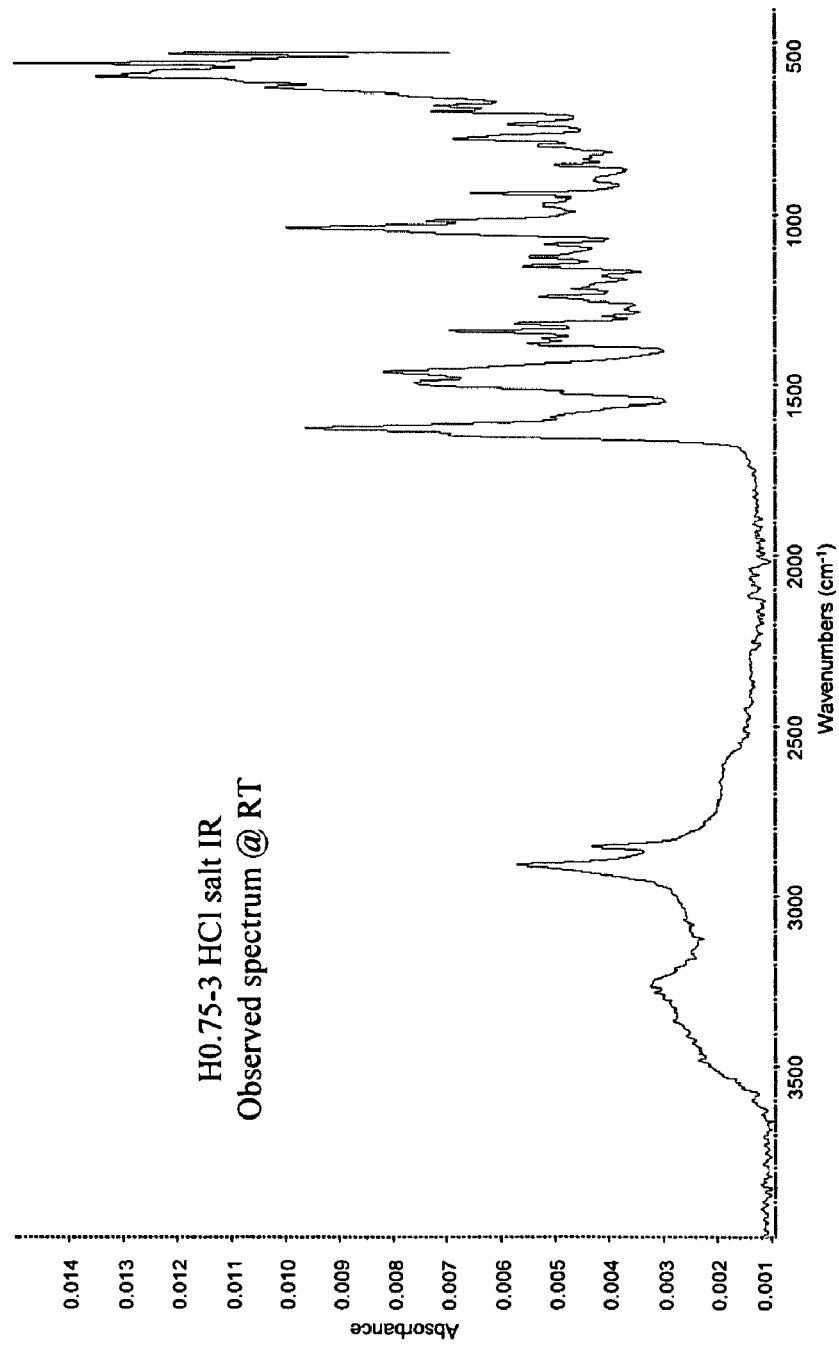
FIG. 15 shows an observed IR spectrum at room temperature of the crystalline saxagliptin HCl salt (0.75 equiv. $H_2O$) (form H0.75-3).

As seen in FIG. 13, the HCl salt (form H0.75-3) had a TGA weight loss of about 4% up to about 120° C.

Figure 18:
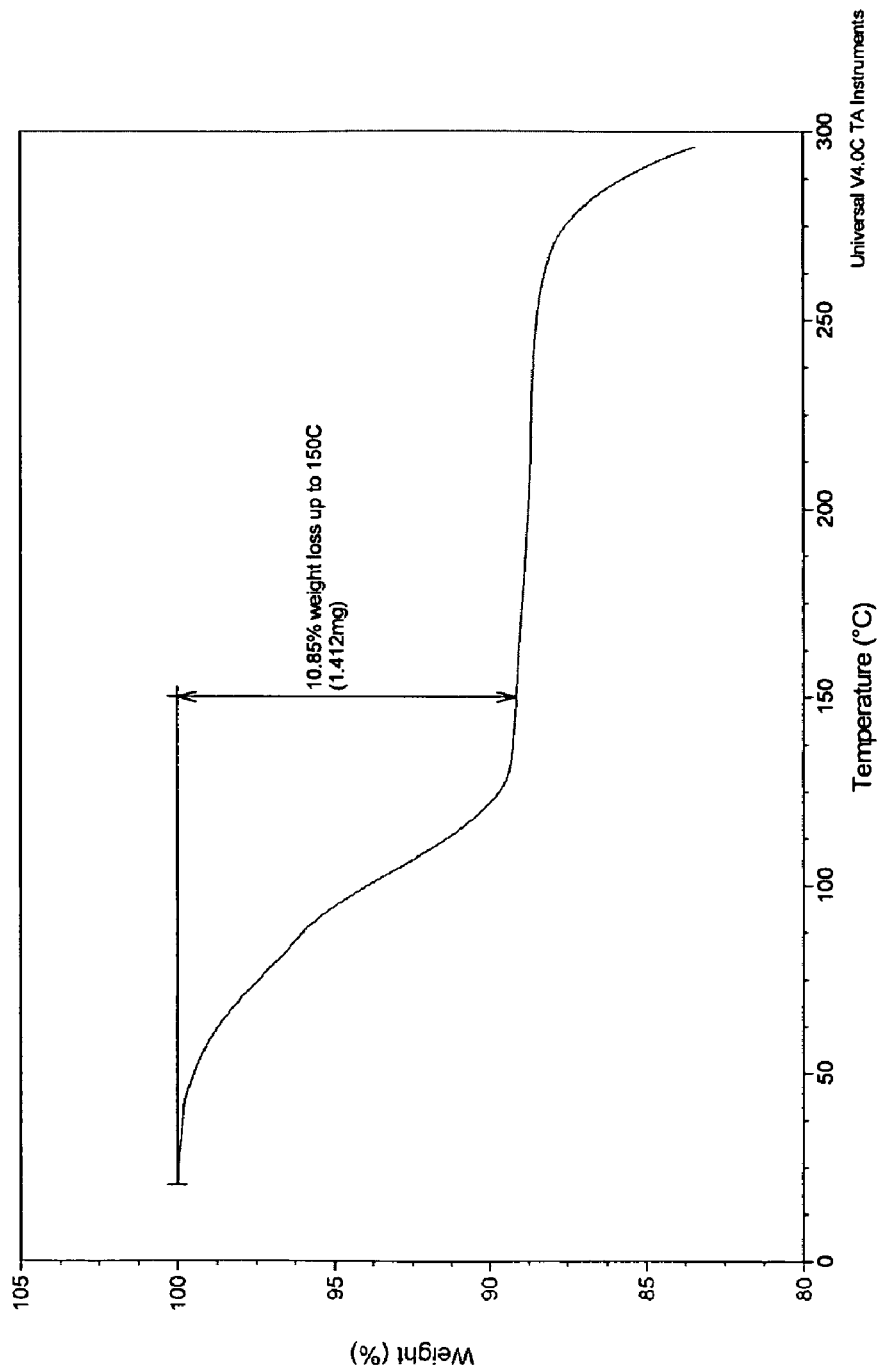
FIG. 18 shows a thermogravimetric analysis (TGA) curve of the crystalline saxagliptin 1.33HCl salt (1.67 equiv. $H_2O$) (form H1.67-1).
Figure 19:
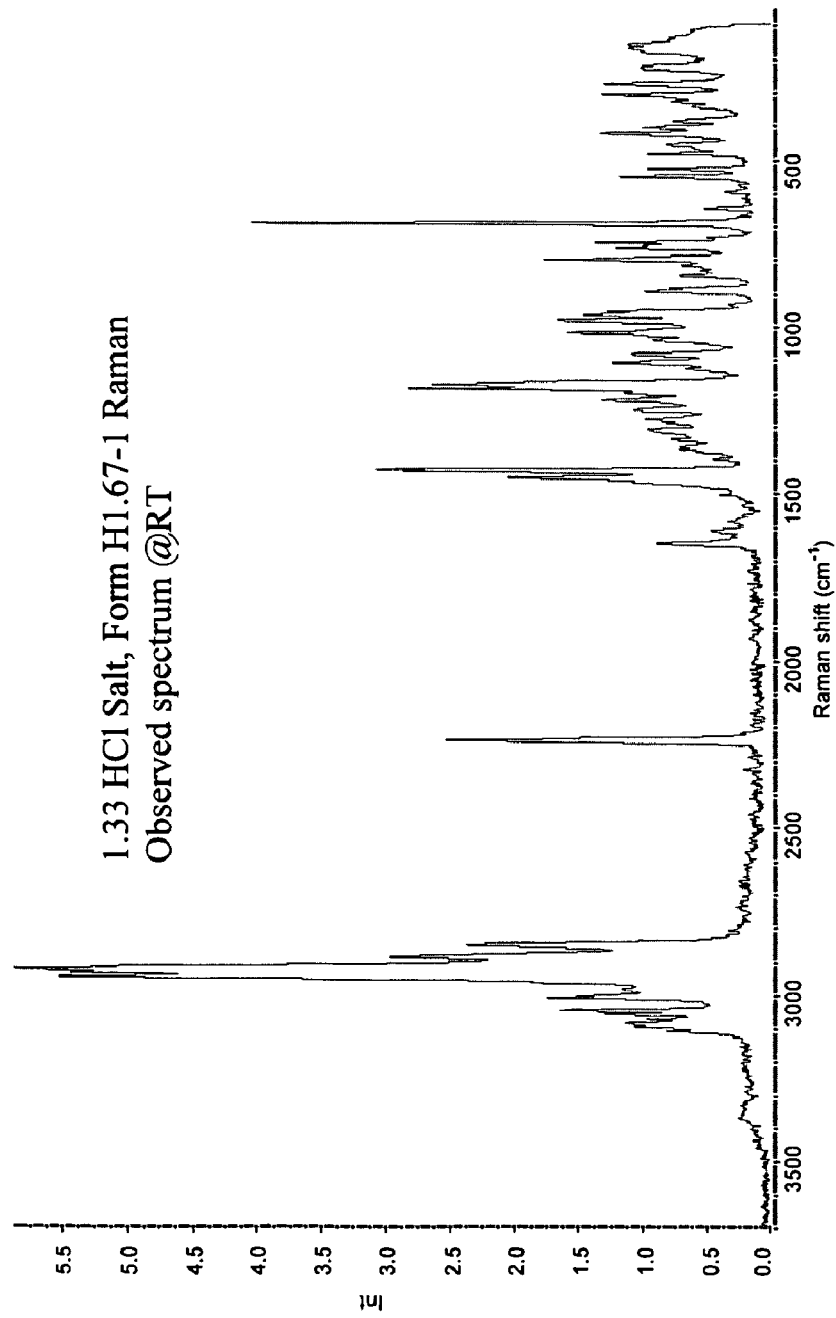
FIG. 19 shows an observed Raman spectrum at room temperature of the crystalline saxagliptin 1.33HCl salt (1.67 equiv. $H_2O$) (form H1.67-1).
Figure 20:
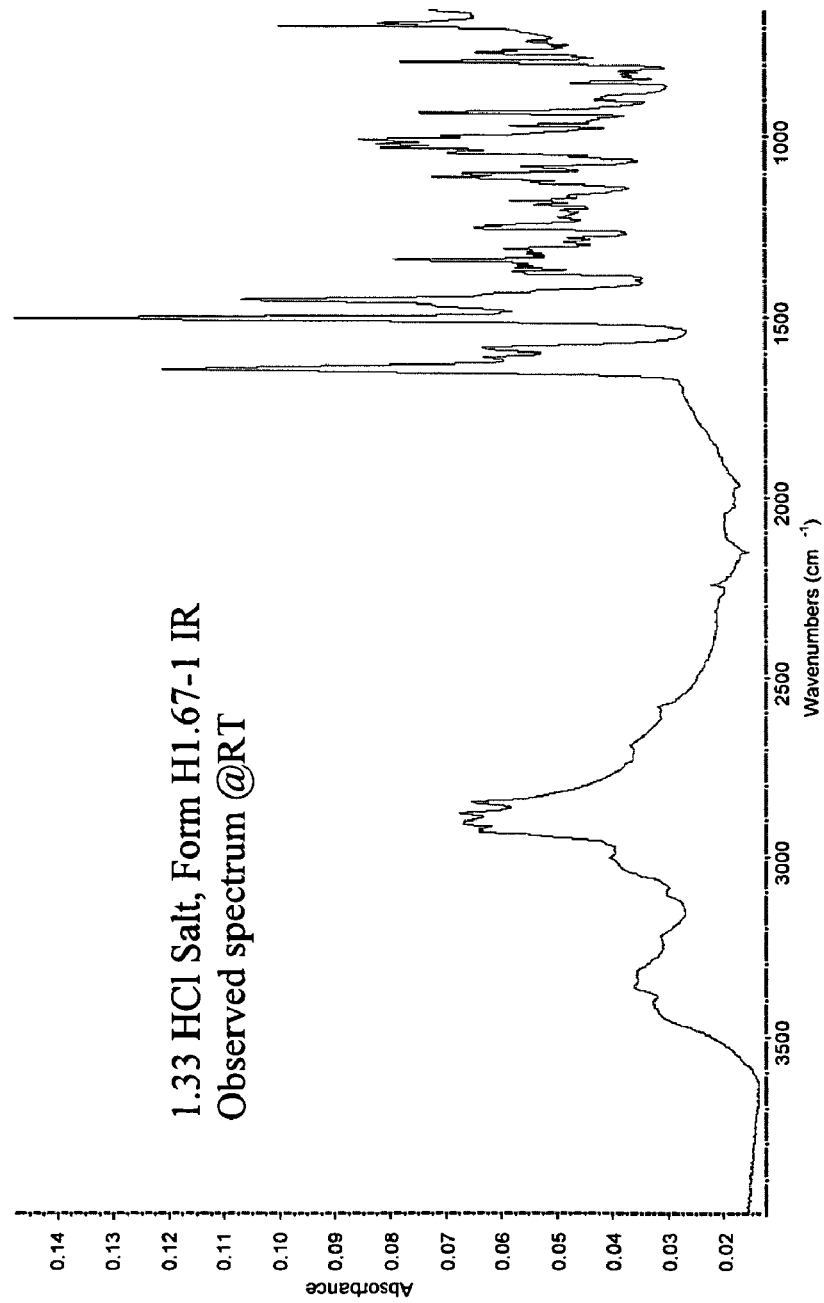
FIG. 20 shows an observed IR spectrum at room temperature of the crystalline saxagliptin 1.33HCl salt (1.67 equiv. $H_2O$) (form H1.67-1).

As seen in FIG. 18, the 1.33HCl salt (form H1.67-1) had a weight loss of 10.85% up to about 150° C.

Figure 24:
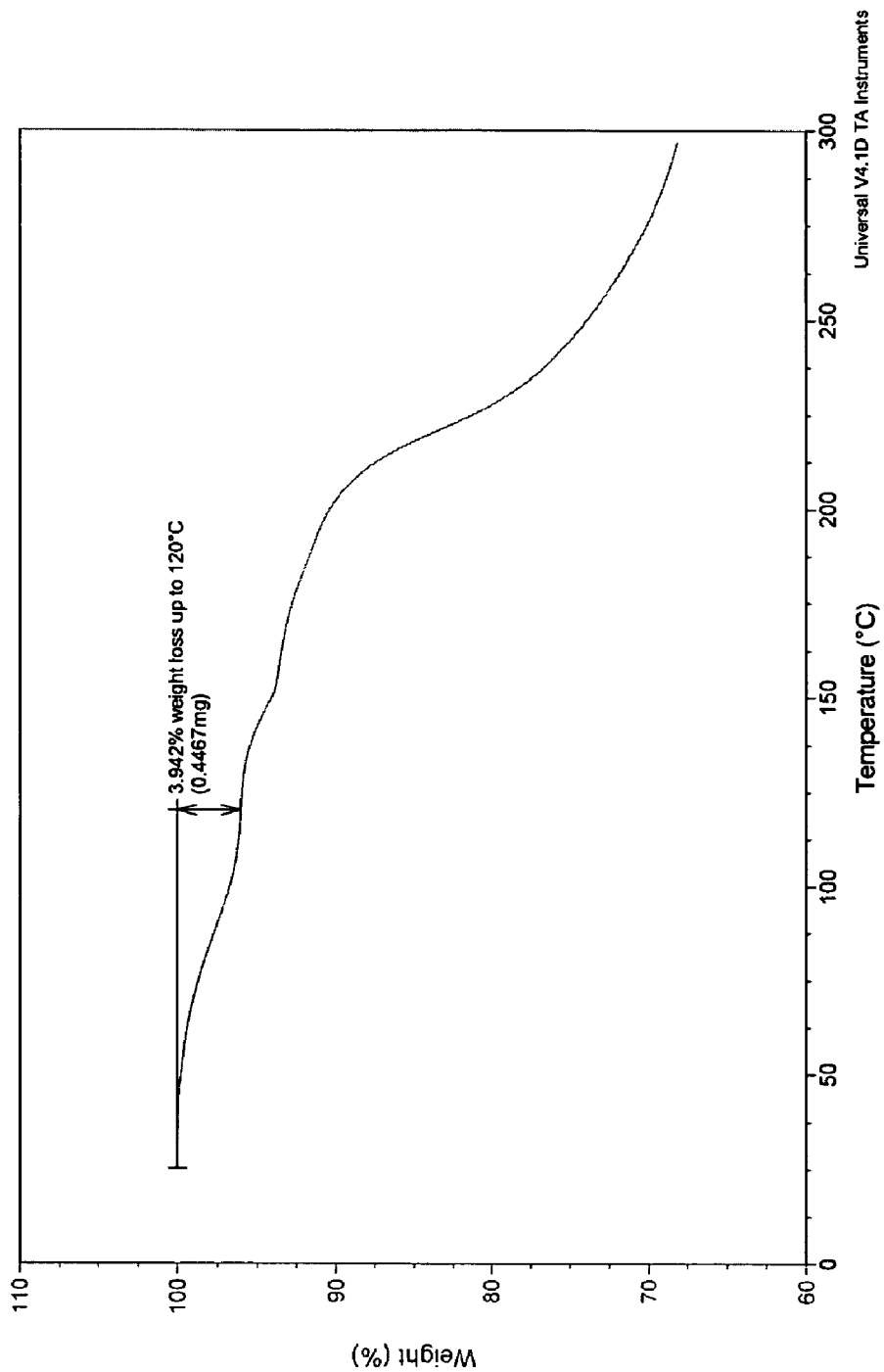
FIG. 24 shows a thermogravimetric analysis (TGA) curve of the crystalline saxagliptin benzoate salt (form H-1).

As seen in FIG. 24 the benzoate salt (form H-1) had a TGA weight loss of about 3.94% up to about 120° C.

Figure 27:
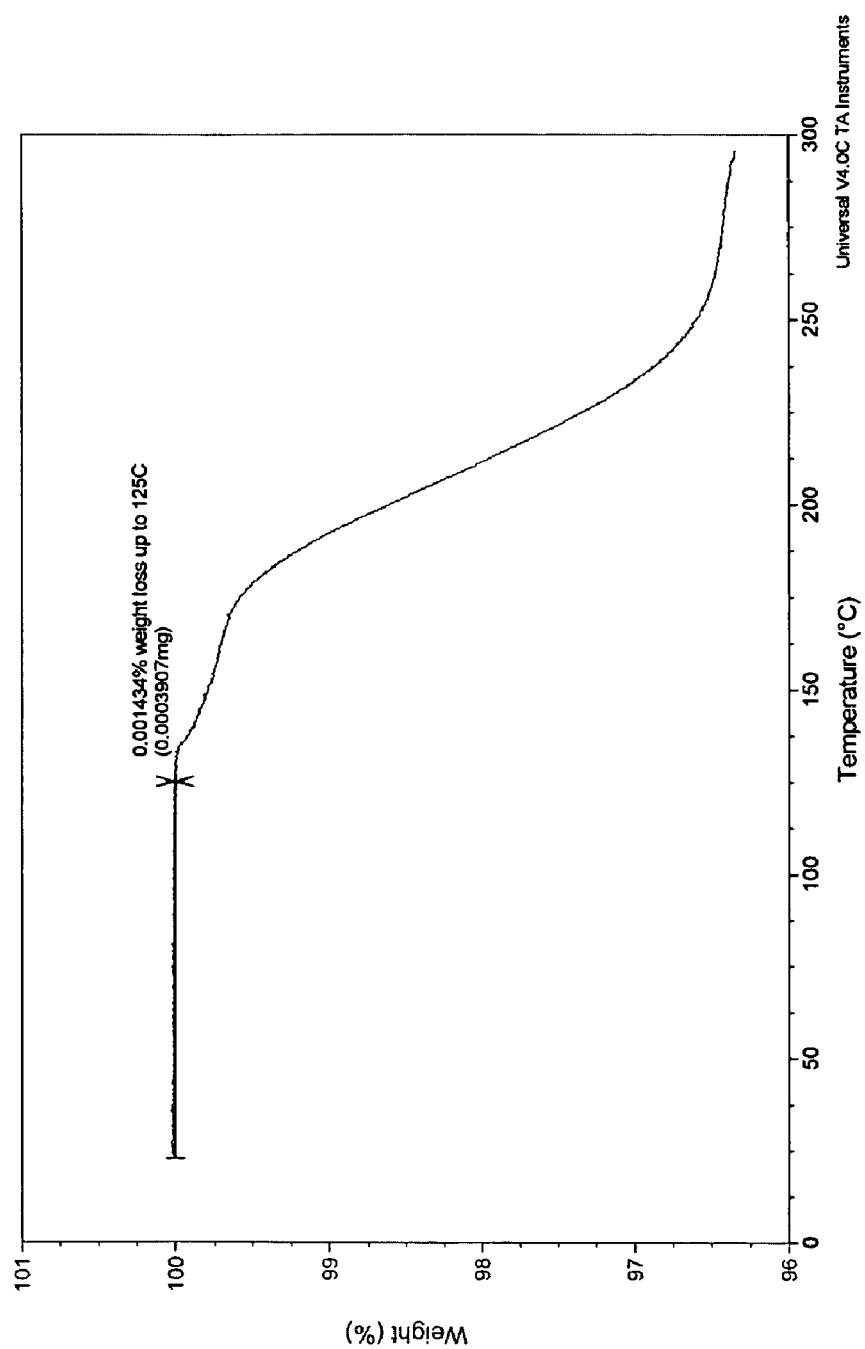
FIG. 27 shows a thermogravimetric analysis (TGA) curve of the crystalline saxagliptin free base (neat) (form N-3).

As seen in FIG. 27, the free base (neat) (form N-3) had a TGA weight loss of about 0.001 up to about 125° C.

Differential Scanning Calorimetry

The solid state thermal behavior of the free base monohydrate (form H-1), HCl salt (form H2-1), HCl salt (form H0.75-3), 1.33HCl salt (form H1.67-1), benzoate salt (form H-1), and free base (form N-3) structures were investigated by differential scanning calorimetry (DSC). The DSC curves for the above structures are shown in FIGS. 2, 7, 12, 17 23 and 26, respectively.

Differential scanning calorimetry (DSC) experiments were performed in a TA Instruments™ model Q1000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. for HCl salt H2-1, free base monohydrate H-1 and benzoate salt H-1 and between room temperature and 350° C. for the HCl salt H0.75-3, at 10° C./min heating rate. The plot was made with the endothermic peaks pointing down.

Figure 2:
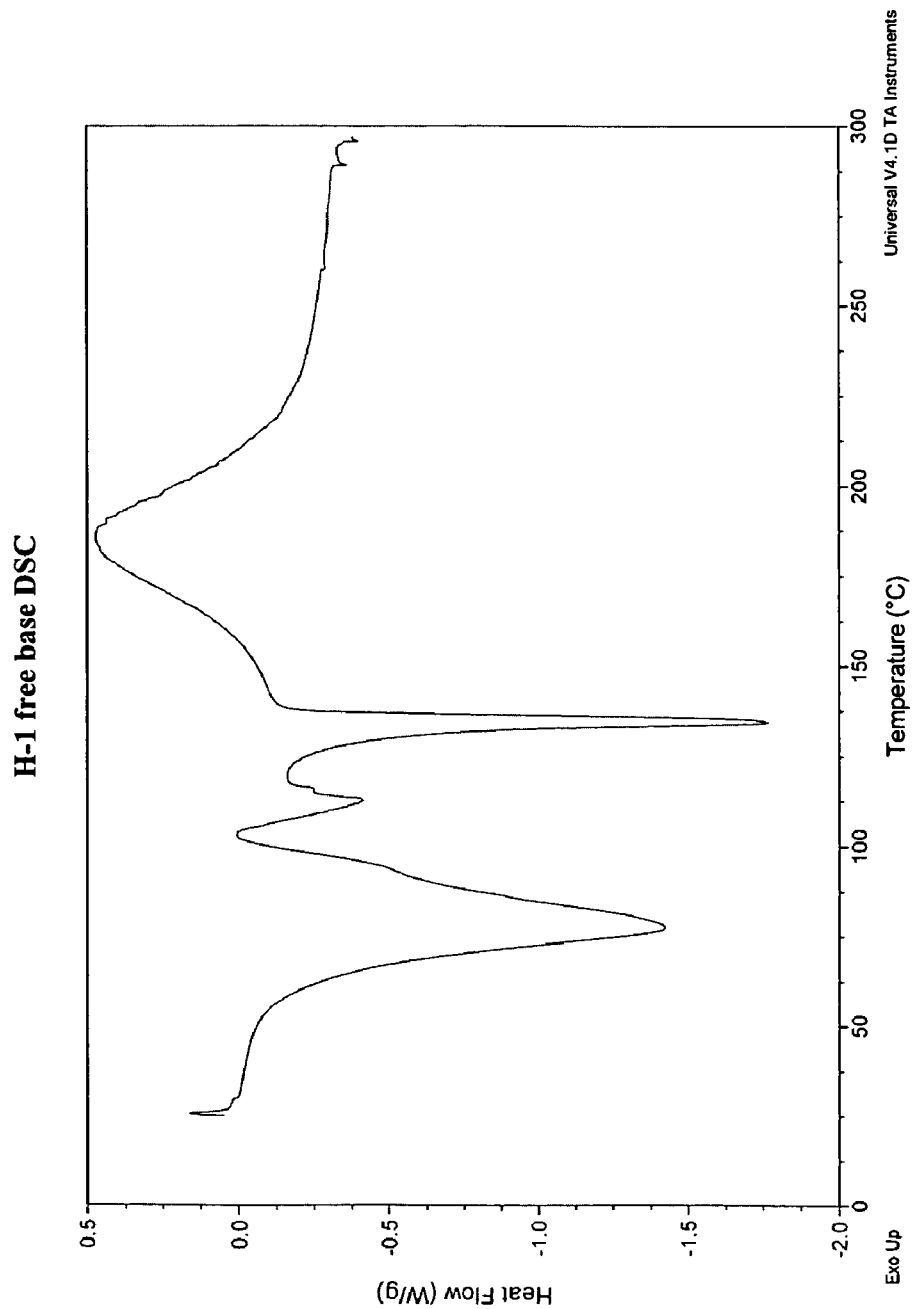
FIG. 2 shows a differential scanning calorimetry (DSC) thermogram of the crystalline saxagliptin free base monohydrate (form H-1).

As seen in FIG. 2, the free base monohydrate (form H-1) had a DSC endotherm in the range from about room temperature to about 120° C.

Figure 7:
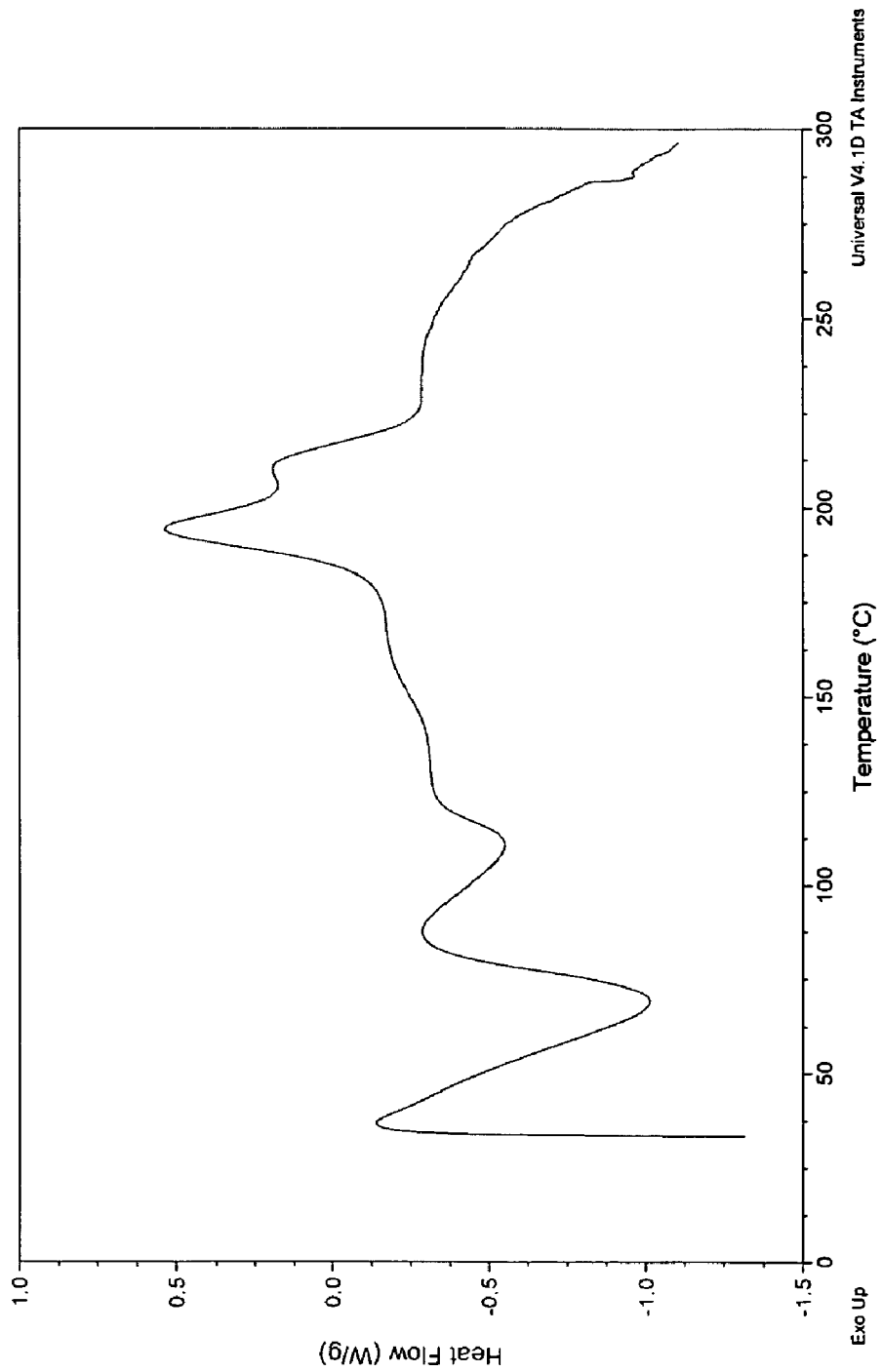
FIG. 7 shows a differential scanning calorimetry (DSC) thermogram of the crystalline saxagliptin mono HCl salt (2 equiv. $H_2O$) (form H2-1).

As seen in FIG. 7, the HCl salt (form H2-1) had a DSC endotherm in the range from about room temperature to about 85° C.

Figure 12:
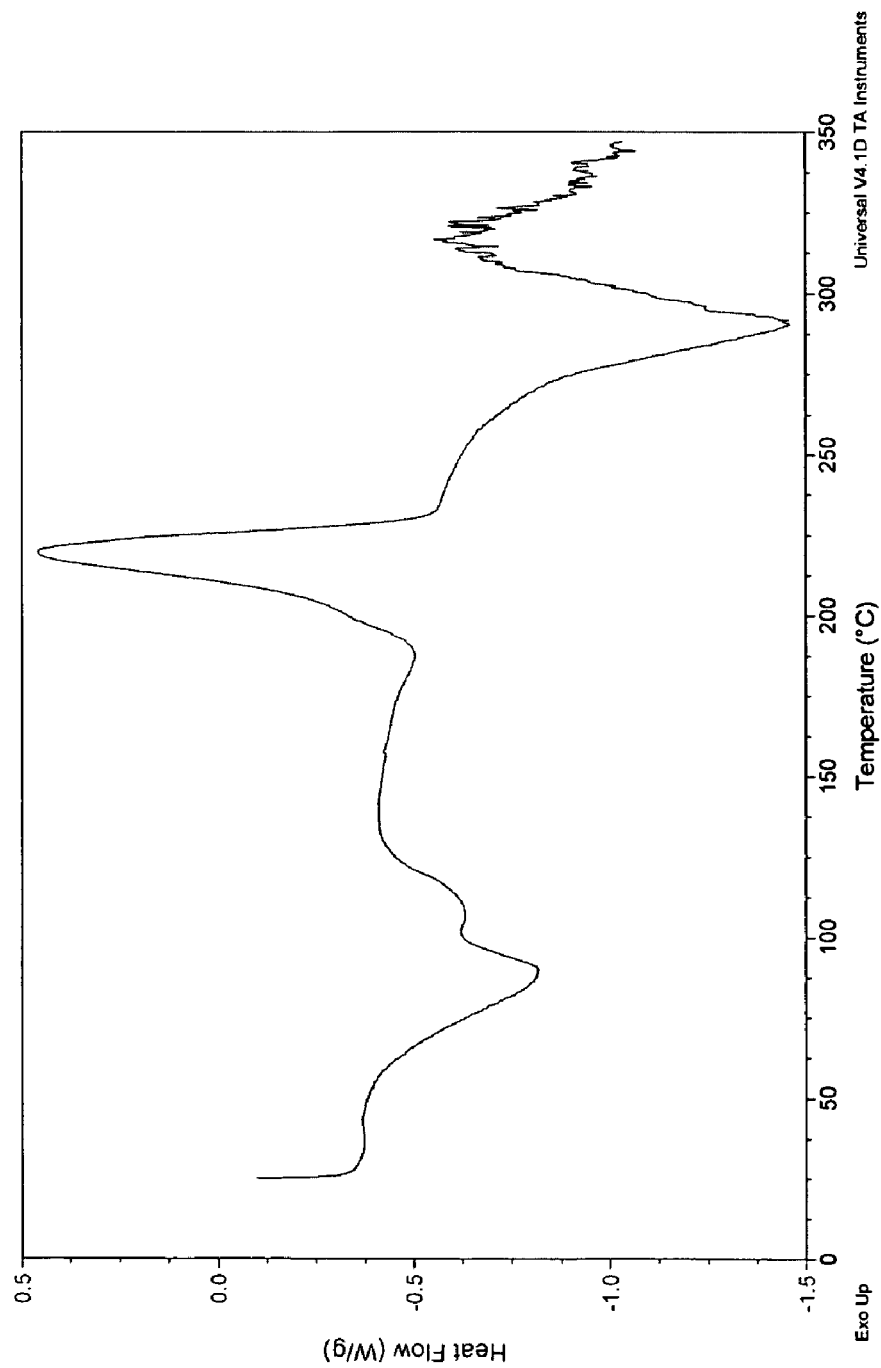
FIG. 12 shows a differential scanning calorimetry (DSC) thermogram of the crystalline saxagliptin HCl salt (0.75 equiv. $H_2O$) (form H0.75-3).

As seen in FIG. 12, the HCl salt (form H0.75-3) had a DSC endotherm in the range from about room temperature to about 150° C.

Figure 17:
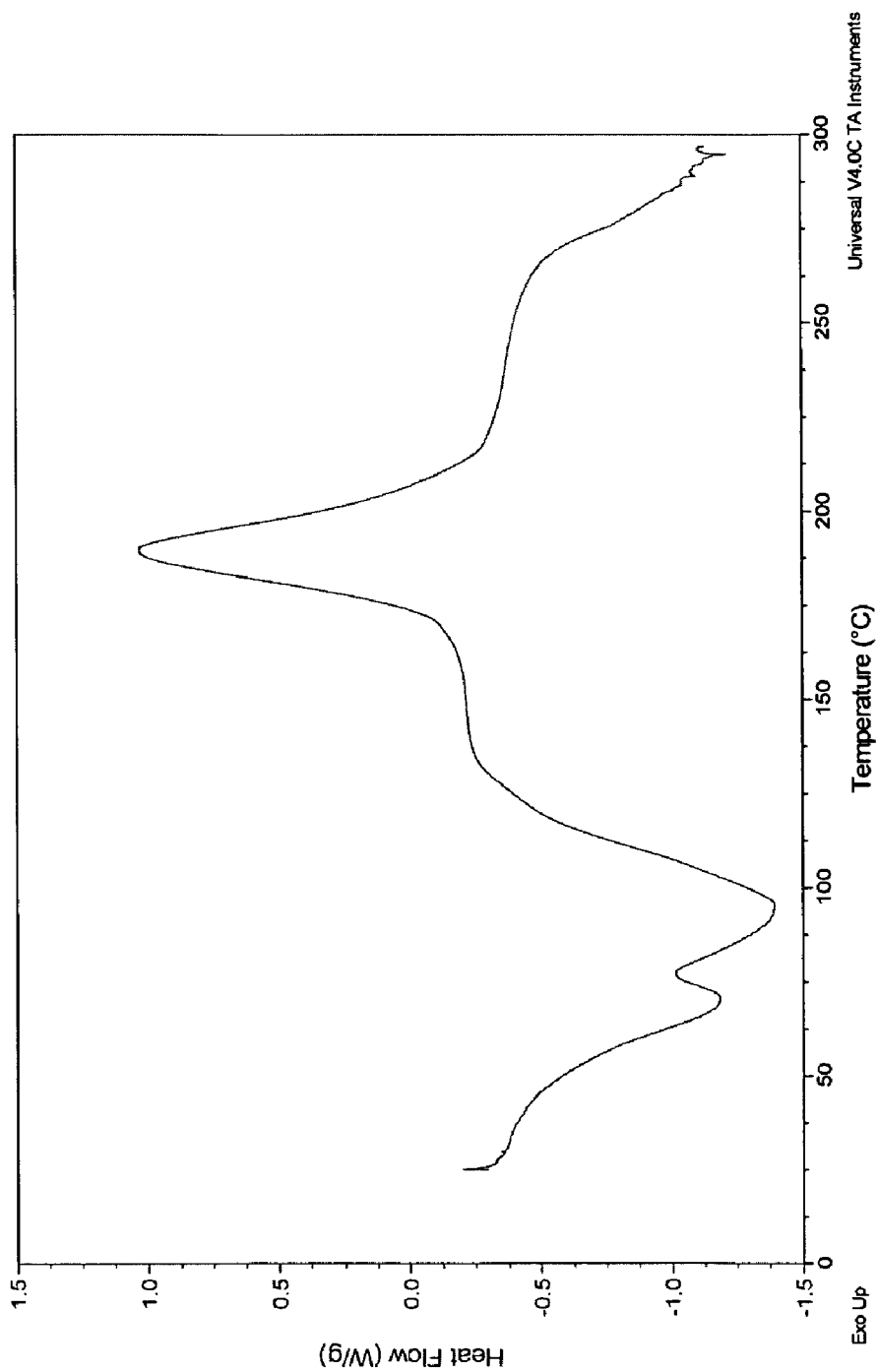
FIG. 17 shows a differential scanning calorimetry (DSC) thermogram of the crystalline saxagliptin 1.33HCl salt (1.67 equiv. $H_2O$) (form H1.67-1).

As seen in FIG. 17, the 1.33HCl salt (form H1.67-1) had a DSC endotherm in the range from about room temperature to about 150° C.

Figure 23:
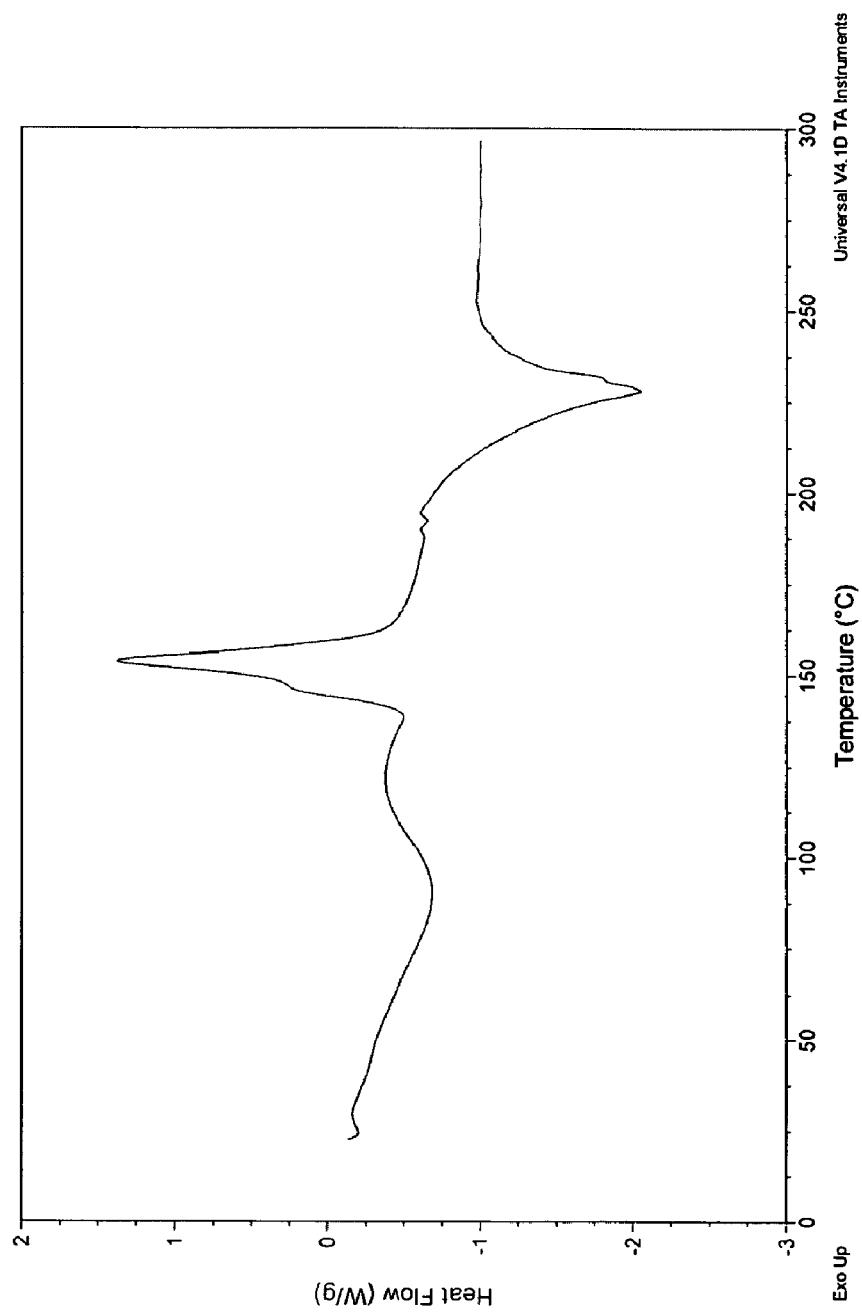
FIG. 23 shows a differential scanning calorimetry (DSC) thermogram of the crystalline saxagliptin benzoate salt (form H-1).

As seen in FIG. 23, the benzoate salt (form H-1) had a DSC endotherm in the range from about room temperature to about 300° C.

Figure 26:
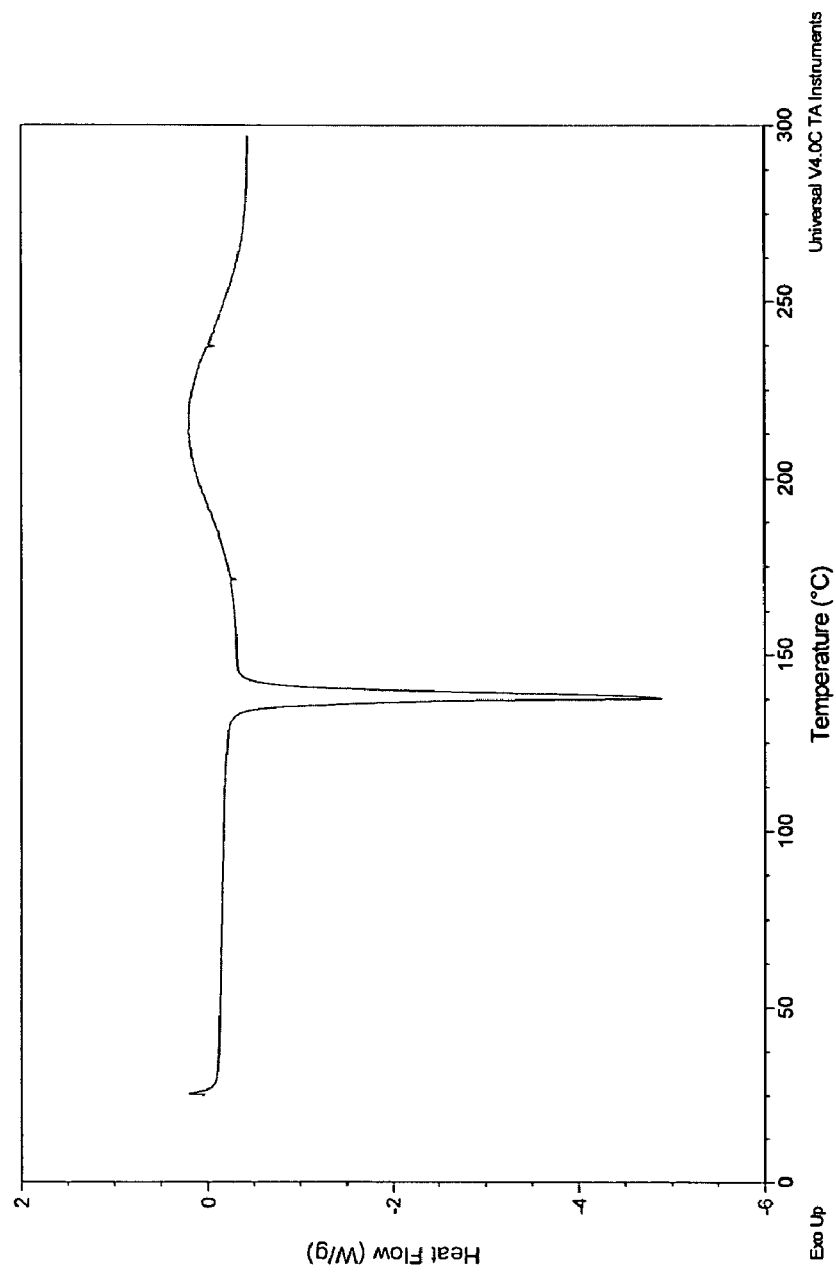
FIG. 26 shows a differential scanning calorimetry (DSC) thermogram of the crystalline saxagliptin free base (neat) (form N-3).

As seen in FIG. 26, the free base (neat) (form N-3) had a DSC endotherm in the range from about 135 to about 140° C.

One of skill in the art will however, note that in DSC measurement there is a certain degree of variability in actual measured onset and peak temperatures, depending on rate of heating, crystal shape and purity, and other measurement parameters.

Raman Spectroscopy

Raman spectra for the free base monohydrate (form H-1), HCl salt (form H2-1) and HCl salt (form H0.75-3) were acquired at a resolution of 8 cm$^{-1}$ with 128 scans co-added, using a Nicolet 950 FT-Raman spectrophotometer. The wavelength of the laser excitation was 1064 nm. A CaF$_2$ beam splitter and a high sensitivity InGaS detector were used.

Raman spectra for the free base monohydrate (form H-1), HCl salt (form H2-1), HCl salt (form H0.75-3) and 1.33HCl salt (form H1.67-1) are shown in FIGS. 4, 9, 14 and 19, respectively.

IR Spectroscopy

Infrared spectra for the free base monohydrate (form H-1), HCl salt (form H2-1) and HCl salt (form H0.75-3) were acquired at a resolution of 4 cm$^{-1}$ with 32 scans co-added, using a Nicolet 560 FT-IR Spectrophotometer, incorporating a KBr beam-splitter and DTGS detector. Sample preparation was via the attenuated total reflectance method (ATR) using a single-bounce diamond ATR sampling accessory (Durasamp1IR) from SensIR. An ATR correction step was included to correct the pathlength.

IR spectra for the free base monohydrate (form H-1), HCl salt (form H2-1), HCl salt (form H0.75-3), and 1.33HCl salt (form H1.67-1) are shown in FIGS. 5, 10, 15 and 20, respectively.

Fourier-Transform Near Infrared (FT-NIR)

Data for saxagliptin HCl salt Pattern P-5 (shown in FIG. 30) were acquired at room temperature in reflectance mode on a Thermo Nicolet Antaris Fourier-Transform near infrared spectrometer equipped with an integrating sphere. Sixty-four scans were collected at a resolution was of 8 cm$^{-1}$ with a gain of 1 and no attenuation of the source and an aperture setting of 100. The interferogram was collected with a 20 bit digitizer and a mirror velocity of 1.2659. Mertz phase correction was applied with Norton-Beer medium apodization. The mirror position was referenced to a helium-neon laser. No zero filling was utilized. Data were collected from 4000 cm$^{-1}$ to 10000 cm$^{-1}$ on an InGaAs detector with a CaF$_2$ beamsplitter. Total collection time was ca. 34 seconds. The background was collected using a gold reflection standard with settings identical to those of the spectrum. Background and sample data were collected using Result Operation software. The data was displayed as log 1/R on the ordinate and as wave numbers on the abscissa. No baseline correction, sample smoothing, scattering correction, or derivatives were applied.

The samples were either placed directly on the sample window, collected in a clear, colorless glass vial, or collected on a microscope slide. Powder samples of drug substance were typically collected with >1 mm powder bed depth. Coated tablets were typically analyzed by centering the intact tablet directly on the window of the integrating sphere. Data on coated tablets were displayed in selected regions such that contribution from overlapping peaks from the coating or core excipients was minimal As seen in FIG. 30, the HCl salt Pattern P-5 does not exhibit any placebo peaks.

Single Crystal X-ray Analysis

A single crystal for the structure were obtained and investigated by X-ray diffraction.

Data were collected on a Bruker-Nonius[2] CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package[3] in the Collect program suite.[4]

[2] BRUKER AXS, 5465 East Cheryl Parkway Madison, Wis. 53711 USA
[3] Otwinowski, Z. et al., *Macromolecular Crystallography*, Academic, NY, publ., Carter, W. C., Jr. et al., eds., 276:307-326 (1997).
[4] Collect Data collection and processing user interface: Collect: Data collection software, R. Hooft, Nonius B. V. (1998).

When indicated, crystals were cooled in the cold stream of an Oxford cryo system[5] during data collection.

[5] Oxford Cryosystems Cryostream cooler: Cosier, J. et al., *J. Appl. Cryst.*, 19:105 (1986).

The structures were solved by direct methods and refined on the basis of observed reflections using either the SDP[6] software package with minor local modifications or the crystallographic package, MAXUS.[7]

[6] SDP, Structure Determination Package, Enraf-Nonius, Bohemia N.Y. 11716. Scattering factors, including f' and f", in the SDP software were taken from the "International Tables for Crystallography", Kynoch Press, Birmingham, England, 1974; Vol. IV, Tables 2.2A and 2.3.1.
[7] maXus solution and refinement software suite: S. Mackay, C. J. Gilmore, C. Edwards, M. Tremayne, N. Stewart, K. Shankland. maXus: a computer program for the solution and refinement of crystal structures from diffraction data.

The derived atomic parameters (coordinates and temperature factors) were refined through full matrix least-squares. The function minimized in the refinements was $\tau_w(|F_O|-|F_C|)^2$. R is defined as $\Sigma||F_O|-|F_C||/\Sigma|F_O|$ while $R_w=[\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Unit cell parameters for the monohydrate saxagliptin free base structure form H-1 are listed below in Table 1. As used herein, the unit cell parameter "molecules/per cell" refers to the number of molecules of Compound in the unit cell.

TABLE 1

Unit Cell Data for the Monohydrate Free Base H-1

| Structure | T° C. | a(Å) | b(Å) | c(Å) | α° | β° | γ° | Z' | SG |
|---|---|---|---|---|---|---|---|---|---|
| Monohydrate free base H-1 | 22 | 7.270(1) | 14.234(1) | 16.929(1) | 90 | 90 | 90 | 1 | $P2_12_12_1$ |

T = temp (° C.) for the crystallographic data.
Z' = number of drug molecules per asymmetric unit
SG = space group Table 2 below sets forth the positional parameters for the monohydrate saxagliptin free base form H-1 structure at 22° C.:

TABLE 2

Positional Parameters and Estimated Standard Deviations for Saxagliptin Free Base Monohydrate Form H-1 at Room Temperature

| Atom | x | y | z | B(iso) |
|---|---|---|---|---|
| O8 | 0.4468(4) | 0.4805(1) | 0.2806(1) | 4.45(5) |
| O12 | 0.6276(3) | 0.3520(1) | 0.5513(1) | 3.49(4) |
| O99 | −0.0687(4) | 0.3156(2) | 0.4564(2) | 6.27(6) |
| N1 | 0.3842(3) | 0.6329(1) | 0.2664(1) | 2.56(4) |
| N6 | 0.8457(4) | 0.6312(3) | 0.2824(2) | 6.64(8) |
| N9 | 0.1041(4) | 0.4599(2) | 0.3586(1) | 4.00(5) |
| C2 | 0.5327(4) | 0.6428(2) | 0.2080(1) | 3.07(5) |
| C3 | 0.5017(4) | 0.7398(2) | 0.1697(2) | 3.85(6) |
| C4 | 0.3708(5) | 0.7903(2) | 0.2229(2) | 4.15(6) |
| C5 | 0.2959(4) | 0.7216(2) | 0.2815(2) | 3.27(5) |
| C6 | 0.7115(4) | 0.6359(2) | 0.2489(2) | 4.13(6) |
| C7 | 0.4200(5) | 0.7992(2) | 0.3090(2) | 4.38(6) |
| C8 | 0.3599(4) | 0.5493(2) | 0.3028(1) | 2.74(5) |
| C9 | 0.2250(4) | 0.5418(2) | 0.3715(1) | 2.71(5) |
| C10 | 0.3286(3) | 0.5354(2) | 0.4511(1) | 2.27(4) |
| C11 | 0.4324(3) | 0.4419(2) | 0.4613(1) | 2.33(4) |
| C12 | 0.5300(4) | 0.4388(2) | 0.5417(1) | 2.57(4) |
| C13 | 0.3878(4) | 0.4480(2) | 0.6074(1) | 3.16(5) |
| C14 | 0.2859(4) | 0.5418(2) | 0.5992(1) | 3.31(5) |
| C15 | 0.1888(4) | 0.5454(2) | 0.5187(2) | 3.04(5) |
| C16 | 0.4687(4) | 0.6164(2) | 0.4581(1) | 2.74(5) |
| C17 | 0.5660(4) | 0.6132(2) | 0.5387(2) | 3.11(5) |
| C18 | 0.4236(5) | 0.6227(2) | 0.6050(2) | 3.85(6) |
| C19 | 0.6667(4) | 0.5194(2) | 0.5466(2) | 3.05(5) |
| H121 | 0.539 | 0.295 | 0.547 | 4.5 |

Unit cell parameters for the hemi-hydrate of the saxagliptin free base structure (form H.5-2) are listed below in Table 3:

TABLE 3

Unit Cell Data for Form H0.5-2

| Form | T° | a(Å) | b(Å) | c(Å) | α° | β° | γ° | Z' | SG |
|---|---|---|---|---|---|---|---|---|---|
| H0.5-2 | −40 | 13.841(2) | 13.841(2) | 15.273(6) | 90 | 90 | 120 | 1 | P64 |

T = temp (° C.) for crystallographic data
Z' = number of drug molecules per asymmetric unit
SG = space group Table 4 below sets forth the positional parameters for the form H0.5-2 at −40° C.:

TABLE 4

Positional Parameters and their Estimated Standard Deviations for Saxagliptin Free Base 0.5H$_2$O Form H.5-2 at −40° C.

| Atom | x | y | z | B(iso) | Occupancy* |
|---|---|---|---|---|---|
| O8 | 0.0946(2) | 0.1680(2) | 0.1322(2) | 2.69(7) | |
| O12 | 0.3654(2) | 0.1944(3) | −0.1059(2) | 3.96(9) | |
| O99 | 0.000 | 0.0000 | 0.0072(3) | 4.1(1) | .5 |
| N1 | 0.1811(3) | 0.2798(3) | 0.2458(3) | 2.41(8) | |
| N6 | 0.1705(5) | 0.4474(4) | 0.0879(4) | 9.2(2) | |
| N9 | 0.1654(3) | 0.0192(3) | 0.1921(2) | 2.58(9) | |
| C2 | 0.1139(4) | 0.3337(4) | 0.2334(4) | 3.7(1) | |
| C3 | 0.1396(4) | 0.4072(4) | 0.3164(5) | 6.1(2) | |
| C4 | 0.2357(4) | 0.4136(4) | 0.3594(3) | 3.5(1) | |
| C5 | 0.2578(4) | 0.3286(4) | 0.3177(3) | 3.9(1) | |
| C6 | 0.1442(4) | 0.3962(4) | 0.1529(4) | 5.1(1) | |
| C7 | 0.3398(4) | 0.4516(5) | 0.3087(4) | 5.3(2) | |
| C8 | 0.1663(3) | 0.1967(3) | 0.1912(3) | 2.4(1) | |
| C9 | 0.2353(3) | 0.1401(3) | 0.2039(3) | 2.2(1) | |
| C10 | 0.3372(3) | 0.1907(3) | 0.1396(3) | 2.4(1) | |
| C11 | 0.3006(3) | 0.1699(3) | 0.0432(3) | 2.4(1) | |
| C12 | 0.4023(3) | 0.2189(3) | −0.0163(3) | 2.8(1) | |
| C13 | 0.4734(3) | 0.1662(3) | 0.0012(3) | 3.0(1) | |
| C14 | 0.5120(3) | 0.1863(4) | 0.0973(3) | 3.2(1) | |
| C15 | 0.4085(3) | 0.1354(3) | 0.1579(3) | 2.6(1) | |
| C16 | 0.4099(3) | 0.3161(3) | 0.1546(3) | 2.7(1) | |
| C17 | 0.5122(4) | 0.3655(4) | 0.0943(3) | 3.3(1) | |
| C18 | 0.4710(3) | 0.3442(4) | −0.0020(3) | 3.2(1) | |
| C19 | 0.5826(4) | 0.3107(4) | 0.1131(3) | 3.7(1) | |
| H121 | 0.291 | 0.202 | −0.115 | 3.7 | |

*Occupancy is 1. unless otherwise indicated.

Unit cell parameters for the saxagliptin free base (neat) form N-3 are listed below in Table 5:

TABLE 5

Unit Cell Data for Free Base (neat) Form N-3

| Form | T° | a(Å) | b(Å) | c(Å) | α° | β° | γ° | Z' | SG |
|---|---|---|---|---|---|---|---|---|---|
| N-3 | 22 | 22.739(2) | 25.646(2) | 8.6785(3) | 90 | 90 | 90 | 3 | $P2_12_12_1$ |

T = temp (° C.) for crystallographic data
Z' = number of drug molecules per asymmetric unit
SG = space group Table 6 below sets forth the positional parameters for the free base neat form N-3 at 22° C.:

TABLE 6

Positional Parameters and Estimated Standard Deviations for Saxagliptin Free Base Form N-3 at rt

| Atom | x | y | z | B(iso) |
|---|---|---|---|---|
| O1 | −0.05987(10) | 0.44920(9) | 0.7049(3) | 4.2 |
| O2 | −0.22352(10) | 0.45680(11) | 0.0364(3) | 4.6 |
| C3 | −0.13471(13) | 0.45476(13) | 0.4101(4) | 3.3 |
| N4 | −0.17842(14) | 0.48805(13) | 0.6584(3) | 4.6 |
| C5 | −0.10153(14) | 0.42147(14) | 0.6705(4) | 3.2 |
| C6 | −0.05076(13) | 0.34842(13) | 0.7914(4) | 3.7 |
| N7 | −0.10266(11) | 0.37054(10) | 0.7152(3) | 3.2 |
| C8 | −0.18981(13) | 0.45279(14) | 0.3039(4) | 3.4 |
| C9 | −0.17285(14) | 0.46183(14) | 0.1359(4) | 3.5 |
| C10 | −0.15349(14) | 0.44283(14) | 0.5790(4) | 3.5 |
| C11 | −0.12974(15) | 0.42073(16) | 0.0841(4) | 3.4 |
| C12 | −0.10595(17) | 0.50825(15) | 0.3914(4) | 4.2 |
| C13 | −0.07321(16) | 0.29766(14) | 0.8668(5) | 4.4 |
| C14 | −0.09167(16) | 0.41289(15) | 0.3530(4) | 4.6 |
| C15 | −0.14527(19) | 0.51534(15) | 0.1222(5) | 3.9 |
| C16 | −0.14873(15) | 0.33258(15) | 0.6982(5) | 4.5 |
| C17 | −0.12994(17) | 0.28580(15) | 0.7875(6) | 5.0 |
| C18 | −0.00471(16) | 0.33843(15) | 0.6762(5) | 4.5 |
| C19 | −0.07432(15) | 0.42285(17) | 0.1838(4) | 4.5 |
| C20 | −0.04633(17) | 0.4763(2) | 0.1696(5) | 5.8 |
| C21 | −0.09005(18) | 0.51780(17) | 0.2225(5) | 5.2 |
| N22 | 0.03052(17) | 0.33001(17) | 0.5864(6) | 7.0 |
| C23 | −0.1313(2) | 0.28391(16) | 0.6124(6) | 6.2 |
| O24 | 0.39419(11) | 0.79443(10) | 0.7172(3) | 5.2 |
| O25 | 0.42635(11) | 0.87804(10) | 0.1830(3) | 5.2 |
| C26 | 0.33327(16) | 0.74865(14) | 0.3620(4) | 4.1 |
| C27 | 0.28533(16) | 0.69115(14) | 0.7047(4) | 4.1 |
| C28 | 0.36687(15) | 0.84136(14) | 0.3812(4) | 3.9 |
| N29 | 0.33770(11) | 0.72288(11) | 0.7255(3) | 3.8 |
| C30 | 0.34677(15) | 0.77270(14) | 0.6836(4) | 3.7 |
| C31 | 0.31650(14) | 0.80372(13) | 0.4189(4) | 3.7 |
| N32 | 0.29296(13) | 0.85315(12) | 0.6688(4) | 3.3 |
| C33 | 0.30044(15) | 0.80230(14) | 0.5928(4) | 4.9 |
| C34 | 0.26124(14) | 0.82134(14) | 0.3289(4) | 3.6 |
| C35 | 0.34544(15) | 0.75000(15) | 0.1890(5) | 3.9 |
| C36 | 0.38554(15) | 0.69249(14) | 0.7927(4) | 4.3 |
| C37 | 0.37937(14) | 0.84165(14) | 0.2081(4) | 4.5 |
| C38 | 0.27380(16) | 0.82210(14) | 0.1559(4) | 4.4 |
| C39 | 0.39568(17) | 0.78716(15) | 0.1560(5) | 4.5 |
| C40 | 0.32459(16) | 0.85960(15) | 0.1222(5) | 4.5 |
| C41 | 0.29023(17) | 0.76709(15) | 0.1030(5) | 4.7 |
| C42 | 0.29718(17) | 0.64009(15) | 0.7822(5) | 5.0 |
| C43 | 0.29261(19) | 0.64308(16) | 0.6106(5) | 5.3 |
| C44 | 0.35622(18) | 0.64272(16) | 0.8560(6) | 5.4 |
| C45 | 0.4286(2) | 0.68043(18) | 0.6744(6) | 6.1 |
| N46 | 0.4604(2) | 0.6688(2) | 0.5760(7) | 10.0 |
| O47 | 0.15963(11) | 0.62069(10) | 0.7441(3) | 4.7 |
| C48 | 0.07982(15) | 0.62631(14) | 0.4479(4) | 3.5 |
| N49 | 0.11404(12) | 0.54375(11) | 0.7477(3) | 3.5 |
| C50 | 0.11611(15) | 0.59490(14) | 0.7079(4) | 3.5 |
| N51 | 0.04708(14) | 0.66766(13) | 0.6931(4) | 4.5 |
| C52 | 0.06518(14) | 0.61853(13) | 0.6214(4) | 3.6 |
| C53 | 0.02175(14) | 0.63469(15) | 0.3619(4) | 3.9 |
| O54 | −0.02329(12) | 0.64764(12) | 0.1109(3) | 5.7 |
| C55 | 0.03222(16) | 0.64207(15) | 0.1904(4) | 4.3 |
| C56 | 0.11021(16) | 0.57825(15) | 0.3791(4) | 4.6 |
| C57 | 0.0712(2) | 0.68926(17) | 0.1661(5) | 5.6 |
| C58 | 0.06243(17) | 0.59442(17) | 0.1249(5) | 4.6 |
| C59 | 0.06628(16) | 0.50661(15) | 0.7200(5) | 4.5 |
| C60 | 0.16495(15) | 0.51800(14) | 0.8183(5) | 4.4 |
| C61 | 0.08377(19) | 0.45703(17) | 0.7979(6) | 5.9 |
| C62 | 0.11947(17) | 0.67434(16) | 0.4207(4) | 4.6 |
| C63 | 0.12106(17) | 0.58623(17) | 0.2066(5) | 4.8 |
| C64 | 0.21108(18) | 0.51072(17) | 0.7069(6) | 5.6 |
| C65 | 0.0820(2) | 0.46031(16) | 0.6246(6) | 6.1 |
| C66 | 0.14030(19) | 0.46597(17) | 0.8809(6) | 5.8 |
| C67 | 0.1297(2) | 0.68103(19) | 0.2473(5) | 5.6 |
| C68 | 0.16031(18) | 0.6337(2) | 0.1833(5) | 6.0 |
| N69 | 0.2470(2) | 0.5033(2) | 0.6186(7) | 9.3 |

Unit cell parameters for the HCl salt 2 equiv. $H_2O$ form H2-1 saxagliptin are listed below in Table 7:

TABLE 7

Unit Cell Data for MonoHCl Salt 2 equiv. $H_2O$ Form H2-1

| Form | T° | a(Å) | b(Å) | c(Å) | α° | β° | γ° | Z' | SG |
|---|---|---|---|---|---|---|---|---|---|
| HCl salt | −50 | 10.994(1) | 6.834(1) | 12.922(1) | 90 | 95.66(1) | 90 | 1 | $P2_1$ |
| (H2-1) | +22 | 11.0261(4) | 6.8436(2) | 12.9928(4) | 90 | 95.734(2) | 90 | 1 | $P2_1$ |

T = temp (° C.) for crystallographic data
Z' = number of drug molecules per asymmetric unit
SG = space group Table 7A below sets forth the positional parameters for the HCl salt 2 equiv. H₂O form H2-1 saxagliptin are listed below:

TABLE 7A

Positional Parameters and their Estimated Standard Deviations for HCl Salt Form H2-1 at rt

| Atom | x | y | z | B(iso) |
|---|---|---|---|---|
| Cl1 | 0.71464(9) | 0.15050(16) | 0.02389(8) | 5.1 |
| O1 | 0.5783(3) | 0.6616(7) | −0.0840(2) | 6.1 |
| O2 | 0.9902(3) | 0.7298(6) | −0.0268(2) | 6.1 |
| O8 | 0.98215(19) | 0.5055(4) | 0.17861(18) | 3.5 |
| O12 | 0.3839(2) | 0.5140(7) | 0.2039(2) | 5.3 |
| N1 | 1.0095(2) | 0.8115(4) | 0.2377(2) | 3.0 |
| N6 | 1.1726(4) | 0.5643(8) | 0.4352(3) | 5.9 |
| N9 | 0.7826(2) | 0.6001(5) | 0.05558(18) | 3.2 |
| C2I | 1.1404(3) | 0.7709(6) | 0.2657(3) | 3.5 |
| C3I | 1.2000(3) | 0.9729(7) | 0.2768(3) | 4.2 |
| C4I | 1.0990(4) | 1.1156(7) | 0.2880(3) | 4.5 |
| C5I | 0.9800(3) | 1.0126(7) | 0.2584(3) | 3.8 |
| C6 | 1.1572(3) | 0.6540(7) | 0.3614(3) | 4.0 |
| C7I | 1.0115(3) | 1.0771(8) | 0.3683(3) | 4.9 |
| C8 | 0.9395(3) | 0.6694(6) | 0.1923(2) | 2.8 |
| C9I | 0.8066(2) | 0.7119(6) | 0.1549(2) | 3.0 |
| C10 | 0.7168(3) | 0.6537(6) | 0.2361(2) | 3.0 |
| C11I | 0.5904(3) | 0.6128(6) | 0.1800(2) | 3.6 |
| C12 | 0.4988(3) | 0.5673(7) | 0.2582(3) | 4.0 |
| C13I | 0.5431(3) | 0.3895(7) | 0.3221(3) | 4.4 |
| C14I | 0.6661(3) | 0.4327(8) | 0.3806(3) | 4.6 |
| C15I | 0.7586(3) | 0.4774(7) | 0.3017(3) | 3.9 |
| C16I | 0.6579(3) | 0.6111(10) | 0.4508(3) | 5.2 |
| C17I | 0.6152(3) | 0.7864(8) | 0.3872(3) | 4.7 |
| C18I | 0.7064(3) | 0.8317(6) | 0.3082(3) | 4.0 |
| C19I | 0.4897(4) | 0.7420(9) | 0.3276(3) | 4.7 |

Unit cell parameters for the 1.33HCl salt form H1.67 saxagliptin are listed in Table 8:

TABLE 8

Unit Cell Parameters for the 1.33 HCl Salt Form H1.67-1

| Structure | T | a(Å) | b(Å) | c(Å) | α° | β° | γ° | Z' | SG |
|---|---|---|---|---|---|---|---|---|---|
| 1.33 HCl Form H1.67-1 | −50 | 7.0209(3) | 12.9804(4) | 16.8658(6) | 75.698(2) | 89.374(2) | 87.987(2) | 3 | P1 |

T = temp (° C.) for crystallographic data
Z' = number of drug molecules per asymmetric unit
SG = space group Table 8A below sets forth the positional parameters for the 1.33HCl salt form H1.67 at −50° C.:

TABLE 8A

Positional Parameters and their Estimated Standard Deviations for 1.33 HCl Salt Form H1.67 at −50° C.

| Atom | x | y | z | B(iso) |
|---|---|---|---|---|
| O8 | 0.0933(7) | 0.5768(3) | 0.1664(3) | 4.5 |
| O12 | −0.0165(5) | 0.7520(3) | −0.1478(2) | 3.2 |
| N1 | 0.2919(7) | 0.6658(4) | 0.2268(3) | 3.2 |
| N6 | −0.1131(11) | 0.8095(7) | 0.2456(5) | 7.4 |
| N9 | 0.3795(7) | 0.5214(3) | 0.0743(3) | 3.2 |
| C2I | 0.4594(9) | 0.7221(5) | 0.2384(4) | 4.1 |
| C3I | 0.4521(10) | 0.7359(5) | 0.3227(4) | 4.4 |
| C4I | 0.2771(11) | 0.6826(6) | 0.3644(4) | 5. |
| C5I | 0.1556(10) | 0.6631(5) | 0.2939(4) | 4.4 |
| C6 | 0.0023(11) | 0.7452(7) | 0.2678(5) | 5.0 |
| C7I | 0.4273(11) | 0.8304(5) | 0.2530(4) | 4.8 |
| C8 | 0.2468(9) | 0.6209(4) | 0.1651(3) | 3.1 |
| C9I | 0.3860(9) | 0.6268(4) | 0.0964(3) | 2.9 |
| C10 | 0.3395(8) | 0.7194(4) | 0.0192(3) | 2.6 |
| C11I | 0.1763(8) | 0.6939(4) | −0.0302(3) | 2.8 |
| C12 | 0.1352(8) | 0.7858(4) | −0.1046(3) | 2.6 |
| C13I | 0.3167(9) | 0.8029(5) | −0.1581(3) | 3.2 |
| C14I | 0.4785(9) | 0.8320(5) | −0.1108(3) | 3.5 |
| C15I | 0.4250(9) | 0.9328(5) | −0.0830(4) | 3.5 |
| C16I | 0.2500(10) | 0.9138(4) | −0.0301(4) | 3.7 |
| C17I | 0.2828(9) | 0.8214(5) | 0.0470(4) | 3.6 |
| C18I | 0.5179(8) | 0.7417(5) | −0.0352(3) | 3.4 |
| C19I | 0.0830(9) | 0.8852(4) | −0.0783(3) | 3.2 |
| O28 | 0.5390(6) | 0.3369(3) | 0.1765(2) | 3.3 |
| O32 | 0.4055(9) | 0.1674(6) | 0.4701(4) | 9.3 |
| N21 | 0.6437(6) | 0.2130(4) | 0.1126(3) | 2.7 |
| N26 | 0.2220(9) | 0.1005(6) | 0.1604(5) | 6.7 |
| N29 | 0.8927(7) | 0.3560(4) | 0.2320(3) | 3.3 |
| C22I | 0.4658(8) | 0.2213(5) | 0.0649(3) | 3.1 |
| C23I | 0.5213(9) | 0.1795(5) | −0.0100(3) | 3.7 |
| C24I | 0.7054(8) | 0.1155(5) | 0.0120(4) | 3.1 |
| C25I | 0.7806(8) | 0.1409(5) | 0.0888(4) | 3.4 |
| C26 | 0.3232(10) | 0.1551(6) | 0.1197(5) | 4.6 |
| C27I | 0.7129(9) | 0.0314(5) | 0.0918(4) | 4.0 |
| C28 | 0.6637(9) | 0.2705(5) | 0.1685(3) | 2.6 |
| C29I | 0.8338(8) | 0.2486(4) | 0.2244(3) | 26 |
| C30 | 0.7833(7) | 0.1725(4) | 0.3088(3) | 2.6 |
| C31I | 0.6131(9) | 0.2100(5) | 0.3506(4) | 3.7 |
| C32 | 0.5723(9) | 0.1315(6) | 0.4326(4) | 4.3 |
| C33I | 0.5312(12) | 0.0260(7) | 0.4166(4) | 5.6 |
| C34I | 0.6992(14) | −0.0160(5) | 0.3768(4) | 5.7 |
| C35I | 0.7428(11) | 0.0623(5) | 0.2951(4) | 4.7 |
| C36I | 0.9547(10) | 0.1583(6) | 0.3659(4) | 4.9 |
| C37I | 0.9130(9) | 0.0799(6) | 0.4475(4) | 4.7 |
| C38I | 0.7391(10) | 0.1229(5) | 0.4867(4) | 4.4 |
| C39I | 0.8722(12) | −0.0277(5) | 0.4320(4) | 6.1 |
| O48 | 0.8173(6) | 0.6372(3) | 0.7127(2) | 3.0 |
| O52 | 0.6456(5) | 0.2649(3) | 0.6916(2) | 3.0 |
| N41 | 1.1251(6) | 0.6582(3) | 0.6748(3) | 2.5 |
| N46 | 0.8983(9) | 0.6653(5) | 0.4968(4) | 5.4 |
| N49 | 0.9137(6) | 0.5310(3) | 0.8662(2) | 2.4 |
| C42I | 1.0684(8) | 0.7443(4) | 0.6040(3) | 2.8 |
| C43I | 1.2544(8) | 0.8006(5) | 0.5727(3) | 3.6 |
| C44I | 1.4132(9) | 0.7276(5) | 0.6141(4) | 3.6 |
| C45I | 1.3276(8) | 0.6409(4) | 0.6782(3) | 2.8 |
| C46 | 0.9718(9) | 0.7005(5) | 0.5436(4) | 3.2 |
| C47I | 1.4221(9) | 0.6159(5) | 0.6047(4) | 3.9 |
| C48 | 0.9831(9) | 0.6096(4) | 0.7251(3) | 2.3 |
| C49I | 1.0409(7) | 0.5166(4) | 0.7968(3) | 2.3 |
| C50 | 1.0236(7) | 0.4071(4) | 0.7777(3) | 2.5 |
| C51I | 0.8296(8) | 0.3912(5) | 0.7402(3) | 2.6 |
| C52 | 0.8281(7) | 0.2820(5) | 0.7218(3) | 2.3 |
| C53I | 0.8598(8) | 0.1960(4) | 0.8019(3) | 2.8 |
| C54I | 1.0498(8) | 0.2099(4) | 0.8377(3) | 2.6 |

TABLE 8A-continued

Positional Parameters and their Estimated Standard Deviations for 1.33 HCl Salt Form H1.67 at −50° C.

| Atom | x | y | z | B(iso) |
|---|---|---|---|---|
| C55I | 1.0537(8) | 0.3186(4) | 0.8564(3) | 2.6 |
| C56I | 1.1815(7) | 0.3949(4) | 0.7158(3) | 2.5 |
| C57I | 1.1785(8) | 0.2857(4) | 0.6978(3) | 2.7 |
| C58I | 0.9845(7) | 0.2716(4) | 0.6617(3) | 2.7 |
| C59I | 1.2096(8) | 0.1991(4) | 0.7773(3) | 3.2 |
| O72 | 0.6215(7) | 0.4873(4) | 0.2885(3) | 5.7 |
| O73 | 0.5691(5) | 0.0717(3) | 0.7075(2) | 4.0 |
| O74 | 0.3079(6) | 0.0502(3) | 0.6175(2) | 4.5 |
| O75 | 0.5570(7) | 0.3810(4) | 0.5403(3) | 6.0 |
| O76 | 0.8297(7) | 0.4880(4) | 0.4299(3) | 6.2 |
| Cl | 1.2187(3) | 0.39051(17) | 0.37871(18) | 8.0 |
| Cl1 | 0.0167(2) | 0.39767(12) | 0.04845(9) | 4.4 |
| Cl2 | 0.9267(2) | −0.04877(11) | 0.69278(9) | 3.8 |
| Cl3 | 0.48975(18) | 0.47499(11) | 0.90366(8) | 3.3 |
| H92 | 0.4473 | 0.4564 | 0.1212 | 4.1 |
| H93 | 0.2299 | 0.4976 | 0.0697 | 4.1 |
| H94 | 0.4477 | 0.5218 | 0.0163 | 4.1 |
| H291 | 1.0106 | 0.3462 | 0.2719 | 4.2 |
| H292 | 0.9295 | 0.4011 | 0.1712 | 4.2 |
| H293 | 0.7717 | 0.3925 | 0.2545 | 4.2 |
| H494 | 0.9708 | 0.4836 | 0.9236 | 3.4 |
| H492 | 0.8985 | 0.6108 | 0.8649 | 3.4 |
| H493 | 0.7723 | 0.4982 | 0.8581 | 3.4 |
| H521 | 0.6238 | 0.3157 | 0.6292 | 3.6 |
| H721 | 0.4789 | 0.4567 | 0.3076 | 3.6 |
| H722 | 0.6995 | 0.4868 | 0.3440 | 6.5 |
| H731 | 0.6955 | 0.0244 | 0.7032 | 6.5 |
| H732 | 0.5986 | 0.1522 | 0.7016 | 4.6 |
| H741 | 0.4353 | 0.0595 | 0.6636 | 4.6 |
| H742 | 0.1587 | 0.0684 | 0.6316 | 5.1 |
| H743 | 0.3444 | 0.0979 | 0.5590 | 5.1 |
| H751 | 0.6623 | 0.4212 | 0.4972 | 6.8 |
| H752 | 0.5078 | 0.3134 | 0.5179 | 6.8 |
| H761 | 0.9639 | 0.4557 | 0.4134 | 6.7 |
| H762 | 0.8537 | 0.5541 | 0.4558 | 6.7 |

Unit cell parameters for the saxagliptin HCl salt 0.75 equiv. H$_2$O form H0.75-3 are listed below in Table 9:

TABLE 9

Unit Cell Data for HCl Salt 0.75 equiv. H$_2$O Form H0.75-3

| Form | T | a(Å) | b(Å) | c(Å) | α° | β° | γ° | Z' | SG |
|---|---|---|---|---|---|---|---|---|---|
| HCl salt form H0.75.3 | 22 | 43.913(1) | 6.759(1) | 17.948(1) | 90 | 134.98 | 90 | 2 | C2 |

T = temp (° C.) for the crystallographic data
Z' = number of drug molecules per asymmetric unit
SG = space group Table 10 below sets forth the positional parameters for the HCl salt form H0.75-3 at 25° C.:

TABLE 10

Positional Parameters and Estimated Deviations for HCl Salt (0.75 equiv. H$_2$O) Form H.75-3 at rt

| Name | x | y | z | B(iso) | Occupancy* |
|---|---|---|---|---|---|
| CL1 | 0.1782 | 0.1571 | −0.0224 | 12.3 | |
| CL2 | 0.0720 | 0.3516 | 0.0202 | 14.2 | |
| O8 | 0.2851 | 0.4780 | 0.1856 | 9.7 | |
| O12 | 0.1292 | 0.7725 | 0.1572 | 21.8 | |
| O28 | −0.0377 | 0.7214 | −0.1424 | 12.8 | |
| O32 | 0.1241 | 0.7696 | −0.1265 | 11.0 | |
| O99 | 0.2393 | 0.7289 | −0.0243 | 12.5 | |
| O100 | 0.0000 | 0.1469 | 0.0000 | 9.6 | 0.5 |
| N1 | 0.3110 | 0.7884 | 0.2359 | 8.6 | |
| N6 | 0.3973 | 0.5579 | 0.4435 | 12.3 | |
| N9 | 0.2055 | 0.6135 | 0.0465 | 9.2 | |
| N21 | −0.0603 | 1.0022 | −0.2340 | 12.2 | |
| N26 | −0.1568 | 0.7817 | −0.4560 | 13.8 | |
| N29 | 0.0416 | 0.8097 | −0.0243 | 13.0 | |
| C2 | 0.3513 | 0.7025 | 0.2746 | 12.5 | |
| C3 | 0.3771 | 0.9001 | 0.2902 | 11.3 | |
| C4 | 0.3517 | 1.0597 | 0.2870 | 14.6 | |
| C5 | 0.3101 | 0.9998 | 0.2490 | 10.1 | |
| C6 | 0.3729 | 0.6130 | 0.3653 | 18.2 | |
| C7 | 0.3493 | 1.0651 | 0.3647 | 11.0 | |
| C8 | 0.2813 | 0.6573 | 0.1942 | 8.6 | |
| C9 | 0.2337 | 0.7232 | 0.1435 | 8.1 | |
| C10 | 0.2279 | 0.6932 | 0.2166 | 11.3 | |
| C11 | 0.1801 | 0.7376 | 0.1498 | 8.9 | |
| C12 | 0.1672 | 0.7269 | 0.2088 | 16.4 | |
| C13 | 0.2010 | 0.8873 | 0.3070 | 13.0 | |
| C14 | 0.2468 | 0.8461 | 0.3733 | 11.4 | |
| C15 | 0.2560 | 0.8467 | 0.3033 | 9.0 | |
| C16 | 0.2425 | 0.4941 | 0.2701 | 8.9 | |
| C17 | 0.2341 | 0.4742 | 0.3413 | 14.0 | |
| C18 | 0.1856 | 0.5564 | 0.2680 | 20.5 | |
| C19 | 0.2586 | 0.6607 | 0.4189 | 12.1 | |
| C22 | −0.1059 | 0.9741 | −0.2739 | 11.3 | |
| C23 | −0.1240 | 1.1865 | −0.2910 | 15.1 | |
| C24 | −0.0934 | 1.2981 | −0.2880 | 12.7 | |
| C25 | −0.0581 | 1.2109 | −0.2534 | 13.9 | |
| C26 | −0.1281 | 0.8818 | −0.3662 | 15.6 | |
| C27 | −0.0919 | 1.2741 | −0.3670 | 12.3 | |
| C28 | −0.0339 | 0.8602 | −0.1742 | 11.1 | |
| C29 | 0.0141 | 0.9006 | −0.1238 | 9.3 | |
| C30 | 0.0202 | 0.8334 | −0.1968 | 11.4 | |
| C31 | 0.0701 | 0.8472 | −0.1251 | 8.7 | |
| C32 | 0.0751 | 0.7709 | −0.1988 | 11.0 | |
| C33 | 0.0609 | 0.5718 | −0.2316 | 8.9 | |
| C34 | 0.0109 | 0.5724 | −0.3068 | 11.3 | |
| C35 | 0.0009 | 0.6297 | −0.2410 | 12.8 | |
| C36 | −0.0030 | 0.9877 | −0.2860 | 9.8 | |
| C37 | 0.0087 | 0.9363 | −0.3472 | 12.3 | |
| C38 | 0.0559 | 0.9192 | −0.2816 | 11.3 | |
| C39 | −0.0077 | 0.7333 | −0.3864 | 15.3 | |

*Occupancy is 1. unless otherwise noted.
Typical errors in coordinates (x, y, z) are .0003, 002, 001.

Unit cell parameters for the 1.25 hydrate HCl salt of saxagliptin free base (form H1.25) are substantially equal to the following listed in Table 11:

TABLE 11

Cell Dimensions from Single Crystal of HCl Salt Form H1.25-2

| Temperature | at −50° C. | at +22° C. |
|---|---|---|
| a(Å) | 31.198(8) Å | 31.290(4) Å |
| b(Å) | 6.860(1) Å | 6.880(1) Å |
| c(Å) | 19.652(6) Å | 19.706(3) Å |
| α° | 90 | 90 |
| β° | 114.98(2)° | 114.79(1)° |
| γ° | 90 | 90 |
| Space group | C2 | C2 |
| Molecules/asymmetric unit | 2 | 2 |

Where T = temp (° C.) for the crystallographic data
Z' = number of drug molecules per asymmetric unit
SG = space group and characterized by the positional parameters substantially as listed in Table 11A:

TABLE 11A

Positional Parameters and their Estimated Standard Deviations for HCl Salt (1.25 equiv. $H_2O$) Form H1.25-2 at −50° C.

| Atom | x | y | z | B(iso) | Occupancy* |
|---|---|---|---|---|---|
| CL1 | 0.24463(7) | 0.0334(4) | −0.0991(1) | 3.46(5) | |
| CL2 | 0.30720(6) | 0.0371(4) | 0.4947(1) | 2.67(4) | |
| O5 | 0.2814(2) | 0.100(1) | 0.3240(3) | 3.4(2) | |
| O8 | 0.3585(2) | −0.1671(9) | 0.0647(3) | 2.9(1) | |
| O38 | 0.1808(2) | 0.2215(8) | 0.3305(3) | 2.2(1) | |
| O42 | 0.0254(4) | 0.403(2) | 0.3263(6) | 2.9(3) | 0.5 |
| O44 | −0.0014(4) | −0.216(2) | 0.3054(6) | 3.2(3) | 0.5 |
| O90 | 0.0000 | 0.361 | 0.0000 | 5.3 | 0.35 |
| O98 | 0.2370(2) | −0.028(1) | 0.6218(3) | 3.9(2) | |
| O99 | 0.1979(2) | 0.148(1) | 0.0792(3) | 3.4(1) | |
| N1 | 0.3853(2) | 0.141(1) | 0.0690(3) | 2.3(1) | |
| N6 | 0.4913(3) | −0.064(2) | 0.1679(5) | 6.0(3) | |
| N9 | 0.2783(2) | −0.039(1) | 0.0707(3) | 2.2(2) | |
| N31 | 0.1640(2) | −0.085(1) | 0.2841(3) | 2.1(1) | |
| N36 | 0.0940(3) | 0.158(2) | 0.1238(4) | 6.2(3) | |
| N39 | 0.2031(2) | 0.098(1) | 0.4716(3) | 2.1(2) | |
| C2 | 0.4229(3) | 0.077(1) | 0.0473(4) | 2.8(2) | |
| C3 | 0.4389(3) | 0.262(2) | 0.0187(4) | 3.8(2) | |
| C4 | 0.4188(3) | 0.430(2) | 0.0459(4) | 3.3(2) | |
| C5 | 0.3842(3) | 0.354(1) | 0.0746(4) | 2.5(2) | |
| C6 | 0.4626(3) | −0.009(2) | 0.1153(5) | 4.1(3) | |
| C7 | 0.4304(3) | 0.445(2) | 0.1282(4) | 3.4(2) | |
| C8 | 0.3569(2) | 0.008(1) | 0.0781(3) | 2.4(2) | |
| C9 | 0.3227(2) | 0.075(1) | 0.1107(4) | 2.1(2) | |
| C10 | 0.3427(2) | 0.047(1) | 0.1971(3) | 1.8(2) | |
| C11 | 0.3024(2) | 0.080(1) | 0.2226(3) | 2.1(2) | |
| C12 | 0.3214(2) | 0.061(2) | 0.3075(4) | 2.5(2) | |
| C13 | 0.3594(3) | 0.218(2) | 0.3443(4) | 3.2(2) | |
| C14 | 0.3994(2) | 0.187(1) | 0.3210(4) | 2.4(2) | |
| C15 | 0.3811(3) | 0.204(1) | 0.2346(4) | 2.5(2) | |
| C16 | 0.3644(3) | −0.156(1) | 0.2238(4) | 2.6(2) | |
| C17 | 0.3823(3) | −0.175(1) | 0.3099(4) | 3.0(2) | |
| C18 | 0.4209(3) | −0.019(2) | 0.3464(4) | 3.2(2) | |
| C19 | 0.3422(3) | −0.140(1) | 0.3327(4) | 2.9(2) | |
| C32 | 0.1702(3) | −0.023(1) | 0.2162(4) | 2.7(2) | |
| C33 | 0.1787(3) | −0.220(2) | 0.1837(4) | 3.4(2) | |
| C34 | 0.1607(3) | −0.377(1) | 0.2172(4) | 2.8(2) | |
| C35 | 0.1532(3) | −0.292(1) | 0.2828(4) | 2.6(2) | |
| C36 | 0.1272(3) | 0.082(1) | 0.1639(4) | 3.5(2) | |
| C37 | 0.1119(3) | −0.361(1) | 0.2158(4) | 3.1(2) | |
| C38 | 0.1706(2) | 0.051(1) | 0.3382(3) | 2.0(2) | |
| C39 | 0.1655(2) | −0.013(1) | 0.4081(3) | 1.7(2) | |
| C40 | 0.1155(2) | 0.024(1) | 0.4041(4) | 2.1(2) | |
| C41 | 0.0951(3) | 0.222(1) | 0.3672(4) | 2.7(2) | |
| C42 | 0.0452(3) | 0.249(2) | 0.3655(5) | 3.6(2) | |
| C43 | 0.0135(3) | 0.089(2) | 0.3207(4) | 4.0(3) | |
| C44 | 0.0327(3) | −0.107(2) | 0.3559(4) | 3.3(2) | |
| C45 | 0.0364(3) | −0.111(2) | 0.4357(4) | 3.3(2) | |
| C46 | 0.0683(2) | 0.052(2) | 0.4813(4) | 2.9(2) | |
| C47 | 0.1176(2) | 0.025(2) | 0.4839(3) | 2.5(2) | |
| C48 | 0.0825(2) | −0.139(2) | 0.3587(4) | 3.0(2) | |
| C49 | 0.0490(3) | 0.250(2) | 0.4451(4) | 3.0(2) | |

*Occupancy is 1 unless otherwise noted

Unit cell parameters for the diHCl salt of saxagliptin (2 equiv. $H_2O$) (form H2-1) are substantially equal to the following listed in Table 12:

TABLE 12

Unit Cell Data for di HCL Salt Form H2-1

| Salt | Form | T (° C.) | a(Å) | b(Å) | c(Å) | α° | β° | γ° | Z' | sg |
|---|---|---|---|---|---|---|---|---|---|---|
| "2HCl" | H2-1 | −50 | 15.227(1) | 6.807(1) | 20.451(1) | 90 | 90 | 90 | 1 | $P2_12_12_1$ |

T = temp (° C.) for the crystallographic data
Z' = number of drug molecules per asymmetric unit
SG = space group and characterized by the positional parameters substantially as listed in Table 12A:

TABLE 12A

Positional Parameters and Estimated Deviations for DiHCl Salt (2 equiv. H$_2$O) Form H2-1 at −50° C.

| Atom | x | y | z | B Ciso |
|---|---|---|---|---|
| CL1 | 0.418457 | −0.409961 | 0.281265 | 5.9 |
| CL2 | 0.466819 | 0.152597 | 0.427700 | 7.1 |
| O8 | 0.255093 | −0.058678 | 0.350457 | 4.6 |
| O12 | 0.403289 | −0.010342 | 0.038751 | 4.7 |
| O98 | 0.349604 | −0.401552 | 0.422191 | 7.8 |
| O99 | 0.473173 | −0.255339 | 0.478620 | 5.9 |
| N1 | 0.194370 | 0.241827 | 0.340532 | 4.0 |
| N7 | −0.002269 | −0.001734 | 0.355406 | 7.7 |
| N9 | 0.398392 | 0.044827 | 0.286334 | 3.9 |
| C2 | 0.134083 | 0.198318 | 0.395869 | 4.9 |
| C3 | 0.109124 | 0.402007 | 0.422538 | 5.6 |
| C4 | 0.128126 | 0.548078 | 0.367818 | 5.3 |
| C5 | 0.185303 | 0.439024 | 0.317983 | 4.9 |
| C6 | 0.057542 | 0.083862 | 0.372894 | 5.0 |
| C8 | 0.251002 | 0.104285 | 0.322549 | 3.9 |
| C9 | 0.314652 | 0.146875 | 0.268040 | 3.9 |
| C10 | 0.281608 | 0.083493 | 0.199306 | 3.6 |
| C11 | 0.360315 | 0.062475 | 0.150831 | 4.5 |
| C12 | 0.327677 | 0.010845 | 0.082255 | 3.9 |
| C13 | 0.275886 | −0.187956 | 0.084592 | 5.3 |
| C14 | 0.197144 | −0.164201 | 0.130291 | 5.5 |
| C15 | 0.230540 | −0.112143 | 0.200613 | 4.3 |
| C16 | 0.221598 | 0.247276 | 0.171810 | 4.4 |
| C17 | 0.190889 | 0.195757 | 0.103571 | 5.4 |
| C18 | 0.270230 | 0.169368 | 0.057080 | 5.2 |
| C19 | 0.138776 | 0.003488 | 0.104051 | 6.0 |
| C20 | 0.092913 | 0.503918 | 0.301088 | 6.3 |

Unit cell parameters of the dihydrate of the HBr salt of saxagliptin free base form H2-1 are substantially equal to the following listed in Table 13:

TABLE 13

Cell Dimensions from Single Crystal of HBr Salt Form H2-1

| Temperature ° C. | at −50° C. | at +22° C. |
|---|---|---|
| a(Å) | 11.120(1) Å | 11.073(7) Å |
| b(Å) | 6.888(1) Å | 6.877(1) Å |
| c(Å) | 12.993(1) Å | 13.029(5) Å |
| α° | 90 | 90 |
| β° | 94.60(1)° | 94.74(4)° |
| γ° | 90 | 90 |
| Space group | P2$_1$ | P2$_1$ |
| Molecules/asymmetric unit | 1 | 1 |

T = temp (° C.) for the crystallographic data
Z' = number of drug molecules per asymmetric unit
SG = space group and characterized by the positional parameters substantially as listed in Table 14:

TABLE 14

Positional Parameters and their Estimated Standard Deviations for HBr Salt (2 equiv. H$_2$O) Form H2-1 at −50° C.

| Atom | x | y | z | B(iso) |
|---|---|---|---|---|
| Br | 0.71123(5) | 0.15800(13) | 0.02085(5) | 5.1 |
| O1 | 0.9828(3) | 0.5122(6) | 0.1795(3) | 3.7 |
| O2 | 0.3904(4) | 0.5272(9) | 0.2131(3) | 5.6 |
| O3 | 0.5883(4) | 0.6751(12) | −0.0857(3) | 6.0 |
| O4 | 0.9882(5) | 0.7470(10) | −0.0259(4) | 6.4 |
| N1 | 1.0117(4) | 0.8153(8) | 0.2383(4) | 3.6 |
| N2 | 0.7868(4) | 0.6159(7) | 0.0575(3) | 3.6 |

TABLE 14-continued

Positional Parameters and their Estimated Standard Deviations for HBr Salt (2 equiv. H$_2$O) Form H2-1 at −50° C.

| Atom | x | y | z | B(iso) |
|---|---|---|---|---|
| N3 | 1.1706(6) | 0.5715(12) | 0.4333(6) | 6.2 |
| C1 | 0.8097(4) | 0.7222(9) | 0.1597(4) | 3.3 |
| C2 | 0.7620(6) | 0.4793(12) | 0.3024(5) | 4.5 |
| C3 | 0.5049(5) | 0.5760(11) | 0.2661(5) | 4.3 |
| C4 | 0.7211(4) | 0.6633(13) | 0.2402(3) | 3.3 |
| C5 | 0.9432(4) | 0.6779(11) | 0.1928(3) | 3.3 |
| C6 | 1.1571(5) | 0.6590(15) | 0.3606(5) | 4.6 |
| C7 | 1.0160(6) | 1.0798(13) | 0.3667(6) | 5.7 |
| C8 | 0.9839(5) | 1.0156(10) | 0.2598(5) | 4.5 |
| C9 | 0.5944(4) | 0.6228(10) | 0.1858(4) | 3.8 |
| C10 | 0.6607(6) | 0.6068(14) | 0.4542(5) | 5.4 |
| C11 | 0.6191(6) | 0.7889(13) | 0.3938(5) | 4.9 |
| C12 | 0.5470(5) | 0.3989(12) | 0.3253(5) | 4.8 |
| C13 | 1.2030(5) | 0.9743(11) | 0.2723(5) | 4.5 |
| C14 | 1.1409(5) | 0.7703(10) | 0.2639(4) | 3.9 |
| C15 | 1.1022(6) | 1.1157(9) | 0.2856(6) | 4.9 |
| C16 | 0.4968(6) | 0.7501(13) | 0.3362(5) | 5.2 |
| C17 | 0.6707(5) | 0.4361(13) | 0.3828(5) | 5.0 |
| C18 | 0.7124(6) | 0.8319(12) | 0.3150(5) | 4.5 |

Unit cell parameters of the monohydrate of the HBr salt of saxagliptin free base form H1-2 (also referred to as form T1H2) are substantially equal to the following as listed in Table 15:

TABLE 15

Cell Dimensions from Single Crystal of HBr Salt Form H1-2 (22° C.)

| a(Å) | 23.30(1) Å |
|---|---|
| b(Å) | 6.77(1) Å |
| c(Å) | 12.90(1) Å |
| α° | 90 |
| β° | 102.2(1)° |
| γ° | 90 |
| Space group | C2 |
| Molecules/asymmetric unit | 1 | and characterized by the positional parameters substantially as listed in Table 16:

TABLE 16

Positional Parameters and their Estimated Standard Deviations for Saxagliptin HBr Salt (1 equiv. H$_2$O) Form H1-2 at rt

| Atom | x | y | z | B(iso) |
|---|---|---|---|---|
| BR | 0.1177(1) | 0.1905(8) | −0.0409(2) | 9.14(7) |
| O2 | −0.057 | 0.7678 | 0.143(1) | 8.4(5) |
| O4 | 0.2390(8) | 0.786(2) | −0.030(1) | 10.7(6) |
| O11 | 0.2337(8) | 0.544(2) | 0.184(1) | 8.5(5) |
| N1 | 0.2517(8) | 0.851(3) | 0.238(1) | 6.0(5) |
| N2 | 0.1407(7) | 0.673(4) | 0.036(1) | 7.4(4) |
| N3 | 0.325(1) | 0.614(3) | 0.461(2) | 11.6(7) |
| C1 | 0.1522(9) | 0.770(2) | 0.142(1) | 5.0(6) |
| C2 | 0.111(1) | 0.497(2) | 0.246(2) | 7.4(7) |
| C3 | 0.0016(9) | 0.742(3) | 0.208(1) | 5.8(6) |
| C4 | 0.1085(7) | 0.733(3) | 0.210(1) | 4.1(5) |
| C5 | 0.2161(8) | 0.724(3) | 0.189(1) | 5.5(5) |
| C6 | 0.3223(9) | 0.687(6) | 0.380(2) | 9.4(6) |
| C7 | 0.261(1) | 1.128(3) | 0.364(2) | 8.0(7) |
| C8 | 0.242(1) | 1.059(3) | 0.250(2) | 6.6(6) |
| C9 | 0.0464(9) | 0.763(3) | 0.142(1) | 6.1(7) |
| C10 | 0.076(1) | 0.637(4) | 0.399(2) | 8.8(7) |
| C11 | 0.073(1) | 0.843(3) | 0.371(2) | 7.1(7) |
| C12 | 0.004(1) | 0.514(3) | 0.242(2) | 8.3(7) |
| C13 | 0.346(1) | 1.001(3) | 0.296(2) | 7.3(7) |
| C14 | 0.316(1) | 0.800(3) | 0.280(2) | 6.5(7) |
| C15 | 0.303(1) | 1.146(4) | 0.292(2) | 9.3(7) |

TABLE 16-continued

Positional Parameters and their Estimated Standard Deviations for Saxagliptin HBr Salt (1 equiv. H₂O) Form H1-2 at rt

| Atom | x | y | z | B(iso) |
|------|---|---|---|--------|
| C16 | 0.013(1) | 0.857(4) | 0.300(2) | 10.0(8) |
| C17 | 0.062(1) | 0.477(3) | 0.313(2) | 8.7(7) |
| C18 | 0.119(1) | 0.849(3) | 0.303(2) | 6.7(6) |

Unit cell parameters of hemihydrate of the R—H-tartrate salt of saxagliptin free base form H.5-1 are substantially equal to the following as listed in Table 17:

TABLE 17

Cell Dimensions of Single Crystal of Tartrate Salt Form H.5-1 (−173° C.)

| a(Å) | 7.070(1) Å |
|------|------------|
| b(Å) | 16.400(1) Å |
| c(Å) | 19.640(1) Å |
| α° | 90 |
| β° | 97.69(2)° |
| γ° | 90 |
| Space group | P2₁ |
| Molecules/asymmetric unit | 2 | and characterized by the positional parameters substantially as listed in Table 18:

TABLE 18

Positional Parameters for R-H-Tartrate (1:1) Salt (0.5 equiv. H₂O) Form H.5-1 at −173° C.

| Atom | x | y | z | U | B(iso) | Occupancy* |
|------|---|---|---|---|--------|------------|
| O1 | 0.536(3) | −0.0069(14) | 0.1780(9) | 0.063(6) | 5.5 | |
| O2 | 0.508(3) | 0.0667(13) | 0.0780(9) | 0.065(6) | 5.8 | |
| O3 | 1.167(3) | 0.0834(12) | 0.0814(8) | 0.052(5) | 4.5 | |
| O4 | 1.218(3) | 0.1414(14) | 0.1867(10) | 0.071(6) | 5.7 | |
| O5 | 0.902(3) | −0.0206(12) | 0.1878(8) | 0.053(5) | 4.2 | |
| O6 | 0.842(3) | 0.1490(14) | 0.1953(10) | 0.074(7) | 4.5 | |
| C1 | 0.900(4) | 0.1131(19) | 0.1363(13) | 0.047(8) | 4.0 | |
| C2 | 0.595(4) | 0.028(2) | 0.1304(14) | 0.055(9) | 4.9 | |
| C3 | 0.814(4) | 0.0262(16) | 0.1309(12) | 0.036(7) | 3.1 | |
| C4 | 1.114(4) | 0.1111(19) | 0.1365(13) | 0.046(8) | 4.2 | |
| O7 | 0.503(3) | −0.0979(12) | 0.4322(8) | 0.053(5) | 3.0 | |
| O8 | 0.460(3) | −0.1321(13) | 0.3210(9) | 0.061(6) | 4.8 | |
| O9 | −0.154(3) | −0.0674(12) | 0.4308(8) | 0.046(5) | 4.8 | |
| O10 | −0.203(3) | −0.0035(13) | 0.3302(9) | 0.059(6) | 4.0 | |
| O11 | 0.157(3) | 0.0142(12) | 0.3234(8) | 0.049(5) | 3.4 | |
| O12 | 0.097(3) | −0.1608(13) | 0.3214(9) | 0.059(6) | 4.4 | |
| C5 | 0.115(4) | −0.0302(16) | 0.3801(11) | 0.030(7) | 5.9 | |
| C6 | −0.107(4) | −0.0310(18) | 0.3814(13) | 0.041(8) | 3.4 | |
| C7 | 0.189(4) | −0.1187(18) | 0.3784(13) | 0.042(7) | 4.4 | |
| C8 | 0.403(4) | −0.1191(19) | 0.3748(13) | 0.040(7) | 4.8 | |
| O13 | 0.634(3) | 0.4395(13) | 0.4448(9) | 0.059(6) | 4.9 | |
| O14 | 0.452(3) | 0.0974(12) | 0.4304(8) | 0.057(5) | 3.3 | |
| N1 | 0.486(3) | 0.1009(15) | 0.2961(10) | 0.052(6) | 4.6 | |
| N2 | 0.763(4) | 0.1234(17) | 0.4620(11) | 0.057(7) | 6.9 | |
| N3 | 0.559(4) | 0.1768(19) | 0.6021(13) | 0.076(8) | 3.6 | |
| C9 | 0.606(5) | 0.1640(18) | 0.3445(13) | 0.053(8) | 3.2 | |
| C10 | 0.958(5) | 0.147(2) | 0.4544(15) | 0.068(10) | 2.9 | |
| C11 | 1.033(4) | 0.210(2) | 0.5087(14) | 0.063(9) | 2.4 | |
| C12 | 1.080(4) | 0.1200(18) | 0.5191(12) | 0.046(8) | 2.3 | |
| C13 | 0.752(4) | 0.087(2) | 0.5297(12) | 0.049(8) | 2.0 | |
| C14 | 0.968(4) | 0.075(2) | 0.5602(14) | 0.071(10) | 2. | |
| C15 | 0.644(5) | 0.142(3) | 0.5691(18) | 0.084(11) | 2.4 | |
| C16 | 0.525(4) | 0.2501(18) | 0.3385(12) | 0.041(8) | 4.2 | |
| C17 | 0.606(4) | 0.1210(19) | 0.4158(13) | 0.050(8) | 5.5 | |
| C18 | 0.323(4) | 0.388(2) | 0.3912(12) | 0.051(8) | 5.0 | |
| C19 | 0.263(5) | 0.373(2) | 0.2653(15) | 0.071(10) | 3.2 | |
| C20 | 0.614(5) | 0.3044(19) | 0.3967(14) | 0.053(8) | 3.4 | |
| C21 | 0.538(4) | 0.3916(18) | 0.3909(12) | 0.041(8) | 5.0 | |
| C22 | 0.579(5) | 0.426(2) | 0.3224(15) | 0.080(11) | 7.7 | |
| C23 | 0.298(4) | 0.2497(19) | 0.3384(14) | 0.051(8) | 2.3 | |
| C24 | 0.226(5) | 0.338(2) | 0.3301(16) | 0.077(11) | 4.7 | |
| C25 | 0.568(5) | 0.285(2) | 0.2680(17) | 0.083(11) | 2.7 | |
| C26 | 0.474(4) | 0.375(2) | 0.2626(14) | 0.055(8) | 3.8 | |
| O15 | 0.095(5) | −0.450(2) | 0.0391(14) | 0.062(10) | 4.2 | .6 |
| O16 | 0.051(3) | −0.1146(13) | 0.0560(9) | 0.062(6) | 1.9 | |
| N4 | 0.242(3) | −0.1155(16) | 0.1928(10) | 0.052(6) | 4.8 | |
| N5 | 0.335(4) | −0.1342(15) | 0.0278(12) | 0.056(7) | 2.6 | |
| N6 | 0.103(5) | −0.189(2) | −0.1309(16) | 0.102(10) | 6.4 | |
| C27 | 0.086(5) | −0.398(2) | 0.0957(15) | 0.071(10) | 6.0 | |
| C28 | 0.186(5) | −0.311(2) | 0.0869(10) | 0.069(10) | 3. | |
| C29 | 0.279(5) | −0.178(2) | 0.1398(14) | 0.067(10) | 5.1 | |
| C30 | 0.287(4) | −0.3039(18) | 0.2132(13) | 0.050(8) | 4.7 | |
| C31 | −0.103(7) | −0.333(3) | 0.171(2) | 0.105(14) | 3.0 | |
| C32 | 0.198(5) | −0.438(3) | 0.1584(15) | 0.083(11) | 3.3 | |
| C33 | 0.182(4) | −0.389(2) | 0.2236(14) | 0.056(9) | 7.0 | |
| C34 | −0.020(4) | −0.378(2) | 0.2325(14) | 0.068(10) | 7.0 | |

TABLE 18-continued

Positional Parameters for R-H-Tartrate (1:1) Salt (0.5 equiv. H₂O)
Form H.5-1 at −173° C.

| Atom | x | y | z | U | B(iso) | Occupancy* |
|---|---|---|---|---|---|---|
| C35 | 0.284(5) | −0.090(2) | −0.0396(15) | 0.068(9) | 2.8 | |
| C36 | 0.475(5) | −0.064(2) | −0.0633(15) | 0.067(10) | 4.0 | |
| C37 | 0.538(5) | −0.152(2) | 0.0329(15) | 0.066(10) | 49 | |
| C38 | 0.616(5) | −0.115(3) | −0.0287(16) | 0.084(11) | 5.1 | |
| C39 | 0.173(6) | −0.146(3) | −0.0887(19) | 0.090(12) | 3.9 | |
| C40 | 0.600(6) | −0.207(3) | −0.0265(18) | 0.092(12) | 7.2 | |
| C41 | −0.039(4) | −0.2497(18) | 0.1573(13) | 0.042(7) | 7.7 | |
| C42 | 0.180(3) | −0.2611(17) | 0.1499(12) | 0.035(7) | 6.2 | |
| C43 | −0.121(5) | −0.388(3) | 0.1049(17) | 0.085(11) | 2.7 | |
| C44 | 0.222(5) | −0.1390(19) | 0.0710(14) | 0.051(9) | 2.7 | |
| O17 | −0.244(3) | −0.2368(14) | 0.3270(10) | 0.078(7) | 6.8 | |
| O18 | −0.264(7) | −0.325(3) | 0.1782(19) | 0.042(12) | 4.5 | .4 |

*Occupancy is 1 unless otherwise indicated.

Unit cell parameters of trihydrate of the ammonium sulfate salt of saxagliptin free base form H3-1 are substantially equal to the following as listed in Table 19:

TABLE 19

Cell Dimensions for Single Crystal of NH₄SO₄ Salt Form H3-1

| | |
|---|---|
| a(Å) | 31.671(1) |
| b(Å) | 6.685(1) |
| c(Å) | 11.394(1) |
| α° | 90 |
| β° | 103.15(1) |
| γ° | 90 |
| Space group | C2 |
| Molecules/asymmetric unit | 1 | wherein said crystalline form is at about −50° C.;
and characterized by the positional parameters substantially as listed in Table 20:

TABLE 20

Parameters and their Estimated Standard Deviations for Saxagliptin NH₄SO₄ Form H3-1 at −50° C.

| Atom | x | y | z | B(iso) |
|---|---|---|---|---|
| S1 | 0.48811(6) | 0.3495(2) | 0.71956(15) | 2.8 |
| O1 | 0.37298(13) | 0.0587(7) | −0.0036(4) | 4.4 |
| O2 | 0.38873(14) | −0.0239(7) | 0.5967(4) | 3.9 |
| O3 | 0.49478(17) | 0.1651(7) | 0.6557(4) | 5.0 |
| O4 | 0.45477(17) | 0.4694(8) | 0.6446(5) | 6.9 |
| O5 | 0.52806(17) | 0.4600(8) | 0.7518(5) | 7.9 |
| O6 | 0.4767(2) | 0.2863(9) | 0.8300(5) | 8.8 |
| O7 | 0.43992(19) | −0.3342(7) | 0.4236(5) | 6.1 |
| O8 | 0.43945(18) | 0.7829(7) | 1.0075(5) | 6.9 |
| O9 | 0.43281(14) | 0.3651(9) | 0.9999(4) | 5.3 |
| N1 | 0.35771(16) | 0.2771(7) | 0.6000(5) | 2.9 |
| N2 | 0.2768(2) | 0.0354(11) | 0.6943(6) | 6.7 |
| N3 | 0.43534(15) | 0.0810(7) | 0.4449(4) | 2.9 |
| N4 | 0.47367(19) | 0.8340(10) | 0.8042(5) | 5.7 |
| C1 | 0.39311(9) | 0.1889(9) | 0.4328(6) | 2.7 |
| C2 | 0.3482(2) | 0.2353(10) | 0.7169(6) | 2.8 |
| C3 | 0.32530(19) | 0.2964(9) | 0.2863(6) | 3.3 |
| C4 | 0.3041(2) | 0.5539(11) | 0.5618(6) | 4.2 |
| C5 | 0.3506(2) | 0.0743(10) | 0.0934(6) | 3.1 |
| C6 | 0.3597(2) | 0.1319(8) | 0.3154(6) | 2.4 |
| C7 | 0.3173(2) | 0.2404(10) | 0.0653(6) | 3.6 |
| C8 | 0.3821(2) | 0.1174(9) | 0.2102(5) | 2.8 |
| C9 | 0.3791(2) | 0.1399(11) | 0.5496(6) | 3.1 |
| C10 | 0.3497(2) | 0.4856(9) | 0.5662(7) | 3.8 |
| C11 | 0.3449(2) | 0.4406(9) | 0.7740(6) | 3.7 |
| C12 | 0.3048(2) | −0.1103(11) | 0.2046(6) | 4.1 |
| C13 | 0.2928(2) | 0.2536(11) | 0.1676(7) | 4.3 |
| C14 | 0.3394(2) | 0.5875(10) | 0.6724(7) | 3.9 |
| C15 | 0.2707(2) | 0.0546(12) | 0.1789(7) | 5.4 |
| C16 | 0.3284(2) | −0.1233(11) | 0.1026(6) | 4.2 |
| C17 | 0.3369(2) | −0.0659(10) | 0.3243(6) | 3.8 |
| C18 | 0.3080(3) | 0.1218(11) | 0.7017(7) | 4.1 |

Unit cell parameters of the nitrate salt of saxagliptin free base form N-1 are substantially equal to the following as listed in Table 21:

TABLE 21

Cell Dimensions for Single Crystal of NO₃ Salt Form N-1

| | |
|---|---|
| a(Å) | 20.615(1) |
| b(Å) | 25.214(1) |
| c(Å) | 7.034(1) |
| α° | 90 |
| β° | 90 |
| γ° | 90 |
| Space group | P2₁2₁2₁ |
| Molecules/asymmetric unit | 2 | wherein said crystalline form is at about +22° C.;
and characterized by the positional parameters substantially as listed in Table 22:

TABLE 22

Positional Parameters and their Estimated Standard Deviations for Saxagliptin NO₃ Salt Form N-1 at rt

| Atom | x | y | z | B(iso) | Occupancy* |
|---|---|---|---|---|---|
| O8 | 0.3665(3) | 0.6025(3) | 0.1025(8) | 2.7 | |
| O12 | 0.2122(9) | 0.7856(8) | −0.301(2) | 3.0 | .4 |
| O17 | 0.2394(6) | 0.7652(5) | 0.3142(14) | 2.8 | .6 |
| N1 | 0.3828(4) | 0.6346(4) | −0.1931(9) | 1.6 | |
| N6 | 0.4655(8) | 0.7313(7) | 0.031(2) | 9.4 | |
| N9 | 0.2500(4) | 0.5613(4) | 0.0288(10) | 2.9 | |
| C2 | 0.4519(6) | 0.6435(5) | −0.1547(13) | 2.6 | |
| C3 | 0.4850(6) | 0.6487(6) | −0.3496(14) | 4.1 | |
| C4 | 0.4316(6) | 0.6507(5) | −0.4947(15) | 3.4 | |
| C5 | 0.3666(5) | 0.6403(5) | −0.3933(13) | 3.0 | |
| C6 | 0.4581(7) | 0.6922(7) | −0.0510(17) | 4.1 | |
| C7 | 0.3823(6) | 0.6925(6) | −0.4764(17) | 4.0 | |
| C8 | 0.3450(5) | 0.6137(5) | −0.0558(16) | 2.8 | |
| C9 | 0.2721(5) | 0.6079(4) | −0.0924(12) | 2.4 | |

TABLE 22-continued

Positional Parameters and their Estimated Standard Deviations for Saxagliptin NO₃ Salt Form N-1 at rt

| Atom | x | y | z | B(iso) | Occupancy* |
|---|---|---|---|---|---|
| C10 | 0.2322(5) | 0.6582(4) | −0.0512(12) | 1.8 | |
| C11 | 0.2401(6) | 0.6986(5) | −0.2182(14) | 3.4 | |
| C12 | 0.1990(7) | 0.7473(6) | −0.1856(17) | 5.1 | |
| C13 | 0.1284(6) | 0.7335(6) | −0.1676(15) | 3.9 | |
| C14 | 0.1191(6) | 0.6967(5) | 0.0006(15) | 4.3 | |
| C15 | 0.1584(5) | 0.6464(5) | −0.0330(15) | 2.9 | |
| C16 | 0.2557(5) | 0.6873(5) | 0.1310(13) | 2.7 | |
| C17 | 0.2148(6) | 0.7392(5) | 0.1579(14) | 3.7 | |
| C18 | 0.1433(6) | 0.7233(6) | 0.1807(15) | 3.6 | |
| C19 | 0.2228(7) | 0.7754(6) | 0.0000(17) | 5.3 | |
| O38 | 0.55437(11) | 0.56464(11) | 0.0297(3) | 2.9 | |
| O42 | 0.70684(11) | 0.37772(11) | 0.2278(3) | 5.4 | |
| N31 | 0.59216(11) | 0.55956(11) | 0.3267(3) | 1.9 | |
| N36 | 0.72993(11) | 0.57610(11) | 0.0735(3) | 4.5 | |
| N39 | 0.44852(11) | 0.50578(11) | 0.1143(3) | 2.3 | |
| C32 | 0.63616(11) | 0.60331(11) | 0.2963(3) | 2.5 | |
| C33 | 0.66017(11) | 0.62226(11) | 0.4935(3) | 2.7 | |
| C34 | 0.64334(11) | 0.57436(11) | 0.6213(3) | 2.7 | |
| C35 | 0.59818(11) | 0.53819(11) | 0.5216(3) | 2.2 | |
| C36 | 0.68942(11) | 0.58887(11) | 0.1730(3) | 3.2 | |
| C37 | 0.66793(11) | 0.52355(11) | 0.5756(3) | 3.0 | |
| C38 | 0.55466(11) | 0.54298(11) | 0.1871(3) | 2.0 | |
| C39 | 0.51353(11) | 0.49436(11) | 0.2101(3) | 2.2 | |
| C40 | 0.54263(11) | 0.44157(11) | 0.1442(3) | 2.3 | |
| C41 | 0.61409(11) | 0.43535(11) | 0.2185(3) | 2.2 | |
| C42 | 0.64150(11) | 0.38343(11) | 0.1577(3) | 3.9 | |
| C43 | 0.60269(11) | 0.33743(11) | 0.2334(3) | 4.2 | |
| C44 | 0.53162(11) | 0.33921(11) | 0.1638(3) | 7.0 | |
| C45 | 0.50174(11) | 0.39585(11) | 0.2228(3) | 4.1 | |
| C46 | 0.64441(11) | 0.38193(11) | −0.0569(3) | 3.3 | |
| C47 | 0.57635(11) | 0.38669(11) | −0.1324(3) | 4.1 | |
| C48 | 0.54676(11) | 0.43804(11) | −0.0778(3) | 4.3 | |
| C49 | 0.53618(11) | 0.34465(11) | −0.0638(3) | 6.2 | |
| O86 | 0.2597(4) | 0.4249(4) | −0.0703(9) | 4.2 | |
| O87 | 0.3634(5) | 0.4048(5) | −0.0721(13) | 6.0 | |
| O88 | 0.3255(3) | 0.4597(4) | 0.1317(10) | 2.9 | |
| N89 | 0.3167(6) | 0.4283(5) | −0.0074(15) | 3.3 | |
| O96 | 0.4477(4) | 0.5205(3) | −0.3048(8) | 3.0 | |
| O97 | 0.3452(3) | 0.5124(3) | −0.2451(9) | 3.3 | |
| O98 | 0.3827(4) | 0.4882(4) | −0.5147(9) | 4.4 | |
| N99 | 0.3911(5) | 0.5066(4) | −0.3563(13) | 3.3 | |

*Occupancy is 1. unless otherwise indicated.

Unit cell parameters of the tetrahydrate of saxagliptin fumarate (2:1) salt of the free base form H4-1 are substantially equal to the following as listed in Table 23:

TABLE 23

Cell Dimensions for Single Crystal of Fumarate Salt Form H4-1

| | |
|---|---|
| a(Å) | 11.429(1) |
| b(Å) | 26.979(2) |
| c(Å) | 6.803(2) |
| α° | 90 |
| β° | 90.32(2) |
| γ° | 90 |
| Space group | P2₁ |
| Molecules/asymmetric unit | 2 | wherein said crystalline form is at about +22° C.;
and characterized by the positional parameters substantially as listed in Table 24:

TABLE 24

Positional Parameters and their Estimated Standard Deviations for (2:1) Saxagliptin Fumarate Salt (4 equiv. H₂O) Form H4-1 at +22° C.

| Atom | x | y | z | B(iso) |
|---|---|---|---|---|
| O2 | 0.923(1) | −0.0925(5) | 1.116(2) | 3.1(3) |
| O3 | 0.332(1) | −0.0867(5) | 1.237(2) | 3.2(3) |
| O8 | 0.184(1) | −0.0070(5) | 0.526(2) | 3.8(3) |
| O9 | 0.160(1) | 0.0090(5) | 0.843(2) | 4.5(3) |
| O10 | 0.618(1) | −0.0018(5) | 0.466(2) | 2.9(3) |
| O11 | 0.593(1) | 0.0232(5) | 0.772(2) | 3.3(3) |
| O20 | 0.803(1) | 0.0495(5) | 0.943(2) | 4.0(3) |
| O30 | 0.284(1) | 0.0269(5) | 1.178(2) | 3.2(3) |
| O32 | −0.360(1) | 0.1133(5) | 0.254(2) | 3.9(3) |
| O31 | 0.234(1) | 0.1184(6) | 0.395(2) | 5.9(4) |
| O40 | −0.054(1) | −0.0247(6) | 0.820(2) | 4.6(3) |
| O50 | −0.033(1) | −0.0243(5) | 0.410(2) | 3.9(3) |
| N1 | 0.305(1) | −0.1155(5) | 0.927(2) | 2.0(3) |
| N2 | 0.164(2) | −0.2076(8) | 1.170(3) | 6.4(5) |
| N4 | 0.503(1) | −0.0214(6) | 1.108(2) | 2.3(3) |
| N31 | −0.385(1) | 0.1403(6) | 0.559(2) | 2.7(3) |
| N32 | −0.522(2) | 0.2368(8) | 0.329(3) | 6.9(6) |
| N33 | −0.193(1) | 0.0526(6) | 0.355(2) | 2.5(3) |
| C2 | 0.336(2) | −0.1246(7) | 0.723(3) | 2.7(4) |
| C3 | 0.220(2) | −0.1381(7) | 0.626(3) | 2.9(5) |
| C4 | 0.125(2) | −0.1315(8) | 0.771(3) | 3.3(5) |
| C5 | 0.185(2) | −0.1268(8) | 0.970(3) | 3.2(5) |
| C6 | 0.310(2) | −0.1768(8) | 0.666(3) | 3.2(5) |
| C7 | 0.177(2) | −0.1720(8) | 1.089(3) | 4.1(5) |
| C8 | 0.374(2) | −0.0907(7) | 1.073(3) | 3.0(4) |
| C9 | 0.493(2) | −0.0739(6) | 1.020(3) | 1.8(4) |
| C10 | 0.590(2) | −0.1106(7) | 1.081(3) | 3.1(5) |
| C11 | 0.597(2) | −0.1524(7) | 0.941(3) | 2.6(4) |
| C12 | 0.699(2) | −0.1900(8) | 0.996(3) | 3.6(5) |
| C13 | 0.681(2) | −0.2062(9) | 1.198(3) | 4.7(6) |
| C14 | 0.681(2) | −0.1661(8) | 1.344(3) | 4.1(5) |
| C15 | 0.796(2) | −0.1373(8) | 1.328(3) | 3.9(5) |
| C16 | 0.811(2) | −0.1184(7) | 1.128(3) | 2.7(4) |
| C17 | 0.713(2) | −0.0821(7) | 1.067(2) | 2.1(4) |
| C18 | 0.811(2) | −0.1603(8) | 0.977(3) | 3.9(5) |
| C19 | 0.582(2) | −0.1290(8) | 1.297(3) | 3.6(5) |
| C32 | −0.354(2) | 0.1493(7) | 0.766(3) | 2.9(4) |
| C33 | −0.466(2) | 0.1630(8) | 0.864(3) | 4.1(5) |
| C341 | −0.568(2) | 0.1563(8) | 0.710(3) | 3.7(5) |
| C34 | −0.5700 | 0.1563 | 0.7110 | 3 |
| C351 | −0.507(2) | 0.1542(8) | 0.518(3) | 3.2(4) |
| C35 | −0.5069 | 0.1539 | 0.5178 | 3 |
| C361 | −0.517(2) | 0.1995(8) | 0.405(3) | 4.1(5) |
| C36 | −0.5172 | 0.1992 | 0.4063 | 4 |
| C37 | −0.006(2) | 0.234(1) | 0.310(4) | 6.7(7) |
| C37 | −0.0060 | 0.2345 | 0.3081 | 6 |
| C38 | 0.007(2) | 0.2149(9) | 0.521(4) | 5.3(6) |
| C38 | 0.0067 | 0.2146 | 0.5231 | 5 |
| C39 | −0.196(2) | 0.1000(7) | 0.468(3) | 2.1(4) |
| C39 | −0.1949 | 0.1001 | 0.4684 | 2 |
| C40 | 0.124(2) | 0.1446(8) | 0.376(3) | 3.7(5) |
| C41 | 0.024(2) | 0.1076(7) | 0.421(3) | 2.7(4) |
| C42 | 0.112(2) | 0.1639(8) | 0.177(3) | 4.5(5) |
| C43 | −0.094(2) | 0.1790(9) | 0.554(3) | 4.6(5) |
| C50 | 0.221(2) | 0.0080(7) | 0.688(3) | 3.3(5) |
| C51 | 0.350(1) | 0.0171(7) | 0.704(2) | 1.8(4) |
| C52 | 0.426(1) | −0.0019(7) | 0.596(2) | 1.6(4) |
| C53 | 0.556(2) | 0.0043(7) | 0.609(3) | 3.2(5) |

Unit cell parameters of the trifluoroacetate salt of saxagliptin free base form N-1 are substantially equal to the following as listed in Table 25:

TABLE 25

Cell Dimensions for Single Crystal of TFA Salt Form N-1

| | |
|---|---|
| a(Å) | 11.631(2) |
| b(Å) | 6.599(1) |
| c(Å) | 13.838(1) |
| α° | 90 |
| β° | 104.24(1) |

TABLE 25-continued

Cell Dimensions for Single Crystal of TFA Salt Form N-1

| | |
|---|---|
| γ° | 90 |
| Space group | P2$_1$ |
| Molecules/asymmetric unit | 1 | wherein said crystalline form is at about 22° C.;

and characterized by the positional parameters substantially as listed in Table 26:

TABLE 26

Positional Parameters and their Estimated Standard Deviations for Saxagliptin TFA Salt Form N-1 at +22° C.

| Atom | x | y | z | B(iso) | Occupancy* |
|---|---|---|---|---|---|
| F1 | 0.405(4) | 0.467(9) | 0.447(3) | 12. | 0.70 |
| F2 | 0.421(3) | 0.448(13) | 0.606(3) | 10.8 | 0.70 |
| F3 | 0.381(3) | 0.703(5) | 0.525(4) | 16. | 0.70 |
| F4 | 0.419(8) | 0.537(8) | 0.647(6) | 3.8 | 0.30 |
| F5 | 0.409(7) | 0.55(2) | 0.484(8) | 4.7 | 0.30 |
| F6 | 0.397(4) | 0.289(7) | 0.535(4) | 4.6 | 0.30 |
| O3 | −0.2377(13) | 0.6123(19) | −0.0322(11) | 10.0 | |
| O12 | −0.0227(9) | 0.8792(18) | 0.3590(8) | 4.2 | |
| O221 | 0.1774(12) | 0.633(2) | 0.5200(8) | 5.3 | |
| O222 | 0.1830(12) | 0.317(2) | 0.4768(9) | 5.9 | |
| N1 | −0.0760(10) | 0.5072(19) | 0.4301(9) | 3.3 | |
| N13 | 0.1088(16) | 0.730(2) | 0.2863(11) | 4.3 | |
| N20 | 0.029(2) | 1.120(3) | 0.1287(16) | 7.0 | |
| C1 | −0.1808(16) | 0.522(3) | 0.2446(11) | 3.0 | |
| C2I | −0.1521(15) | 0.574(2) | 0.1440(13) | 3.3 | |
| C3 | −0.2619(19) | 0.561(3) | 0.0619(13) | 4.5 | |
| C4I | −0.3561(16) | 0.714(2) | 0.0778(14) | 5.2 | |
| C5I | −0.387(2) | 0.663(3) | 0.1746(16) | 4.0 | |
| C6I | −0.4361(18) | 0.444(3) | 0.1727(13) | 4.5 | |
| C7I | −0.345(2) | 0.303(3) | 0.1514(14) | 4.3 | |
| C8I | −0.2358(18) | 0.307(2) | 0.2358(15) | 3.2 | |
| C9I | −0.2761(19) | 0.678(2) | 0.2570(16) | 3.1 | |
| C10I | −0.3110(15) | 0.351(3) | 0.0569(15) | 3.8 | |
| C11I | −0.0626(16) | 0.533(2) | 0.3227(14) | 3.2 | |
| C12 | 0.011(2) | 0.722(3) | 0.3262(12) | 3.6 | |
| C14I | 0.1629(19) | 0.566(3) | 0.2483(15) | 5.2 | |
| C15I | 0.277(2) | 0.657(3) | 0.2280(17) | 5.4 | |
| C16I | 0.2881(16) | 0.863(4) | 0.2591(15) | 7.0 | |
| C17I | 0.164(2) | 0.927(3) | 0.2796(14) | 4.7 | |
| C18I | 0.1736(18) | 0.599(2) | 0.1422(14) | 6.7 | |
| C19 | 0.089(2) | 1.039(4) | 0.1957(19) | 4.4 | |
| C222 | 0.232(2) | 0.478(4) | 0.5081(14) | 4.8 | |
| C223 | 0.366(3) | 0.492(7) | 0.530(5) | 9.9 | |

*Occupancy is 1 unless otherwise indicated.

Unit cell parameters of the dihydrate of the trifluoroacetate salt of saxagliptin free base form H2-2 are substantially equal to the following as listed in Table 27:

TABLE 27

Cell Dimensions for Single Crystal of TFA Salt Form H2-2

| | |
|---|---|
| a(Å) | 11.935(2) |
| b(Å) | 7.665(2) |
| c(Å) | 13.386(1) |
| α° | 90 |
| β° | 114.61(1) |
| γ° | 90 |
| Space group | P2$_1$ |
| Molecules/asymmetric unit | 1 | wherein said crystalline form is at about 22° C.;

and characterized by the positional parameters substantially as listed in Table 28:

TABLE 28

Table of Positional Parameters and their Estimated Standard Deviations for Saxagliptin TFA Salt (2 equiv. H$_2$O) Form H2-2 at rt

| Atom | x | y | z | B(iso) | Occupancy* |
|---|---|---|---|---|---|
| F34 | 0.0501(9) | 0.212(2) | 0.2248(8) | 9.3(2) | .5 |
| F35 | 0.0360(7) | 0.156(1) | 0.3866(6) | 7.4(2) | .5 |
| F36 | 0.083(1) | −0.040(2) | 0.2958(9) | 5.0(2) | .25 |
| F37 | 0.066(1) | 0.005(2) | 0.256(1) | 6.5(3) | .25 |
| F38 | 0.026(1) | 0.275(2) | 0.256(1) | 5.8(3) | .25 |
| F39 | 0.056(2) | 0.053(4) | 0.401(2) | 11.1(5) | .25 |
| F40 | 0.078(2) | 0.128(4) | 0.197(2) | 11.7(5) | .25 |
| F41 | 0.073(1) | −0.036(3) | 0.326(1) | 7.8(3) | .25 |
| F42 | 0.017(2) | 0.220(3) | 0.337(1) | 14.9(5) | .5 |
| O2 | 0.1952(5) | 0.004(1) | 0.6707(6) | 3.8(2) | |
| O10 | 0.5602(5) | 0.1994(9) | 0.6059(4) | 2.3(1) | |
| O30 | 0.3073(5) | 0.062(1) | 0.3994(5) | 3.0(1) | |
| O32 | 0.2513(5) | 0.3359(9) | 0.4180(4) | 2.4(1) | |
| O98 | 0.0651(7) | 0.568(1) | 0.4256(8) | 6.1(3) | |
| O99 | 0.2838(6) | 0.799(1) | 0.5441(5) | 3.6(1) | |
| N1 | 0.7053(5) | 0.2515(9) | 0.7757(5) | 1.6(1) | |
| N2 | 0.4548(5) | 0.512(1) | 0.5880(5) | 1.7(1) | |
| N8 | 0.694(1) | −0.183(1) | 0.8269(7) | 5.4(2) | |
| C2 | 0.7751(7) | 0.100(1) | 0.7695(7) | 2.3(2) | |
| C3 | 0.9109(7) | 0.136(1) | 0.8501(7) | 3.0(2) | |
| C4 | 0.9056(7) | 0.288(1) | 0.9179(7) | 2.9(2) | |
| C5 | 0.7780(7) | 0.360(1) | 0.8703(6) | 2.4(2) | |
| C6 | 0.8251(8) | 0.269(2) | 0.9794(6) | 3.6(2) | |
| C7 | 0.7276(8) | −0.059(1) | 0.8024(7) | 3.0(2) | |
| C9 | 0.5973(6) | 0.288(1) | 0.6903(6) | 1.7(2) | |
| C11 | 0.5185(6) | 0.435(1) | 0.7021(5) | 1.4(1) | |
| C13 | 0.4264(6) | 0.369(1) | 0.7470(6) | 1.6(1) | |
| C14 | 0.4991(6) | 0.314(1) | 0.8678(6) | 2.2(2) | |
| C15 | 0.4098(7) | 0.253(2) | 0.9183(6) | 3.1(2) | |
| C16 | 0.3345(7) | 0.096(1) | 0.8507(7) | 3.3(2) | |
| C17 | 0.2618(7) | 0.152(1) | 0.7325(6) | 2.3(2) | |
| C18 | 0.1762(7) | 0.300(1) | 0.7272(7) | 2.7(2) | |
| C19 | 0.2490(7) | 0.456(1) | 0.7921(6) | 2.6(2) | |
| C20 | 0.3383(7) | 0.517(1) | 0.7443(6) | 2.2(2) | |
| C21 | 0.3506(7) | 0.211(1) | 0.6837(6) | 2.0(2) | |
| C22 | 0.3219(7) | 0.401(2) | 0.9127(6) | 3.2(2) | |
| C31 | 0.2326(7) | 0.184(1) | 0.3851(6) | 2.2(2) | |
| C33 | 0.0982(7) | 0.133(1) | 0.3228(7) | 2.9(2) | |

*Occupancy is 1 unless otherwise indicated.

Unit cell parameters of the hemihydrate of the trifluoroacetate salt of saxagliptin free base form H0.5-1 are substantially equal to the following as listed in Table 29:

TABLE 29

Cell Dimensions for Single Crystal of TFA Salt Form H0.5-1

| Temperature ° C. | +22 | −50 |
|---|---|---|
| a(Å) | 22.266(3) | 22.3403(6) |
| b(Å) | 25.318(3) | 25.1636(7) |
| c(Å) | 7.012(1) | 6.9951(2) |
| α° | 90 | 90 |
| β° | 90 | 90 |
| γ° | 90 | 90 |
| Space group | P2$_1$2$_1$2 | P2$_1$2$_1$2 |
| Molecules/asymmetric unit | 2 | 2 | and characterized by the positional parameters substantially as listed in Table 30:

TABLE 30

Positional Parameters and their Estimated Standard Deviations for Saxagliptin Hemi TFA Salt (0.5 equiv. H$_2$O) Form H.5-1 at −50° C.

| Atom | x | y | z | B(iso) |
|---|---|---|---|---|
| F1 | −0.0054 | 0.4187 | 1.0399 | 5.2 |
| F2 | −0.0103 | 0.4083 | 1.2863 | 5.2 |

TABLE 30-continued

Positional Parameters and their Estimated Standard
Deviations for Saxagliptin Hemi TFA Salt (0.5 equiv.
H₂O) Form H.5-1 at −50° C.

| Atom | x | y | z | B(iso) |
|---|---|---|---|---|
| F3 | 0.0449 | 0.3562 | 1.1295 | 5.2 |
| O8 | 0.2064 | 0.5418 | 0.6621 | 4.5 |
| O12 | 0.4308 | 0.5433 | 0.6973 | 2.6 |
| O38 | 0.2316 | 0.4085 | 0.7647 | 4.0 |
| O42 | 0.4487 | 0.4369 | 0.7156 | 3.5 |
| O100 | 0.1098 | 0.4733 | 1.0214 | 10.3 |
| O101 | 0.1020 | 0.4350 | 1.3198 | 13.2 |
| O200 | 0.0611 | 0.4838 | 0.6754 | 25.8 |
| N1 | 0.1538 | 0.6055 | 0.8051 | 2.8 |
| N6 | 0.1984 | 0.6681 | 0.3934 | 8.0 |
| N9 | 0.2210 | 0.4941 | 1.0046 | 2.9 |
| N31 | 0.1779 | 0.3437 | 0.6240 | 3.5 |
| N36 | 0.2222 | 0.2849 | 1.0434 | 7.0 |
| N39 | 0.2366 | 0.4552 | 0.3908 | 2.8 |
| C2 | 0.1246 | 0.6179 | 0.6338 | 4.4 |
| C3 | 0.0705 | 0.6586 | 0.6860 | 6.6 |
| C4 | 0.0881 | 0.6790 | 0.9000 | 4.9 |
| C5 | 0.1421 | 0.6397 | 0.9679 | 4.2 |
| C6 | 0.1669 | 0.6481 | 0.5157 | 6.2 |
| C7 | 0.1494 | 0.6982 | 0.9223 | 5.7 |
| C8 | 0.1920 | 0.5676 | 0.7945 | 4.4 |
| C9 | 0.2261 | 0.5544 | 0.9914 | 3.2 |
| C10 | 0.2950 | 0.5698 | 0.9951 | 3.5 |
| C11 | 0.3321 | 0.5453 | 0.8357 | 2.9 |
| C12 | 0.3985 | 0.5675 | 0.8466 | 1.7 |
| C13 | 0.4261 | 0.5540 | 1.0280 | 3.5 |
| C14 | 0.3888 | 0.5815 | 1.1884 | 3.1 |
| C15 | 0.3229 | 0.5628 | 1.1975 | 3.1 |
| C16 | 0.3857 | 0.6436 | 1.1669 | 5.8 |
| C17 | 0.3590 | 0.6565 | 0.9659 | 4.0 |
| C18 | 0.2989 | 0.6347 | 0.9521 | 2.8 |
| C19 | 0.4009 | 0.6267 | 0.8094 | 3.3 |
| C32 | 0.1467 | 0.3299 | 0.8027 | 2.6 |
| C33 | 0.0992 | 0.2926 | 0.7383 | 4.9 |
| C34 | 0.1139 | 0.2721 | 0.5498 | 4.5 |
| C35 | 0.1619 | 0.3098 | 0.4631 | 5.4 |
| C36 | 0.1896 | 0.3029 | 0.9219 | 5.3 |
| C37 | 0.1727 | 0.2490 | 0.5188 | 5.5 |
| C38 | 0.2192 | 0.3844 | 0.6192 | 4.0 |
| C39 | 0.2457 | 0.3999 | 0.4236 | 3.3 |
| C40 | 0.3190 | 0.3845 | 0.4300 | 3.3 |
| C41 | 0.3541 | 0.4182 | 0.5696 | 3.4 |
| C42 | 0.4188 | 0.4033 | 0.5635 | 2.3 |
| C43 | 0.4425 | 0.4167 | 0.3744 | 4.7 |
| C44 | 0.4092 | 0.3779 | 0.2268 | 4.3 |
| C45 | 0.3429 | 0.3965 | 0.2286 | 2.9 |
| C46 | 0.4124 | 0.3236 | 0.2791 | 4.5 |
| C47 | 0.3899 | 0.3122 | 0.4578 | 5.1 |
| C48 | 0.3238 | 0.3224 | 0.4743 | 3.5 |
| C49 | 0.4279 | 0.3444 | 0.6266 | 2.4 |
| C100 | 0.0907 | 0.4446 | 1.1468 | 22.7 |
| C101 | 0.0390 | 0.4064 | 1.1122 | 20.6 |

Unit cell parameters of the hydrated saxagliptin H1 salt, which is the H2-1 form, containing 2 equiv. H₂O are substantially equal to the following as listed in Table 31:

TABLE 31

Cell Dimensions for Single Crystal of HI Salt Form H2-1

| Temperature ° C. | (at −20° C.) |
|---|---|
| a(Å) | 11.267(1) |
| b(Å) | 7.006(4) |
| c(Å) | 13.22(2) |
| α° | 90 |
| β° | 93.96(9) |
| γ° | 90 |
| Space group | P2₁ |
| Molecules/asymmetric unit | 1 |

Unit cell parameters of the monohydrate benzoate salt of saxagliptin free base form H-1 containing 1 equiv. H₂O are substantially equal to the following as listed in Table 32:

TABLE 32

Cell Dimensions of Saxagliptin Benzoate
Form H-1 from Single Crystal

| Temperature ° C. | at −40° C. | at +22° C. |
|---|---|---|
| a(Å) | 6.4065(2) | 6.4316(2) |
| b(Å) | 16.9843(4) | 17.0611(4) |
| c(Å) | 21.2504(5) | 21.3010(5) |
| α° | 90 | 90 |
| β° | 90 | 90 |
| γ° | 90 | 90 |
| Space group | P2₁2₁2₁ | P2₁2₁2₁ |
| Molecules/asymmetric unit | 1 | 1 | and characterized by the positional parameters substantially as listed in Table 33:

TABLE 33

Fractional Coordinates and their Estimated Standard Deviations
for Saxagliptin Benzoate (1 equiv. H₂O) Form H-1 at rt

| Atom | x | y | z | B(iso) |
|---|---|---|---|---|
| O12 | 0.4867(5) | −0.1695(1) | 0.4950(1) | 5. |
| O8 | 0.1654(4) | 0.1369(1) | 0.4802(1) | 3.2 |
| O20 | 0.7617(4) | 0.2501(1) | 0.3904(1) | 3.9 |
| O21 | 0.4326(4) | 0.2753(1) | 0.4145(1) | 3.6 |
| O99 | 0.0995(4) | −0.1969(1) | 0.4406(1) | 5.7 |
| N1 | 0.3221(5) | 0.0971(1) | 0.3920(1) | 3.0 |
| N6 | −0.0524(6) | −0.0404(2) | 0.3893(2) | 6.1 |
| N9 | 0.5479(5) | 0.1930(1) | 0.5227(1) | 2.6 |
| C2 | 0.1191(6) | 0.0938(2) | 0.3602(1) | 3.4 |
| C3 | 0.1718((7) | 0.0991(2) | 0.2894(2) | 4.6 |
| C4 | 0.3987(7) | 0.0799(3) | 0.2837(2) | 4.6 |
| C5 | 0.4926(6) | 0.0817(2) | 0.3489(1) | 3.5 |
| C6 | 0.0200(7) | 0.0182(3) | 0.3765(2) | 4.0 |
| C7 | 0.4790(7) | 0.0058(2) | 0.3130(2) | 5.1 |
| C8 | 0.3259(6) | 0.1183(2) | 0.4529(1) | 2.6 |
| C9 | 0.5322(6) | 0.1162(2) | 0.4883(1) | 2.5 |
| C10 | 0.5460(5) | 0.0447(2) | 0.5326(2) | 2.7 |
| C11 | 0.5009(6) | −0.0306(2) | 0.4941(1) | 3.1 |
| C12 | 0.5283(6) | −0.1031(2) | 0.5350(2) | 3.5 |
| C13 | 0.7502(6) | −0.1071(1) | 0.5611(2) | 3.7 |
| C14 | 0.7918(5) | −0.0340(2) | 0.6004(2) | 3.4 |
| C15 | 0.7698(5) | 0.0396(2) | 0.5591(2) | 3.0 |
| C16 | 0.3914(5) | 0.0480(2) | 0.5880(1) | 3.3 |
| C17 | 0.4155(6) | −0.0260(2) | 0.6287(2) | 3.5 |
| C18 | 0.6387(6) | −0.0303(2) | 0.6549(1) | 3.8 |
| C19 | 0.3732(6) | −0.1004(2) | 0.5892(1) | 3.9 |
| C20 | 0.5796(7) | 0.2698(2) | 0.3758(2) | 3.1 |
| C22 | 0.5287(7) | 0.2832(2) | 0.3073(1) | 3.4 |
| C23 | 0.6836(7) | 0.2728(2) | 0.2632(1) | 5.1 |
| C24 | 0.639(1) | 0.2806(3) | 0.1992(2) | 6.8 |
| C25 | 0.439(1) | 0.2993(3) | 0.1804(1) | 7.5 |
| C26 | 0.284(1) | 0.3108(3) | 0.2249(1) | 6.6 |
| C27 | 0.329(1) | 0.3023(3) | 0.2885(1) | 4.7 |

Utilities and Combinations

A. Utilities

The compounds of the present invention possess activity as an inhibitor of dipeptidyl peptidase-4 (DPP4), and therefore may be used in the treatment of diseases or disorders associated with DPP4 activity.

Accordingly, a compound of the present invention can be administered to mammals, preferably humans, for the treatment of a variety of conditions and disorders, including, but not limited to, treating or delaying the progression or onset of diabetes (including Type I and Type II, impaired glucose tolerance, insulin resistance, and diabetic complications, such as nephropathy, retinopathy, neuropathy and cataracts), hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension. The compound of the present invention may also be utilized to increase the blood levels of high density lipoprotein (HDL).

In addition, the conditions, diseases, and maladies collectively referenced to as "Syndrome X" or Metabolic Syndrome as detailed in Johannsson, *J. Clin. Endocrinol. Metab.*, 82:727-734 (1997), may be treated employing the compound of the present invention.

The crystalline saxagliptin salts, hydrates, solvates and the free base thereof of the invention may be administered in dosage forms and in dosages as disclosed in U.S. Pat. No. 6,395,767, the disclosure of which in its entirety is incorporated herein by reference.

B. Combinations

The present invention includes within its scope pharmaceutical compositions comprising, as an active ingredient, a therapeutically effective amount of a compound of formula I, alone or in combination with a pharmaceutical carrier or diluent. Optionally, the compound of the present invention can be utilized as an individual treatment, or utilized in combination with one or more other therapeutic agent(s).

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents and appetite suppressants.

Examples of suitable anti-diabetic agents for use in combination with the compound of the present invention include DPP4 inhibitors (e.g., vildagliptin or sitagliptin), biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, and dipeptidyl peptidase IV (DPP4) inhibitors and SGLT-2 inhibitors.

It is believed that the use of the compound of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Wellcome's faraglitazar (GI-262570), englitazone (CP-68722, Pfizer) or darglitazone (CP-86325, Pfizer, isaglitazone (MIT/J&J), reglitazar (JTT-501) (JPNT/P&U), rivoglitazone (R-119702) (Sankyo/WL), liraglutide (N,N-2344) (Dr. Reddy/NN), or (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include muraglitazar, peliglitazar, tesaglitazar AR-H039242 Astra/Zeneca, GW-501516 (Glaxo-Wellcome), KRP297 (Kyorin Merck) as well as those disclosed by Murakami et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", *Diabetes*, 47:1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors include vildagliptin, sitagliptin, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38(36):11597-11603 (1999), TSL-225 (tryptophyl-1,2,3,4-tetrahydroisoquinoline-3-carboxylic acid (disclosed by Yamada et al., *Bioorg. & Med. Chem. Leu.*, 8:1537-1540 (1998)), 2-cyanopyrrolidides and 4-cyanopyrrolidides, as disclosed by Ashworth et al., *Bioorg. & Med. Chem. Lett.*, 6(22):1163-1166 and 2745-2748 (1996), the compounds disclosed in U.S. application Ser. No. 10/899,641, WO 01/68603 and U.S. Pat. No. 6,395,767, employing dosages as set out in the above references.

Other suitable meglitinides include nateglinide (Novartis) or KAD1229 (PF/Kissei).

Suitable SGLT-2 inhibitors for use in combination with the compounds of the invention are described in U.S. Pat. Nos. 6,414,126 and 6,515,117 and include dapagliflozin.

Examples of suitable anti-hyperglycemic agents for use in combination with the compound of the present invention include glucagon-like peptide-1 (GLP-1) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fabric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as subutramine, tetrahydrolipostatin, dexfenfluramine, axokine, torcetrapib (CP-529414, Pfizer) and JTT-705 (Akros Pharma)), PPAR agonists (as described above) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686, 104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al., $J.$ $Med.$ $Chem.,$ 31(10):1869-1871 (1988), including isoprenoid (phosphinyl-methyl)phosphonates, as well as other known squalene synthetase inhibitors, for example, as disclosed in U.S. Pat. Nos. 4,871,721 and 4,924,024 and in Biller, S. A. et al., $Current$ $Pharmaceutical$ $Design,$ 2:1-40 (1996).

In addition, other squalene synthetase inhibitors suitable for use herein include the terpenoid pyrophosphates disclosed by Ortiz de Montellano, P. et al., $J.$ $Med.$ $Chem.,$ 20:243-249 (1977), the farnesyl diphosphate analog A and presqualene pyrophosphate (PSQ-PP) analogs as disclosed by Corey et al., $J.$ $Am.$ $Chem.$ $Soc.,$ 98:1291-1293 (1976), phosphinylphosphonates reported by McClard, R. W. et al., $J.$ $Am.$ $Chem.$ $Soc.,$ 109:5544 (1987) and cyclopropanes reported by Capson, T. L., Ph.D., dissertation, June, 1987, Dept. Med. Chem. U of Utah, Abstract, Table of Contents, pp. 16, 17, 40-43, 48-51, Summary.

The fabric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283, 546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in $Drugs$ $of$ $the$ $Future,$ 24:9-15 (1999), (Avasimibe); Nicolosi et al., "The ACAT inhibitor, Cl-1011 is effective in the prevention and regression of aortic fatty streak area in hamsters", $Atherosclerosis$ (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", $Cardiovasc.$ $Drug$ $Rev.,$ 16(1):16-30 (1998); Smith, C. et al., "RP 73163: a bioavailable alkylsulfinyl-diphenylimidazole ACAT inhibitor", $Bioorg.$ $Med.$ $Chem.$ $Lett.,$ 6(1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", $Curr.$ $Med.$ $Chem.,$ 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", $Chemtracts:$ $Org.$ $Chem.,$ 8(6):359-362 (1995), or TS-962 (Taisho Pharmaceutical Co. Ltd).

The hypolipidemic agent may be an up-regulator of LD2 receptor activity, such as 1(3H)-isobenzofuranone,3-(13-hydroxy-10-oxotetradecyl)-5,7-dimethoxy-(MD-700, Taisho Pharmaceutical Co. Ltd) and cholestan-3-ol,4-(2-propenyl)-(3a,4a,5a)-(LY295427, Eli Lilly).

Examples of suitable cholesterol absorption inhibitor for use in combination with the compound of the invention include SCH48461 (Schering-Plough), as well as those disclosed in $Atherosclerosis,$ 115:45-63 (1995) and $J.$ $Med.$ $Chem.,$ 41:973 (1998).

Examples of suitable ileal $Na^+$/bile acid co-transporter inhibitors for use in combination with the compound of the invention include compounds as disclosed in $Drugs$ $of$ $the$ $Future,$ 24:425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", $Brit.$ $J.$ $Pharmacology,$ 120:1199-1206 (1997), and Cornicelli et al., "15-Lipoxygenase and its Inhibition: A Novel Therapeutic Target for Vascular Disease", $Current$ $Pharmaceutical$ $Design,$ 5:11-20 (1999).

Examples of suitable anti-hypertensive agents for use in combination with the compound of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO 97/21993 (U. Cal SF), WO 99/00353 (KaroBio) and WO 00/039077 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physicians' Desk Reference, as in the patents set out above or as otherwise determined by one of ordinary skill in the art.

In carrying out the method of the invention, a pharmaceutical composition will be employed containing a crystalline saxagliptin form of the invention, with or without another antidiabetic agent and/or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 1 and 300 mg per day, preferably between 2 and 100 mg/day, more preferably between 2 and 50 mg/day such as 2.5 mg/day, 5 mg/day or 10 mg/day, which can be administered in a single dose or in the form of individual doses from 1 to 4 times per day.

A typical capsule for oral administration contains a crystalline saxagliptin form of the invention (10 mg), lactose (75 mg) and magnesium stearate (15 mg). The mixture is passed through a 60 mesh sieve and packed into a No. 1 gelatin capsule.

A typical injectable preparation is produced by aseptically placing 10 mg of a crystalline saxagliptin form of the invention into a vial, aseptically freeze-drying and sealing. For use, the contents of the vial are mixed with 2 mL of physiological saline, to produce an injectable preparation.

What is claimed is:

1. A method for treating diabetes, insulin resistance, hyperglycemia, dyslipidemia or elevated blood levels of free fatty acids or glycerol, obesity, Syndrome X, dysmetabolic syndrome, retinopathy, neuropathy, nephropathy, cataracts, hypertriglyceridemia, hyperinsulinemia, atherosclerosis, impaired glucose homeostasis, impaired glucose tolerance, infertility, polycystic ovary syndrome, arthritis, allograft rejection in transplantation, scleroderma, multiple sclerosis, necrotizing enteritis, microvillus inclusion disease, celiac disease, inflammatory bowel syndrome, anorexia nervosa, osteoporosis, lupus erythematosis, psoriasis, Crohn's disease, or ulcerative colitis, which comprises administering to a mammalian species in need of treatment or an effective amount of a crystalline compound in a form selected from H2-1 (1HCl), H2-1 (2HCl), H0.75-3, H1.67-1, P-5, N-3, H-1 (1H$_2$O), H-1 (1PhCO$_2$H/1H$_2$O), N-1, and mixtures thereof, wherein the crystalline compound of form H2-1 (1HCl) has structure

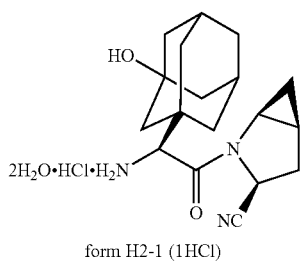

form H2-1 (1HCl)

and has powder x-ray diffraction peaks at 2θ values (CuKα λ−1.5418 Å) of 6.8±0.1, 11.1±0.1, 13.7±0.1, 14.6±0.1, 15.2±0.1, 16.4±0.1, 17.0±0.1, 20.2±0.1, and 21.1 ±0.1;

wherein the crystalline compound of form H2-1 (2HCl) has structure

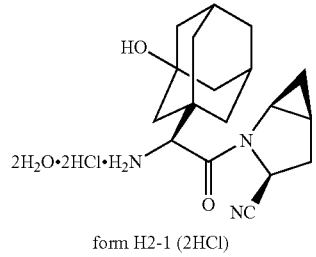

form H2-1 (2HCl)

and has powder x-ray diffraction peaks at 2θ values (CuKα λ−1.5418 Å) of 7.2±0.1, 8.6±0.1, 11.6±0.1, 14.3±0.1, 15.7±0.1, 19.5±0.1, and 22.5±0.1;

wherein the crystalline compound of form H0.75-3 has structure

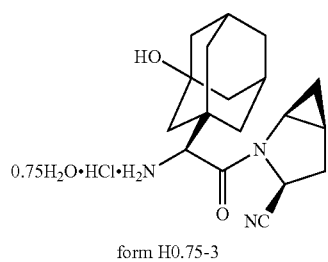

form H0.75-3 and has powder x-ray diffraction peaks at 2θ values (CuKα λ−1.5418 Å) of 5.0±0.1, 7.0±0.1, 8.1±0.1, 11.4±0.1, 13.4±0.1, 14.0±0.1, 14.5±0.1, 18.6±0.1, 19.4±0.1, and 20.0±0.1;

wherein the crystalline compound of form H1.67-1 has structure

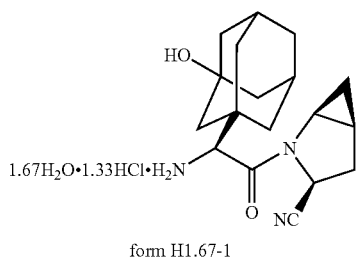

form H1.67-1 and has powder x-ray diffraction peaks at 2θ values (CuKα λ–1.5418 Å) of 5.4±0.1, 7.0±0.1, 13.8±0.1, 14.2±0.1, 14.6±0.1, 16.1±0.1, 16.6±0.1, 18.6±0.1, 19.0±0.1, and 20.3±0.1;

wherein the crystalline compound of form P-5 has structure

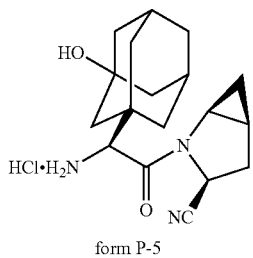

form P-5 and has powder x-ray diffraction peaks at 2θ values (CuKα λ–1.5418 Å) of 6.2±0.1, 10.7±0.1, 14.5±0.1, 15.0±0.1, 15.6±0.1, 16.2±0.1, 18.1±0.1, 18.7±0.1, and 21.1 ±0.1;

wherein the crystalline compound of form N-3 has structure

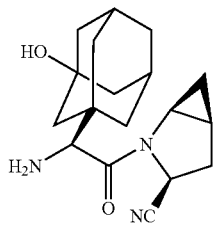

and has powder x-ray diffraction peaks at 2θ values (CuKα λ–1.5418 Å) of 5.2±0.1, 7.9±0.1, 10.8±0.1, 11.5±0.1, 13.0±0.1, 14.6±0.1, 15.6±0.1, 15.9±0.1, and 16.5±0.1;

wherein the crystalline compound of form H-1 (1H₂O) has structure

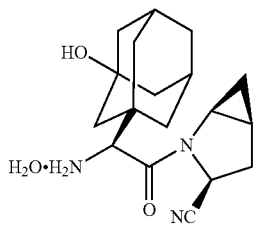

and has powder x-ray diffraction peaks at 2θ values (CuKα λ–1.5418 Å) of 12.4±0.1, 13.3±0.1, 13.6±0.1, 14.7±0.1, 16.2±0.1, 18.2±0.1, 19.9±0.1, 20.9±0.1, 21.9 ±0.1, and 22.4±0.1;

wherein the crystalline compound of form H-1 (1PhCO₂H/ 1H₂O) has structure

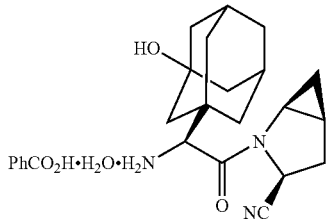

and has powder x-ray diffraction peaks at 2θ values (CuKα λ–1.5418 Å) of 6.6±0.1, 8.3±0.1, 15.3±0.1, 16.1±0.1, 16.9±0.1, 17.5±0.1, 17.8±0.1, 18.6±0.1, and 21.3±0.1; and wherein the crystalline compound of form N-1 has structure

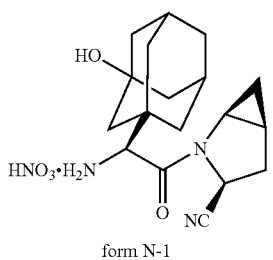

form N-1 and has powder x-ray diffraction peaks at 2θ values (CuKα λ–1.5418 Å) of 5.5±0.1, 7.0±0.1, 11.1±0.1, 14.4±0.1, 15.1±0.1, 15.7±0.1, 16.4±0.1, 16.8±0.1, and 19.6±0.1, alone or in combination with a therapeutic agent.

2. The method according to claim 1, wherein the method is a method for treating type II diabetes.

3. The method according to claim 1, wherein the crystalline compound is in a form selected from H2-1 (1HCl), H2-1 (2HCl), H0.75-3, H1.67-1, P-5, and mixtures thereof.

4. The method according to claim 3, wherein the crystalline compound is in a form H2-1 (1HCl).

Figure 6:
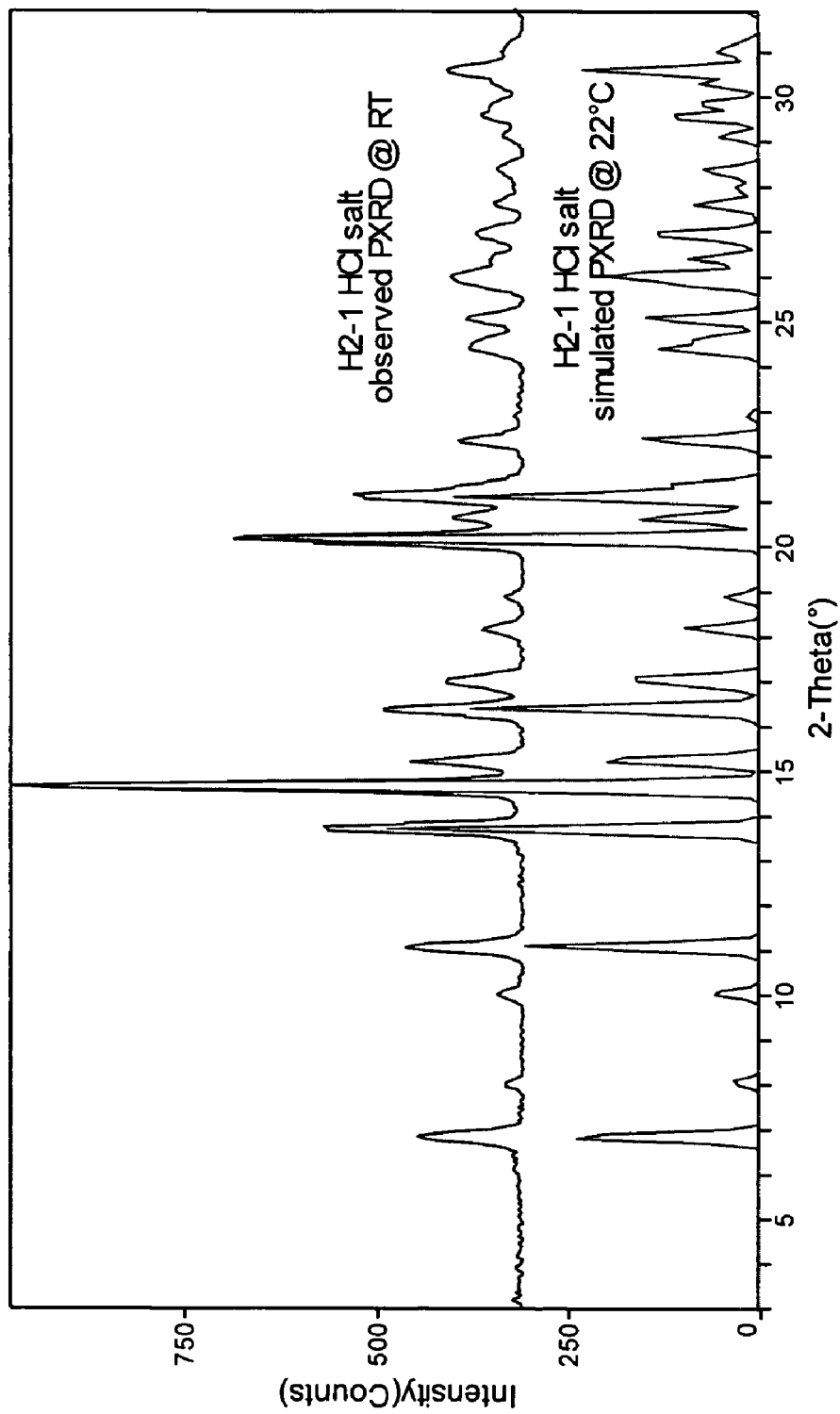
FIG. 6 shows calculated (simulated at 22° C.) and observed (experimental at room temperature) powder X-ray diffraction patterns of the crystalline saxagliptin mono HCl salt containing 2 equiv. $H_2O$ (form H2-1).

5. The method according to claim 4, wherein the crystalline compound of form H2-1 (1HCl) has an observed powder x-ray diffraction pattern as shown in FIG. 6.

6. The method according to claim 3, wherein the crystalline compound is in a form H2-1 (2HC1).

7. The method according to claim 3, wherein the crystalline compound is in a form H0.75-3.

Figure 11:
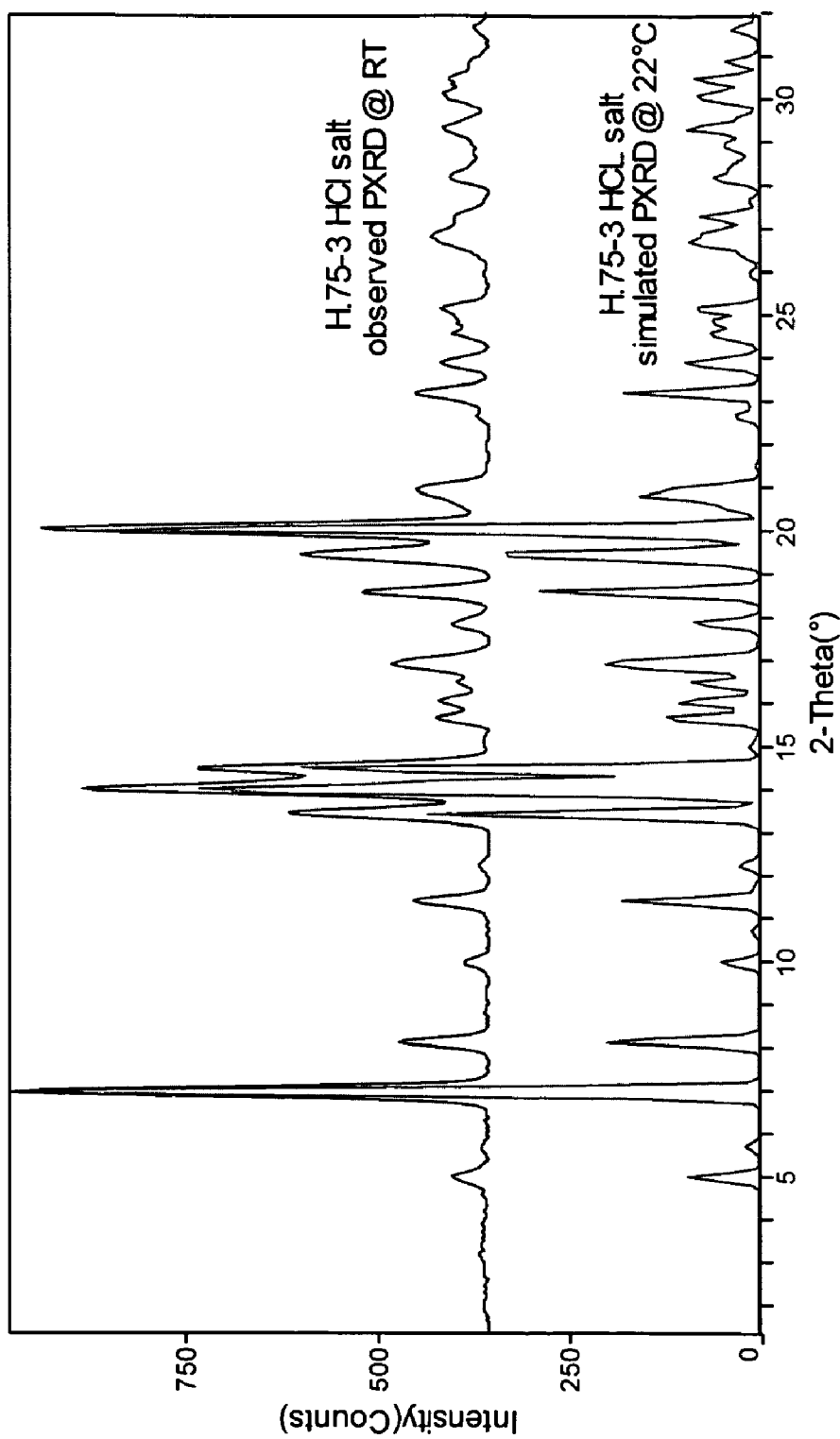
FIG. 11 shows calculated (simulated at 22° C.) and observed (experimental at room temperature) powder X-ray diffraction patterns of the crystalline saxagliptin HCl salt containing 0.75 equiv. $H_2O$ (form H0.75-3).

8. The method according to claim 7, wherein the crystalline compound of form H0.75-3 has an observed powder x-ray diffraction pattern as shown in FIG. 11.

9. The method according to claim 3, wherein the crystalline compound is in a form H1.67-1.

Figure 16:
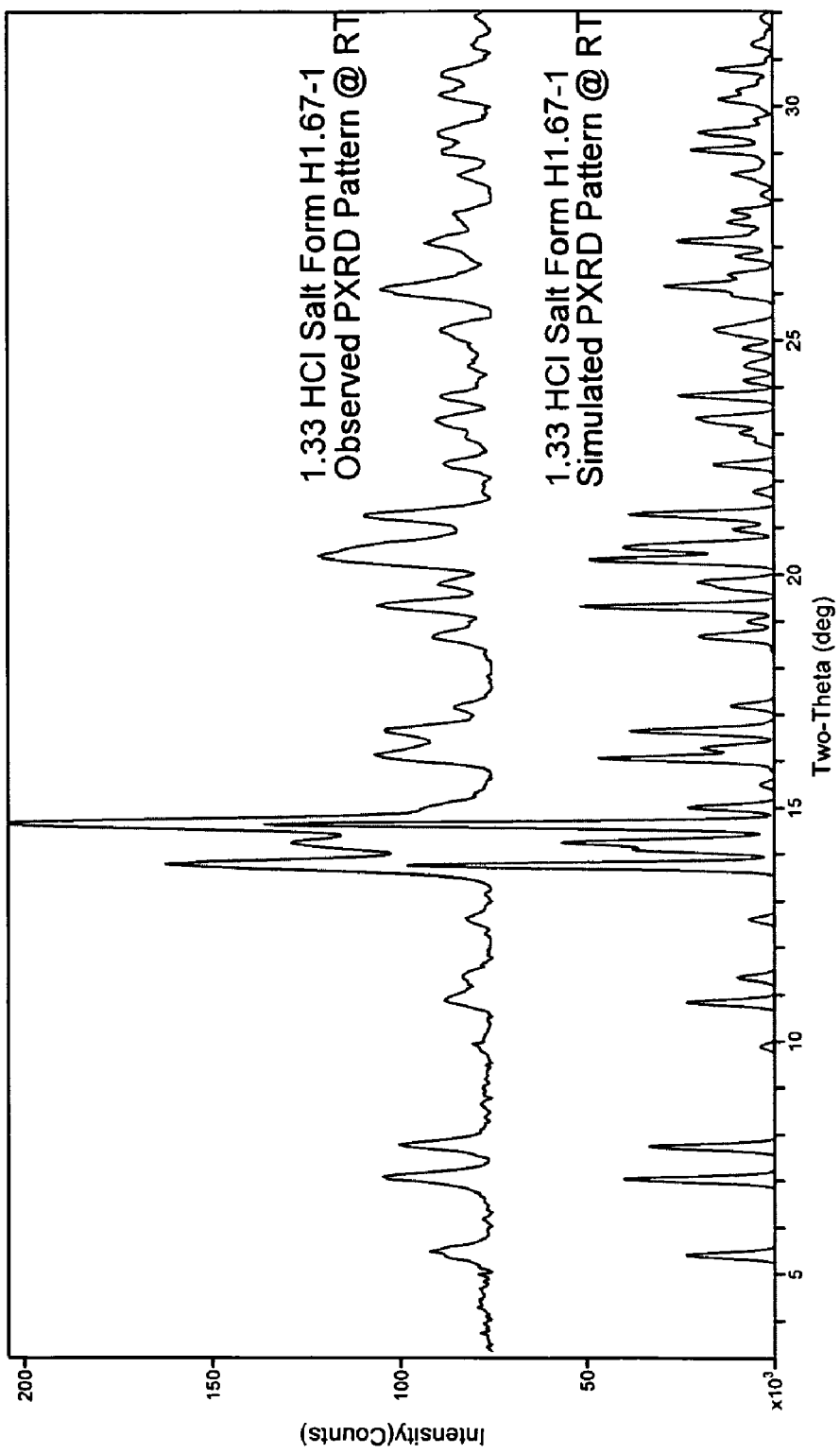
FIG. 16 shows calculated (simulated at room temperature) and observed (experimental at room temperature) powder X-ray diffraction patterns of the crystalline saxagliptin 1.33HCl salt containing 1.67 equiv. $H_2O$ (form H1.67-1).

10. The method according to claim 9, wherein the crystalline compound of form H1.67-1 has an observed powder x-ray diffraction pattern as shown in FIG. 16.

11. The method according to claim 3, wherein the crystalline compound is in a form P-5.

Figure 28:
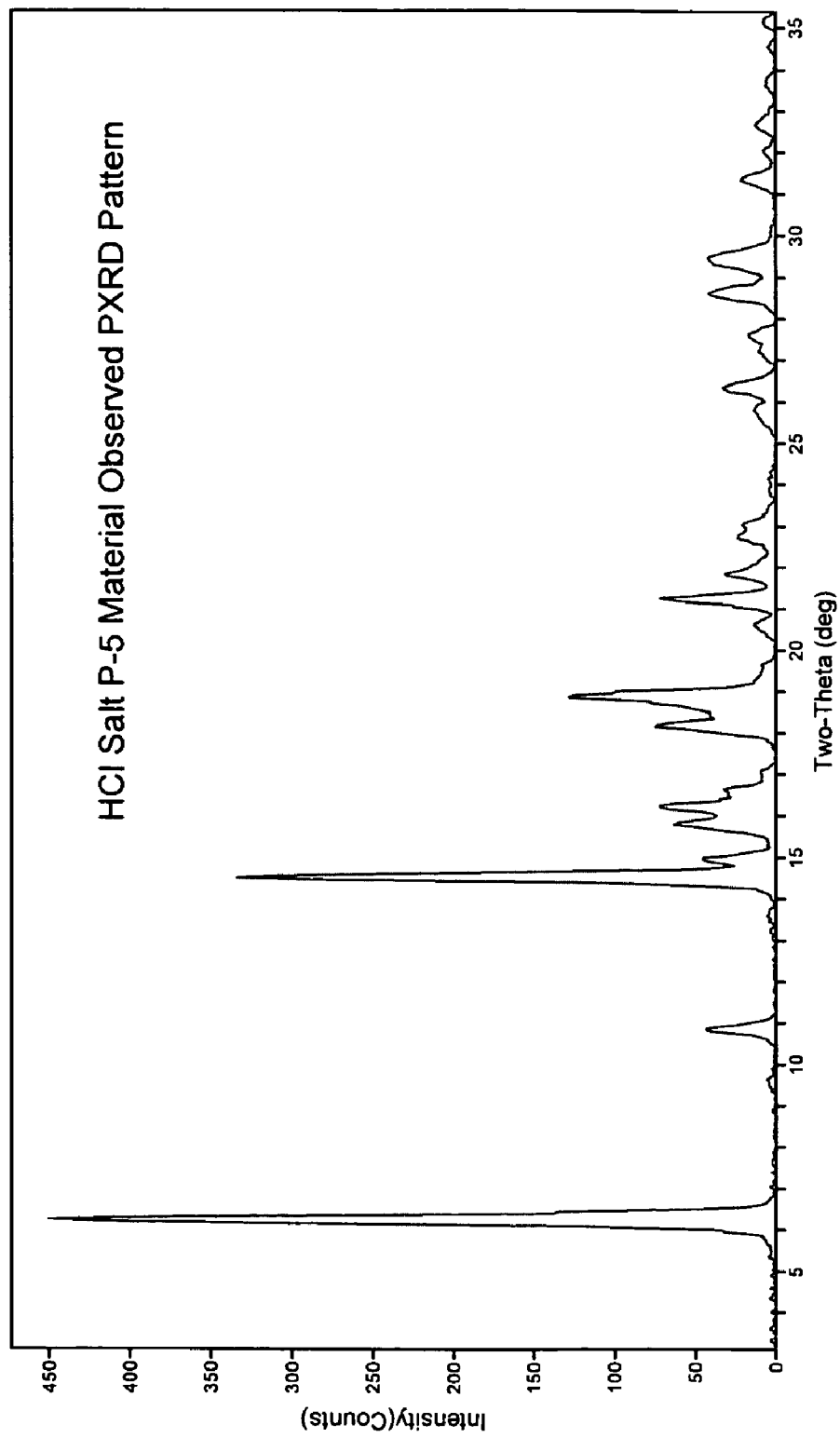
FIG. 28 shows observed (experimental at room temperature) powder X-ray diffraction patterns of the crystalline saxagliptin HCl salt Pattern P-5 (in slurry form).
Figure 29:
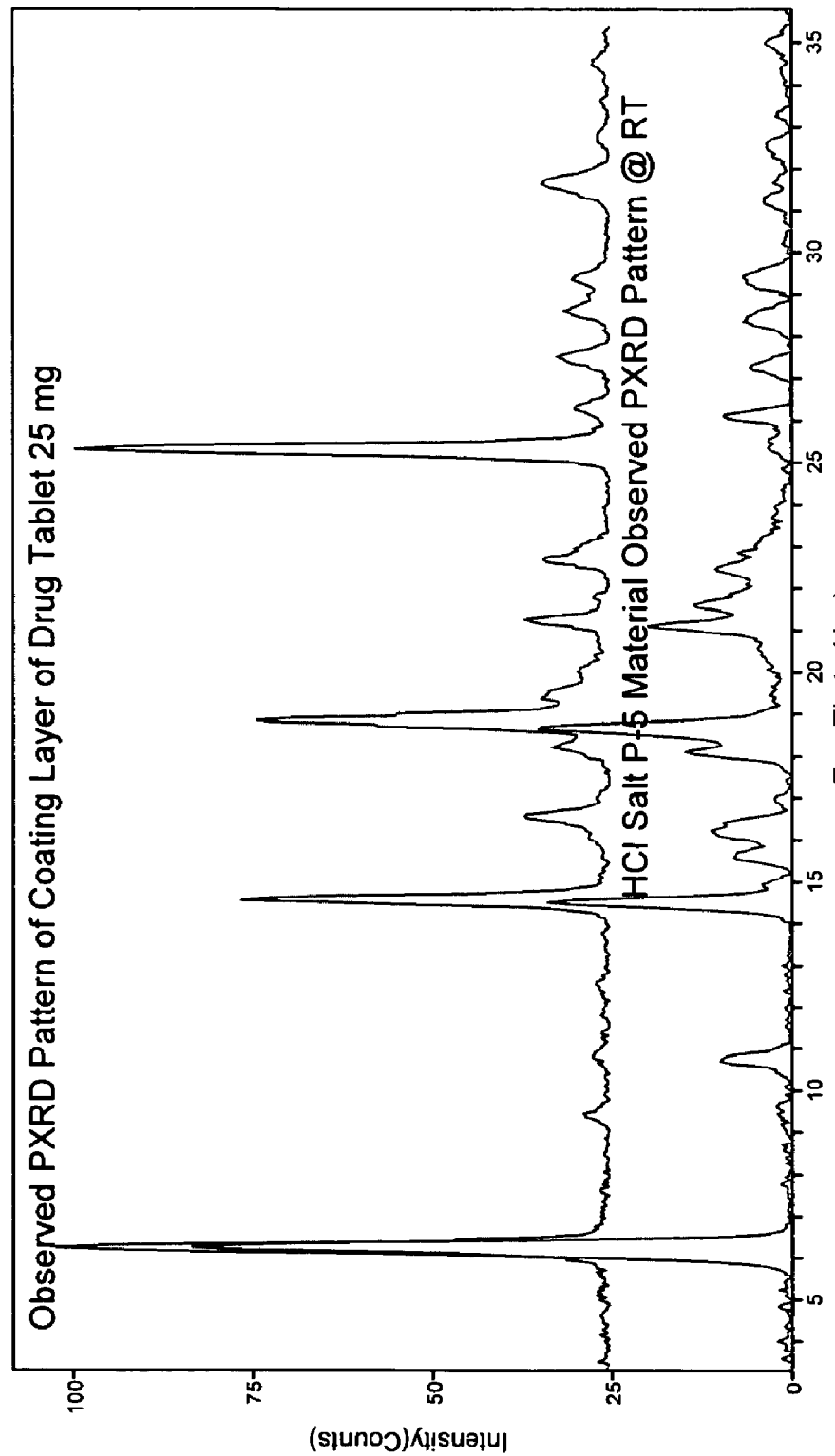
FIG. 29 shows observed (experimental at room temperature) powder X-ray diffraction patterns of the crystalline saxagliptin HCl salt Pattern P-5 in the coating layer of saxagliptin tablet (25 mg) (as a slurry sample).

12. The method according to claim 11, wherein the crystalline compound of form P-5 has an observed powder x-ray diffraction pattern as shown in FIG. 28.

13. The method according to claim 1, wherein the crystalline compound is in a form selected from N-3, H-1 (1H$_2$O), H-1 (1PhCO$_2$H/1H$_2$O), and N-1, and mixtures thereof.

14. The method according to claim 13, wherein the crystalline compound is of form N-3.

15. The method according to claim 11, wherein the crystalline compound of form N-3 has an observed powder x-ray diffraction pattern as shown in FIG. 25.

16. The method according to claim 13, wherein the crystalline compound is of form H-1 (1H$_2$O).

17. The method according to claim 16, wherein the crystalline compound of form H-1 (1H$_2$O) has an observed powder x-ray diffraction pattern as shown in FIG. 1.

18. The method according to claim 13, wherein the crystalline compound is of form H-1 (1PhCO$_2$H/1H$_2$O).

Figure 22:
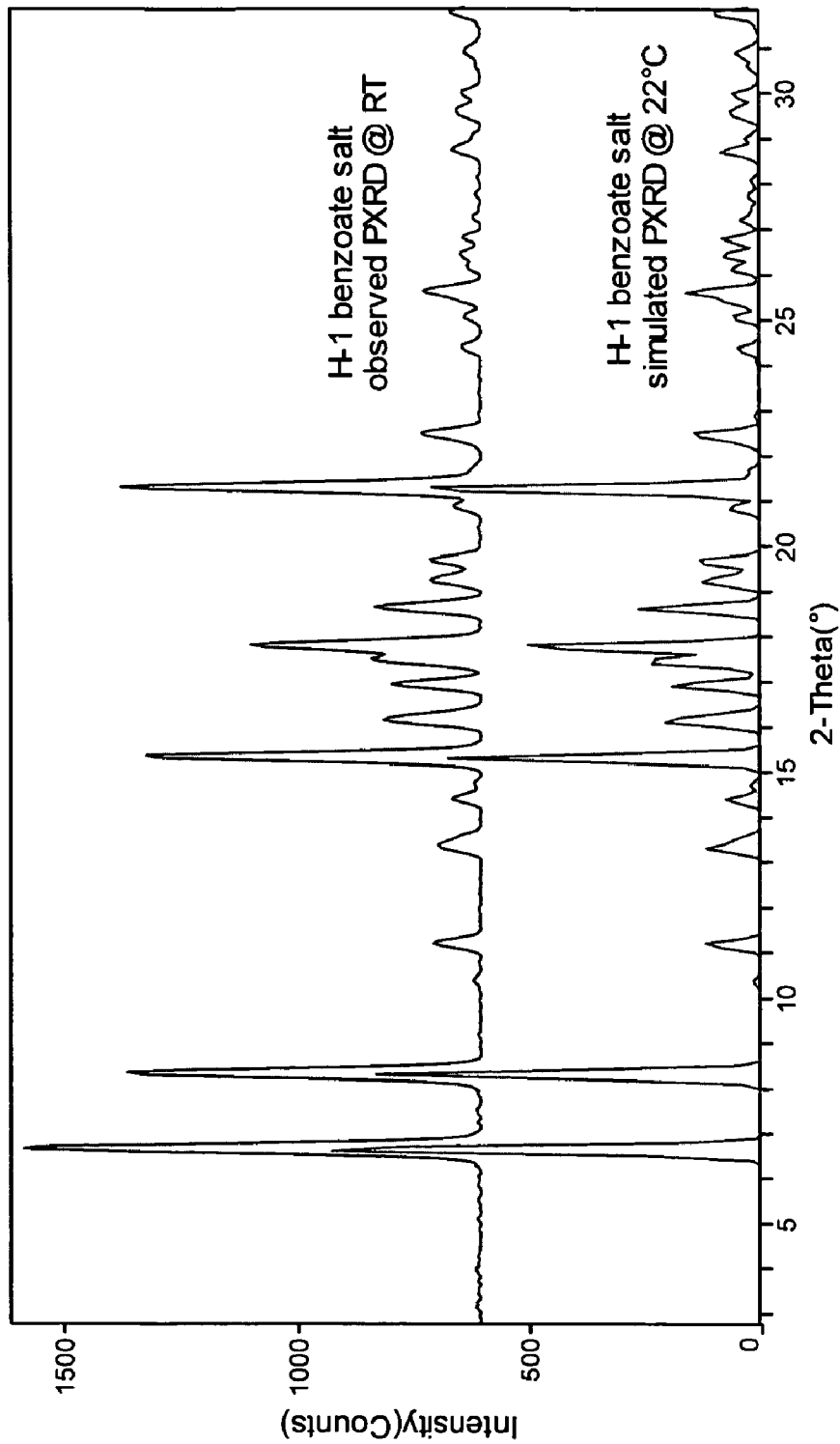
FIG. 22 shows calculated (simulated at 22° C.) and observed (experimental at room temperature) powder X-ray diffraction patterns of the crystalline saxagliptin benzoate salt (form H-1).

19. The method according to claim 18, wherein the crystalline compound of form H-1 (1PhCO$_2$H/1H$_2$O) according to claim 18 has an observed powder x-ray diffraction pattern as shown in FIG. 22.

20. The method according to claim 13, wherein the crystalline compound is of form N-1.

Figure 21:
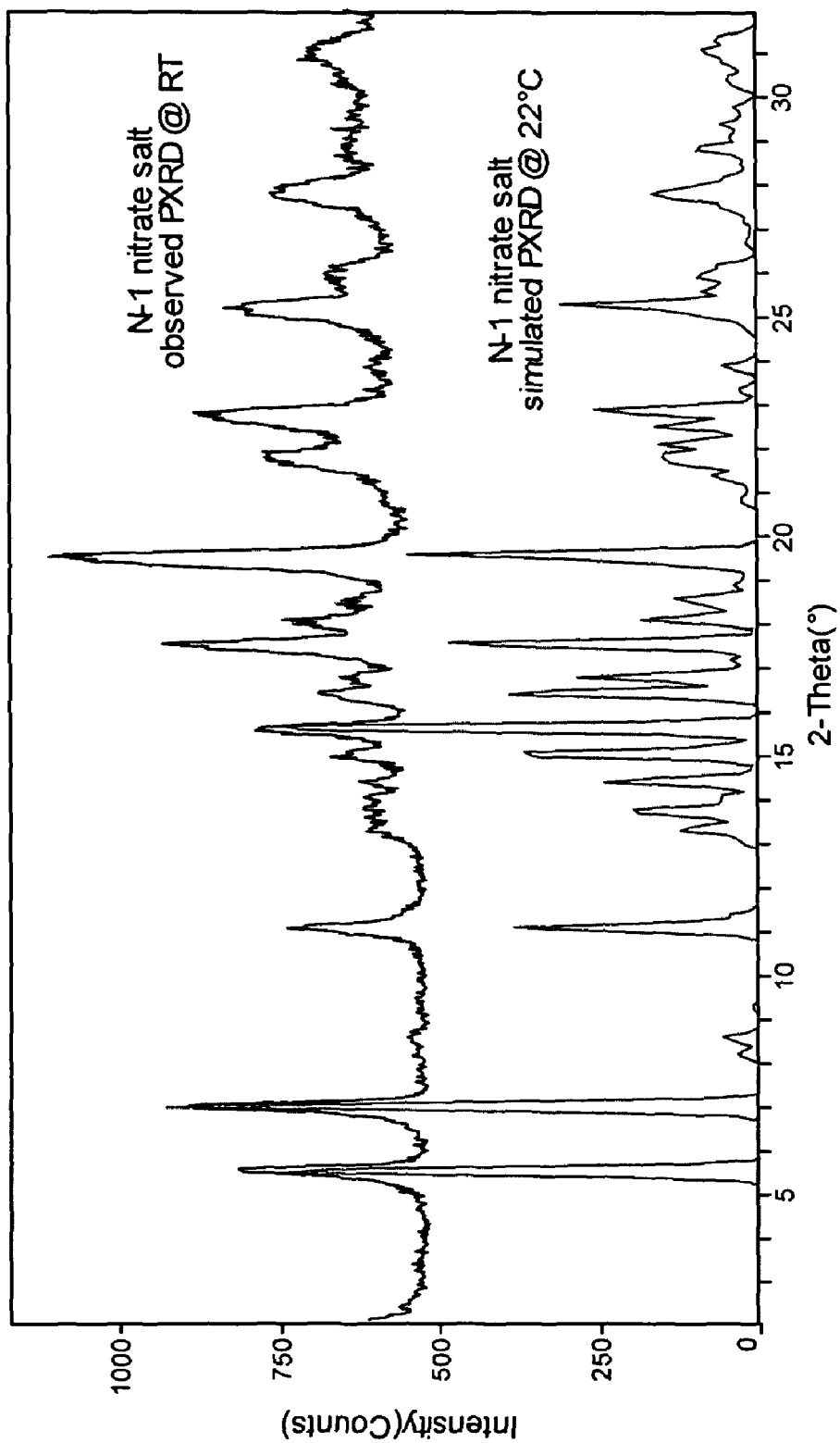
FIG. 21 shows calculated (simulated at 22° C.) and observed (experimental at room temperature) powder X-ray diffraction patterns of the crystalline saxagliptin nitrate salt (form N-1).

21. The method according to claim 20, wherein the crystalline compound of form N-1 has an observed powder x-ray diffraction pattern as shown in FIG. 21.

22. The method according to claim 1, wherein the crystalline compound is administered in combination with at least one or more antidiabetic agent(s) other than a DPP4 inhibitor for treating diabetes.

23. The method according to claim 22 wherein the antidiabetic agent is a biguanide, a sulfonyl urea, a glucosidase inhibitor, a PPAR γ agonist, a CTEP inhibitor, a PPAR α/γ dual agonist, an SGLT2 inhibitor, an aP2 inhibitor, a glycogen phosphorylase inhibitor, an AGE inhibitor, an insulin sensitizer, a glucagon-like peptide-1 (GLP-1) or mimetic thereof, insulin and/or a meglitinide.

24. The method according to claim 22 wherein the antidiabetic agent is metformin, glyburide, glimepiride, glipyride, glipizide, chlorpropamide, gliclazide, acarbose, miglitol, pioglitazone, troglitazone, dapagliflozin, rosiglitazone, insulin, G1-262570, isaglitazone, JTT-501, NN-2344, L895645, YM-440, R-119702, AJ9677, repaglinide, nateglinide, KAD1129, APR-HO39242, GW-409544, KRP297, AC2993, Exendin-4, LY307161, NN2211, and/or LY315902.

25. The method according to claim 22 wherein the antidiabetic agent is metformin, glyburide, glipizide, or dapagliflozin.

26. The method according to claim 22 wherein the antidiabetic agent is metformin or dapagliflozin.

27. The method according to claim 22 wherein the antidiabetic agent is dapagliflozin.

28. The method according to claim 1, wherein the crystalline compound is administered in combination with an anti-obesity agent.

29. The method according to claim 28, wherein the anti-obesity agent is orlistat, ATL-962, AJ9677, L750355, CP331648, sibutramine, topiramate, axokine, dexamphetamine, phentermine, phenylpropanolamine, famoxin, and/or mazindol.

30. The method according to claim 1, wherein the crystalline compound is administered in combination with a lipid modulating agent.

31. The method according to claim 30, wherein the lipid modulating agent is pravastatin, lovastatin, simvastatin, atorvastatin, cerivastatin, fluvastatin, nisvastatin, ZD-4522, fenofibrate, gemfibrozil, clofibrate, implitapide, CP-529,414, avasimibe, TS-962, MD-700, and/or LY295427.

* * * * *

UNITED STATES PATENT AND TRADEMARK OFFICE
CERTIFICATE OF CORRECTION

PATENT NO.       : 8,236,847 B2
APPLICATION NO.  : 13/081341
DATED            : August 7, 2012
INVENTOR(S)      : Gougoutas et al.

It is certified that error appears in the above-identified patent and that said Letters Patent is hereby corrected as shown below:

In the Claims

In Claim 6, at Column 60, Line 52 "(2HC1)" should be replaced with "(2HCl)".

Signed and Sealed this
Thirteenth Day of May, 2014

Michelle K. Lee
*Deputy Director of the United States Patent and Trademark Office*